United States Patent
Conner et al.

(10) Patent No.: US 11,612,626 B2
(45) Date of Patent: Mar. 28, 2023

(54) ONCOLYTIC HERPES SIMPLEX VIRUS INFECTED CELLS

(71) Applicants: Virttu Biologies Limited, San Diego, CA (US); The University of Sheffield, Sheffield (GB)

(72) Inventors: Joe Conner, Lanarkshire (GB); Munitta Muthana, Sheffield (GB); Claire Elizabeth Lewis, Sheffield (GB)

(73) Assignees: Virttu Biologics Limited, London (GB); The University of Sheffield, Sheffield (GB)

( * ) Notice: Subject to any disclaimer, the term of this patent is extended or adjusted under 35 U.S.C. 154(b) by 11 days.

(21) Appl. No.: 16/790,459

(22) Filed: Feb. 13, 2020

(65) Prior Publication Data
US 2020/0289590 A1 Sep. 17, 2020

Related U.S. Application Data

(62) Division of application No. 15/557,783, filed as application No. PCT/EP2016/055325 on Mar. 11, 2016, now Pat. No. 10,596,210.

(30) Foreign Application Priority Data

Mar. 13, 2015 (GB) ..................... 1504251

(51) Int. Cl.
*A01N 63/00* (2020.01)
*A61K 35/763* (2015.01)
(Continued)

(52) U.S. Cl.
CPC .......... *A61K 35/763* (2013.01); *A61K 9/0009* (2013.01); *A61K 9/19* (2013.01); *A61K 9/5068* (2013.01); *A61K 33/26* (2013.01); *A61K 35/15* (2013.01); *A61K 41/00* (2013.01); *A61K 47/6901* (2017.08); *A61M 37/00* (2013.01);
(Continued)

(58) Field of Classification Search
None
See application file for complete search history.

(56) References Cited

U.S. PATENT DOCUMENTS 8,852,927 B2 * 10/2014 Szalay .................. A61K 35/76
435/320.1
2002/0068048 A1 6/2002 Dreyfus et al.
(Continued)

FOREIGN PATENT DOCUMENTS

JP 2004-099584 4/2004
JP 2004-521938 7/2004
(Continued)

OTHER PUBLICATIONS

Toyoizumi et al., "Combined therapy with chemotherapeutic agents and herpes simplex virus type I ICP34.5 mutant (HSV-1716) in human non-small cell lung cancer," Human Gene Ther. 10:3013-3029 (abstract only) (Year: 1990).*
(Continued)

*Primary Examiner* — M Franco G Salvoza
(74) *Attorney, Agent, or Firm* — McNeill Baur PLLC

(57) ABSTRACT

A monocyte, monocyte derived cell or macrophage infected with an oncolytic herpes simplex virus is disclosed together with uses of such infected cells in the treatment of diseases such as cancer.

14 Claims, 37 Drawing Sheets
Specification includes a Sequence Listing.

(51) Int. Cl.
    *A61K 41/00*     (2020.01)
    *C12N 5/0786*     (2010.01)
    *A61K 35/15*     (2015.01)
    *A61K 9/19*     (2006.01)
    *A61M 37/00*     (2006.01)
    *A61K 9/00*     (2006.01)
    *A61K 47/69*     (2017.01)
    *A61K 33/26*     (2006.01)
    *A61K 9/50*     (2006.01)
    *C12N 7/00*     (2006.01)

(52) U.S. Cl.
    CPC ............. *C12N 5/0645* (2013.01); *C12N 7/00* (2013.01); *C12N 2710/16632* (2013.01)

(56) References Cited

U.S. PATENT DOCUMENTS

| | | | |
|---|---|---|---|
| 2004/0009604 A1* | 1/2004 | Zhang | C12N 7/00 435/456 |
| 2009/0180994 A1 | 7/2009 | Groene et al. | |
| 2009/0285860 A1 | 11/2009 | Martuza et al. | |
| 2015/0231269 A1 | 8/2015 | Kaittanis et al. | |

FOREIGN PATENT DOCUMENTS

| | | |
|---|---|---|
| WO | 1992/013943 A1 | 8/1992 |
| WO | 02/091997 A2 | 11/2002 |
| WO | 2007/025365 A1 | 3/2007 |
| WO | 2007/113572 A1 | 10/2007 |
| WO | 2010/025322 A2 | 3/2010 |
| WO | 2013/071015 A1 | 5/2013 |

OTHER PUBLICATIONS

English translation of Ji et al., "Herpes Simplex Virus Infects Monocyte-macrophages," Foreign Medical Sciences (Microbiology), 17 (04) 156-158, 161 (Year: 1994).*
Fu, Xinping et al., "Expression of a Fusogenic Membrane Glycoprotein by an Oncolytic Herpes Simplex Virus Potentiates the Viral Antitumor Effect", Molecular Therapy, vol. 7, No. 6, Jun. 2003, pp. 748-754.
Melchjorsen, Jesper et al., "Induction of Cytokine Expression by Herpes Simplex Virus in Human Monocyte-Derived Macrophages and Dendritic Cells is Dependent on Virus Replication and is Counteracted by ICP27 Targeting NF-KB and IRF-3", Journal of General Virology, vol. 87, 2006, pp. 1099-1108.
Braidwood, Lynne et al., "Oncolytic Herpes Viruses, Chemotherapeutics, and Other Cancer Drugs", Oncolytic Virotherapy, vol. 2, 2013, pp. 57-74.
Conner et al., "A strategy for systemic delivery of the oncolytic herpes virus HSV1716: redirected tropism by antibody-binding sites incorporated on the virion surface as a glycoprotein D fusion protein," Gene Therapy 15: 1579-1592 (Year: 2008).
Andreesen et al. (1998) "Adoptive immunotherapy of cancer using monocyte-derived macrophages: rationale, current status, and perspectives," J. Leukoc. Biol. 64(4):419-26.
Benencia et al. (2008) "Herpes virus oncolytic therapy reverses tumor immune dysfunction and facilitates tumor antigen presentation," Cancer Biol Ther. 7(8):1194-205.

Carreau et al. (2011) Why is the partial oxygen pressure of human tissues a crucial parameter? Small molecules and hypoxia, J. Cell. Mol. Med. 15(6):1239-53.
Darcy et al. (Apr. 2014) "Manipulating immune cells for adoptive immunotherapy of cancer," Curr. Opin. Immunol. 27:46-52.
Hockel et al. (2001) "Tumor Hypoxia: Definitions and Current Clinical, Biologic, and Molecular Aspects," J. Natl. Cancer Inst. 93(4):266-76.
Hui et al. (2009) "Induction of Proinflammatory Cytokines in Primary Human Macrophages by Influenza A Virus (H5N1) Is Selectively Regulated by IFN Regulatory Factor 3 and p38 MAPK," J. Immunol. 182:1088-1098.
Kizaka-Kondoh et al. (2003) "Tumor hypoxia: A target for selective cancer therapy," Cancer Sci. 94(12):1021-1028.
Lewis et al. (2005) "Macrophage responses to hypoxia: implications for tumor progression and anti-cancer therapies," Am. J. Pathol. 167(3):627-635.
Muthana et al. (2008) "A novel magnetic approach to enhance the efficacy of cellbased gene therapies," Gene Therapy. 15:902-910.
Muthana et al. (Aug. 18, 2015) "Directing cell therapy to anatomic target sites in vivo with magnetic resonance targeting," Nat. Commun. 6:8009. pp. 1-11.
Muthana et al. (Nov. 20, 2012) "Macrophage Delivery of an Oncolytic Virus Abolishes Tumor Regrowth and Metastasis after Chemotherapy or Irradiation," Cancer Res 73:490-495.
Muthana et al. (2011) "Use of Macrophages to Target Therapeutic Adenovirus to Human Prostate Tumors," Cancer Res. 71(5):1805-1815.
Power et al. (2007) "Cell-based delivery of Oncolytic Viruses: A New Strategic Alliance for a Biological Strike Against Cancer," Mol. Ther. 15(4):660-665.
International Search Report with Written Opinion corresponding to International Patent Aoolication No. PCT/EP2016/055325, dated Jun. 8, 2016.
JI Xiaohui et al., "Herpes Simplex Virus Infects Monocyte-macrophages", Foreign Medical Sciences (Microbiology), 17 (04), pp. 156-158 and 161.
Office Action dated Jul. 21, 2021, in corresponding to Chinese Application No. 201680027784.4, 15 pages.
Xiang et al.; Molecular Ecology; Feb. 29, 1996; pp. 62-64; ISBN: 7-5352-1724-9; Hubei Science and Technology Press; Wuhan, China.
Jiang et al., "CXCL10 expression and prognostic significance in stage II and III colorectal cancer," Mol Biol Rep (2010) 37:3029-3036.
Jing et al., "Replication of Herpes Simplex Virus 1 Depends on the gamma 1 34.5 Functions That Facilitate Virus Response to Interferon and Egress in the Different Stages of Productive Infection," Journal of Virology, Jul. 2004, vol. 78, No. 14, p. 7653-7666.
Mohr et al., "A herpesvirus genetic element which affects translation in the absence of the viral GADD34 function," The EMBO Journal, vol. 15 no. 17, pp. 4759-4766, 1996.
Oft, "IL-10: Master Switch from Tumor-Promoting Inflammation to Antitumor Immunity," Cancer Immunol Res; 2(3) Mar. 2014, pp. 194-199.
Pasieka et al., "Functional Genomic Analysis of Herpes Simplex Virus Type 1 Counteraction of the Host Innate Response," Journal of Virology, Aug. 2006, vol. 80, No. 15, p. 7600-7612.

\* cited by examiner

|  | control | MOI 5 | MOI 50 |
|---|---|---|---|
| Normoxia | 0 ± 0.0 | 287 ± 67.6 | 802 ± 115.2 |
| Hypoxia | 0 ± 0.0 | 700 ± 105.1 | 3302 ± 860.8 |

| IL-6 | IL-8 | TNFα | IL-1 | NFκB | TGFβ | IL-10 | VEGFA | CXCL6 | CXCL1 |
|---|---|---|---|---|---|---|---|---|---|
| 1.28 | 1.03 | 1.46 | 1.03 | 0.56 | 0.55 | 0.52 | 1.18 | 0.89 | 0.75 |
| 2.37 | 5.13 | 2.74 | 7.52 | 5.12 | 2.50 | 4.44 | 21.58 | 1.52 | 1.52 |

ONCOLYTIC HERPES SIMPLEX VIRUS INFECTED CELLS

This application is a divisional of U.S. patent application Ser. No. 15/557,783, which has a 35 U.S.C. § 371(c) date of Sep. 12, 2017, which issued as U.S. Pat. No. 10,596,210 on Mar. 24, 2020, and is a national phase entry under 35 U.S.C. § 371 of International Patent Application No. PCT/EP2016/055325, filed Mar. 11, 2016, which claims priority to United Kingdom Patent Application No. 1504251.8 filed Mar. 13, 2015, all of which are incorporated by reference herein in their entirety.

SEQUENCE LISTING

This application contains a Sequence Listing that has been submitted electronically in ASCII format and is hereby incorporated by reference in its entirety. Said ASCII copy, created on Sep. 12, 2017, is named 2017-09-12_01246-0002-00US_SL.txt and is 8,192 bytes in size.

FIELD OF THE INVENTION

The present invention relates to a monocyte, monocyte derived cell or macrophage infected with an oncolytic herpes simplex virus, and uses of such infected cells in the treatment of diseases such as cancer.

BACKGROUND TO THE INVENTION

Cancer is one of the greatest concerns worldwide, because of the high mortality rates, the economic and social burden associated with it and the psychological issues faced by cancer survivors.

Resistance to treatments is generally acquired when tumor mass presents areas which are not reached or affected by conventional therapies, i.e. chemotherapy or radiotherapy. These regions are located at the centre of the tumor bulk and are generally characterised by a highly hypoxic environment, meaning that the oxygen supply is insufficient for the appropriate respiration of cells and stroma (Shannon, A. M., D. J. Bouchier-Hayes, C. M. Condron and D. Toomey, 2003 Tumour hypoxia, chemotherapeutic resistance and hypoxia-related therapies. Cancer Treatment Reviews 29: 297-307). The hypoxic condition, which is an invariable characteristic of solid tumors, develops because the rate of cell replication in tumors overcomes that of vessel formation: continuous demand of oxygen, thus, is detected by cellular oxygen sensors which address the need by stimulating the angiogenic sprouting. In turn, angiogenesis leads to the generation of structurally disordered blood vessels with improper distribution within the cancer mass (Kandel, J. J., D. J. Yamashiro and J. Kitajewski, 2011 Angiogenesis in Tumour Development and Metastasis, pp. 81-93 in *Therapeutic Angiogenesis for Vascular Diseases: Molecular Mechanisms and Targeted Clinical Approaches for the Treatment of Angiogenic Disease*, edited by M. Slevin. Springer-Verlag Berlin, Berlin): this causes the development of a dysfunctional microvasculature that leads to the inadequate diffusion and perfusion of oxygen throughout the mass of tumor (Vaupel, P., O. Thews and M. Hoeckel, 2001 Treatment resistance of solid tumors—Role of hypoxia and anemia. Medical Oncology 18: 243-259). Ultimately, this creates a feedback loop which further increases hypoxia.

An important feature of hypoxic areas of cancers is the marked presence of immune cells, which infiltrate into the tumor mass since the very early stages of cancer onset (Di Caro, G., F. Marchesi, L. Laghi and F. Grizzi, 2013 Immune cells: plastic players along colorectal cancer progression. Journal of Cellular and Molecular Medicine 17: 1088-1095). Among the most studied cell types are tumor-associated macrophages (TAMs). TAMs are a population of macrophages that mobilise and accumulate in great number in the hypoxic central areas of solid tumors (Turner, L., C. Scotton, R. Negus and F. Balkwill, 1999 Hypoxia inhibits macrophage migration. European Journal of Immunology 29: 2280-2287; Lewis, J. S., R. J. Landers, J. C. E. Underwood, A. L. Harris and C. E. Lewis, 2000 Expression of vascular endothelial growth factor by macrophages is up-regulated in poorly vascularized areas of breast carcinomas. Journal of Pathology 192: 150-158; Gollapudi, K., C. Galet, T. Grogan, H. Zhang, J. W. Said et al., 2013 Association between tumor-associated macrophage infiltration, high grade prostate cancer, and biochemical recurrence after radical prostatectomy. American Journal of Cancer Research 3: 523-529). TAMs are characterised by a specific phenotype, activated in response to micro-environmental signals such as cytokines, growth factors and hormones (Martinez, F. O., S. Gordon, M. Locati and A. Mantovani, 2006 Transcriptional profiling of the human monocyte-to-macrophage differentiation and polarization: New molecules and patterns of gene expression. Journal of Immunology 177: 7303-7311), that are often referred to as M2 macrophages. While their counterparts, M1-polarised macrophages, are activated in response to inflammatory molecules and are characterised by high anti-tumor and immuno-stimulatory functions, the M2-skewed macrophages express marked pro-tumor activities, suppressing inflammatory processes and promoting matrix remodelling, invasion, angiogenesis and survival (Sica, A., T. Schioppa, A. Mantovani and P. Allavena, 2006 Tumour-associated macrophages are a distinct M2 polarised population promoting tumour progression: Potential targets of anti-cancer therapy. European Journal of Cancer 42: 717-727).

TAMs are known to be recruited from the blood circulation by chemotactic cytokines which are continuously released by tumor cells; for instance, MCP-1, VEGF and CSF-1 expression was found to be positively correlated with TAM accumulation in numerous human tumors (Graves, D. T., R. Barnhill, T. Galanopoulos and H. N. Antoniades, 1992 EXPRESSION OF MONOCYTE CHEMOTACTIC PROTEIN-1 IN HUMAN-MELANOMA INVIVO. American Journal of Pathology 140: 9-14; Kacinski, B. M., 1995 CSF-1 AND ITS RECEPTOR IN OVARIAN, ENDOMETRIAL AND BREAST-CANCER. Annals of Medicine 27: 79-85. Arenberg, D. A., M. P. Keane, B. DiGiovine, S. L. Kunkel, S. R. B. Strom et al., 2000 Macrophage infiltration in human non-small-cell lung cancer: the role of CC chemokines. Cancer Immunology Immunotherapy 49: 63-70; Lewis, J. S., R. J. Landers, J. C. E. Underwood, A. L. Harris and C. E. Lewis, 2000 Expression of vascular endothelial growth factor by macrophages is up-regulated in poorly vascularized areas of breast carcinomas. Journal of Pathology 192: 150-158). However, their specific accumulation into hypoxic regions of tumors is fostered by several features: the marked presence of necrotic cells (Lewis, J., R. J. Landers, R. D. Leek, K. Corke, A. L. Harris et al., 1997 Role of macrophages in tumour angiogenesis: Regulation by hypoxia. Journal of Pathology 182: A1-A1) and the release of a number of chemo-attractants, such as MCP-1 (Li, X., H. Kimura, K. Hirota, H. Sugimoto and H. Yoshida, 2005 Hypoxia reduces constitutive and TNF-alpha-induced expression of monocyte chemoattractant protein-1 in human proximal renal tubular cells. Biochemical and Biophysical Research Communications 335: 1026-1034), VEGF (Brown, L. F., B. Berse, R. W. Jackman, K. Tognazzi, A. J. Guidi et al., 1995 EXPRESSION OF VASCULAR-PERMEABILITY FACTOR (VASCULAR ENDOTHELIAL GROWTH-FACTOR) AND ITS RECEPTORS IN BREAST-CANCER. Human Pathology 26: 86-91) and endothelins (Grimshaw, M. J., S. Naylor and F. R. Balkwill, 2002 Endothelin-2 is a hypoxia-induced autocrine survival factor for breast tumor cells. Molecular Cancer Therapeutics 1: 1273-1281). Once amassed into hypoxic areas, TAMs respond to oxygen-depleted conditions through an increase in production and release of several factors, such as growth factors, MMPs and CXCLs, which in turn affect angiogenesis, cellular growth, invasive capabilities and metastasis: thus, TAMs ultimately promote tumor progression (Sica, A., T. Schioppa, A. Mantovani and P. Allavena, 2006 Tumour-associated macrophages are a distinct M2 polarised population promoting tumour progression: Potential targets of anti-cancer therapy. European Journal of Cancer 42: 717-727).

Given their pivotal role in triggering cancer progression, infiltration of TAMs in tumors has been correlated with poor prognosis in the majority of solid cancers: lung cancer (Chen, J. J. W., Y. C. Lin, P. L. Yao, A. Yuan, H. Y. Chen et al., 2005 Tumor-associated macrophages: The double-edged sword in cancer progression. Journal of Clinical Oncology 23: 953-964), oral squamous cell carcinoma (He, K.-F., L. Zhang, C.-F. Huang, S.-R. Ma, Y.-F. Wang et al., 2014 CD163+ Tumor-Associated Macrophages Correlated with Poor Prognosis and Cancer Stem Cells in Oral Squamous Cell Carcinoma. BioMed research international 2014: 838632), papillary thyroid carcinoma (KIM et al. 2013), papillary renal cell carcinoma (Behnes, C. L., F. Bremmer, B. Hemmerlein, A. Strauss, P. Strobel et al., 2014 Tumor-associated macrophages are involved in tumor progression in papillary renal cell carcinoma. Virchows Archiv 464: 191-196), breast cancer (Mukhtar, R. A., A. P. Moore, V. J. Tandon, O. Nseyo, P. Twomey et al., 2012 Elevated Levels of Proliferating and Recently Migrated Tumor-associated Macrophages Confer Increased Aggressiveness and Worse Outcomes in Breast Cancer. Annals of Surgical Oncology 19: 3979-3986; Tang, X. Q., 2013 Tumor-associated macrophages as potential diagnostic and prognostic biomarkers in breast cancer. Cancer Letters 332: 3-10), ovarian cancer (Lan, C. Y., X. Huang, S. X. Lin, H. Q. Huang, Q. C. Cai et al., 2013 Expression of M2-Polarized Macrophages is Associated with Poor Prognosis for Advanced Epithelial Ovarian Cancer. Technology in Cancer Research & Treatment 12: 259-267) and pancreatic cancer (Kurahara, H., S. Takao, T. Kuwahata, T. Nagai, Q. Ding et al., 2012 Clinical Significance of Folate Receptor beta-expressing Tumor-associated Macrophages in Pancreatic Cancer. Annals of Surgical Oncology 19: 2264-2271).

Oncolytic virotherapy concerns the use of lytic viruses which selectively infect and kill cancer cells. Some oncolytic viruses are promising therapies as they display exquisite selection for replication in cancer cells and their self-limiting propagation within tumors results in fewer toxic side effects. Several oncolytic viruses have shown great promise in the clinic (Bell, J., Oncolytic Viruses: An Approved Product on the Horizon? Mol Ther. 2010; 18(2): 233-234).

Macrophages are known to have a natural homing ability to a site of disease and have been proposed as cellular vehicles for gene therapy (Burke et al., Macrophages in gene therapy: cellular delivery vehicles and in vivo targets. Journal of Leukocyte Biology Vol. 72, no. 3 417-428).

WO2007/113572 describes monocyte derived cells, e.g, macrophages, that comprise a magnetic material. The cells are described to be useful as a vehicle for targeting a therapeutic agent to a diseased material in a subject, where the therapeutic agent may preferably be a gene (i.e. a gene therapy approach to treatment of the diseased material) and the subject requiring treatment is exposed to a magnetic field to assist location of the cells in the diseased material. Related work is disclosed in Muthana et al. A novel magnetic approach to enhance the efficacy of cell-based gene therapies. Gene Therapy (2008) 15, 902-910.

Muthana et al., (Use of Macrophages to Target Therapeutic Adenovirus to Human Prostate Tumors. Cancer Res; 71(5) Mar. 1, 2011) describe an approach to treatment of prostate tumors in which macrophages were transduced with a hypoxia-regulated E1A/B construct and an E1A-dependent oncolytic adenovirus, whose proliferation was also restricted to prostate tumor cells using prostate-specific promoter elements to control E1A expression. In these experiments the macrophages were used as 'silent carriers' of the adenovirus which was only induced to replicate upon location in a hypoxic environment. Induction of replication of adenovirus did not lead to death of the macrophages. In Muthana et al., (Macrophage Delivery of an Oncolytic Virus Abolishes Tumor Regrowth and Metastasis after Chemotherapy or Irradiation. Cancer Res; 73(2) Jan. 15, 2013) the authors describe experiments using the same adenoviral approach to investigate the effects post-administration of docetaxel or radiation therapy.

SUMMARY OF THE INVENTION

The present invention concerns a monocyte, monocyte derived cell or macrophage which is infected with an oncolytic Herpes Simplex Virus. The infected monocyte, monocyte derived cell or macrophage is disclosed to be useful in a method of treatment of disease, in particular the treatment of cancer. Preferred treatments may include treatment of a tissue or cancer that is hypoxic or a part of a tissue or cancer that is hypoxic. Preferred treatments may include treatment of a tissue or cancer located in deep tissues, organs or in the core of the body.

The infected cell represents a specialised vector which is self-targeting to diseased tissue, thereby delivering the oncolytic Herpes Simplex Virus directly to the diseased tissue, including to hypoxic regions of tissue which are otherwise very difficult to penetrate with therapeutic agents. The cells do not act merely as a vector. Oncolytic Herpes Simplex Virus infection leads to death of the monocyte or monocyte derived cells, which may be caused by viral replication and cell lysis. Cell death whilst present in the diseased tissue therefore leads to release of oncolytic Herpes Simplex Virus and direct delivery to the diseased cells, e.g. tumor cells, which can be infected and lysed by oncolytic Herpes Simplex Virus.

Furthermore, the oncolytic Herpes Simplex Virus initiates an enhanced immune response in hypoxic tissue, thereby promoting an immune response to the disease, e.g. an anti-tumor immune response.

In some embodiments the monocyte, monocyte derived cell or macrophage may also contain an exogenous magnetic material. In these embodiments the method of treatment may involve application of a magnetic field to the subject in order to direct the monocyte, monocyte derived cell or macrophage to a desired location in the subject's body where treatment is required.

In one aspect of the present invention an ex vivo or in vitro monocyte, monocyte derived cell or macrophage infected with an oncolytic herpes simplex virus is provided.

In some embodiments the ex vivo or in vitro monocyte, monocyte derived cell or macrophage may also contain an exogenous magnetic material.

In one aspect of the present invention a preparation comprising a population of monocytes, monocyte derived cells or macrophages infected with an oncolytic herpes simplex virus is provided.

In one embodiment the monocytes, monocyte derived cells or macrophages also contain an exogenous magnetic material.

In one aspect of the present invention, the preparation is provided for use in a method of medical treatment, e.g. the treatment of cancer.

In another aspect of the present invention a method of preparing a monocyte, monocyte derived cell or macrophage infected with an oncolytic herpes simplex virus is provided, the method comprising contacting in vitro a monocyte, monocyte derived cell or macrophage with an oncolytic herpes simplex virus.

In some embodiments the method further comprises contacting the monocyte, monocyte derived cell or macrophage with a magnetic material.

In another aspect of the present invention a method of producing a preparation comprising a population of monocytes, monocyte derived cells or macrophages infected with an oncolytic herpes simplex virus is provided, the method comprising providing a population of monocytes, monocyte derived cells or macrophages infected with an oncolytic herpes simplex virus, and formulating a preparation comprising said population of cells.

In some embodiments, monocytes, monocyte derived cells or macrophages in said population contain an exogenous magnetic material.

In another aspect of the present invention a monocyte, monocyte derived cell or macrophage infected with an oncolytic herpes simplex virus, and optionally containing an exogenous magnetic material, is provided for use in a method of treatment of disease. The method of treatment may optionally comprise administering the monocyte, monocyte derived cell or macrophage to a subject and applying a magnetic field to the subject in order to direct cells containing an exogenous magnetic material to a desired location in the subject's body.

In another aspect of the present invention the use of a monocyte, monocyte derived cell or macrophage infected with an oncolytic herpes simplex virus, and optionally containing an exogenous magnetic material, in the manufacture of a medicament for use in the treatment of disease is provided. The treatment may optionally comprise administering the monocyte, monocyte derived cell or macrophage to a subject and applying a magnetic field to the subject in order to direct cells containing an exogenous magnetic material to a desired location in the subject's body.

In another aspect of the present invention a preparation comprising a population of monocytes, monocyte derived cells or macrophages infected with an oncolytic herpes simplex virus, wherein the monocytes, monocyte derived cells or macrophages contain an exogenous magnetic material, is provided for use in a method of treatment of disease, the method comprising administering the preparation to a subject and applying a magnetic field to the subject in order to direct cells of the administered preparation to a desired location in the subject's body.

In another aspect of the present invention the use of a population of monocytes, monocyte derived cells or macrophages infected with an oncolytic herpes simplex virus, wherein the monocytes, monocyte derived cells or macrophages contain an exogenous magnetic material, in the manufacture of a medicament for use in a method of treatment of disease is provided, the method comprising administering the medicament to a subject and applying a magnetic field to the subject in order to direct cells of the administered medicament to a desired location in the subject's body.

In another aspect of the present invention a method of treating a disease in a subject in need of treatment is provided, the method comprising administering a preparation comprising a population of monocytes, monocyte derived cells or macrophages infected with an oncolytic herpes simplex virus to said subject, thereby treating said disease. Optionally, the monocytes, monocyte derived cells or macrophages in said population may contain an exogenous magnetic material and the method may optionally further comprise applying a magnetic field to the subject in order to direct cells of the administered preparation to a desired location in the subject's body.

Administration of cells infected with oncolytic Herpes Simplex Virus to a subject may be carried out within a predetermined time from infection with oncolytic Herpes Simplex Virus, and/or the administered cells may be selected to contain a defined percentage range of dead or dying (e.g. lysed) cells, as described herein. The time and/or selection of cells may be such as to ensure that cells are undergoing cell death (e.g. undergoing lysis by the infected oncolytic Herpes Simplex Virus) when they are located in the tissue requiring treatment.

In another aspect of the present invention a kit of parts is provided, the kit comprising a predetermined amount of oncolytic Herpes Simplex Virus and a predetermined amount of a magnetic material. The kit may be provided together with instructions for the infection of monocytes, monocyte derived cells or macrophages with the oncolytic Herpes Simplex Virus and/or for the loading of monocytes, monocyte derived cells or macrophages with the magnetic material. Such instructions may be for carrying out said infection and/or loading ex vivo or in vitro, e.g. under conditions of in vitro cell culture.

In some embodiments all copies of the ICP34.5 gene in the genome of the oncolytic herpes simplex virus are modified such that the ICP34.5 gene is incapable of expressing a functional ICP34.5 gene product. As such the oncolytic herpes simplex virus may be an ICP34.5 null mutant.

In some embodiments one or both of the ICP34.5 genes in the genome of the oncolytic herpes simplex virus are modified such that the ICP34.5 gene is incapable of expressing a functional ICP34.5 gene product.

In some embodiments the oncolytic herpes simplex virus is a mutant of HSV-1 strain 17. In preferred embodiments the oncolytic herpes simplex virus is HSV1716 (ECACC Accession No. V92012803). In some embodiments the herpes simplex virus is a mutant of HSV-1 strain 17 mutant 1716.

In some embodiments the disease to be treated is a cancer, e.g. a tumor. The treatment may be of a hypoxic region of the cancer, which may also be the desired location to which cells are magnetically directed. As such, methods of treatment may involve treatment of a hypoxic region of a cancer, either together with other normoxic regions of the cancer or independent of treatment of normoxic regions of the cancer. The method of treatment may also involve induction of an anti-tumor response in the subject. The method of treatment may also involve applying a magnetic field to the subject in order to direct administered cells containing an exogenous magnetic material to a hypoxic region of the cancer.

Description

The inventors' findings indicate that an oncolytic Herpes Simplex Virus is able to kill monocyte derived cells after 96 hours from infection. Oncolytic Herpes Simplex Virus are generally known to have a highly selective lytic activity towards proliferating cells, in principle permitting tumor treatment by systemic or non-localised administration and self-targeting of tumor cells without harming healthy cells. This affords an exemplary safety profile.

The inventors' have observed that following infection of monocyte derived cells virus is not detected in the infected cells but presence of virus is re-established upon prolonged culture (FIG. 1). This is consistent with productive infection of the cells, i.e. involving replication and cell lysis by viral progeny, although the invention is not bound by such theory. The finding that infection with oncolytic Herpes Simplex Virus leads to cell death of monocyte derived cells means that infected monocytes or monocyte derived cells may be used to deliver the oncolytic Herpes Simplex Virus to the diseased tissue, including to hypoxic areas of a tumor, subsequently allowing the release of virus directly to the diseased tissue as the cell dies.

The inventors also found that oncolytic Herpes Simplex Virus replication in, and subsequent cell death (e.g. lysis) of, monocyte derived cells is actually greater in hypoxic conditions. This indicates that death of the monocyte derived cells occurs (apparently preferentially) in hypoxic tumor environments and will directly release the oncolytic Herpes Simplex Virus to the hypoxic parts of a tumor that are otherwise difficult to access.

Accordingly, to ensure that a substantial number of monocyte or monocyte derived cells will undergo death and viral release when they are present in the target tissue or tumor, administration of infected cells to a subject may be carried out within a predetermined time from infection with oncolytic Herpes Simplex Virus, and/or the administered cells may be selected to contain a defined percentage range of dying or dead (e.g. lysed) cells. The inventors have also shown that monocyte or monocyte derived cells infected with oncolytic Herpes Simplex Virus and loaded with an exogenous magnetic material can be steered from the bloodstream into deep tissue targets (including primary and secondary (metastatic) tumors) by magnetic resonance targeting. By way of example, this may use pulsed magnetic-field gradients within a magnetic resonance (e.g. MRI, MRT) system. Accordingly, systemic administration, e.g. to the blood, coupled with accurate non-invasive direction of the oncolytic Herpes Simplex Virus armed cells directly to the diseased tissue becomes a reality.

This approach has particular application when a tissue or tumor is difficult or impossible to remove surgically, e.g. as in the lung, brain, liver or spinal cord. Additionally, targeting of cells to one or more metastatic lesions in cancer patients is possible using phased administration of cells, coupled with respective independent magnetic resonance sessions to target each administration of cells to independent locations.

In addition to direct action of oncolytic herpes simplex virus (oHSV) on tumors, there is growing evidence that the host immune response plays an important role in establishing the efficacy of the anti-tumor response through innate immune effectors, adaptive antiviral immune responses and adaptive antitumor immune responses (e.g. see Prestwich et al., Onoclytic viruses: a novel form of immunotherapy. Expert Rev Anticancer Ther. October 2008; 8(10): 1581-1588).

Several studies have shown that oHSV is capable of inducing an anti-tumor immune response. This can manifest as tumor growth reduction in lesions treated with oHSV and in untreated lesions in the same animal, efficacy of oHSV requiring an intact immune response, induction of anti-tumor cytokine response, reversal of tumor immune dysfunction and facilitation of tumor antigen presentation. Induction of an anti-tumor immune response can reduce establishment of metastases, or contribute to their elimination, and protect from re-occurrence of tumor.

For example, in Benencia et al., ((2008) Herpes virus oncolytic therapy reverses tumor immune dysfunction and facilitates tumor antigen presentation. Cancer Biol. Ther. 7, 1194-1205) growth reduction in treated and untreated lesions was reported. In Miller and Fraser ((2003) Requirement of an integrated immune response for successful neuroattenuated HSV-1 therapy in an intracranial metastatic melanoma model. Mol. Ther. 7(6):741-747) efficacy of HSV1716 required an intact immune response which was mediated by a tumor-specific proliferative T cell response.

The inventors have shown here that in hypoxic conditions oncolytic Herpes Simplex Virus is an inducer of pro-inflammatory cytokines and transcription factors (e.g., IL-8, IL-1 and NFκB), relative to normoxic conditions. These findings suggest increased inflammatory response properties of oncolytic Herpes Simplex Virus in hypoxic conditions, suggesting that oncolytic Herpes Simplex Virus acquires a greater viral potentiality in hypoxia, further supporting the rationale of using virus delivery by monocytes or monocyte derived cells to target central areas of a tumor that are hypoxic and difficult to access.

Oncolytic Herpes Simplex Virus

An oncolytic virus is a virus that will lyse cancer cells (oncolysis), preferably in a preferential or selective manner. Viruses that selectively replicate in dividing cells over non-dividing cells are often oncolytic. Oncolytic viruses are well known in the art and are reviewed in Molecular Therapy Vol. 18 No. 2 February 2010 pg 233-234.

The herpes simplex virus (HSV) genome comprises two covalently linked segments, designated long (L) and short (S). Each segment contains a unique sequence flanked by a pair of inverted terminal repeat sequences. The long repeat (RL or $R_L$) and the short repeat (RS or $R_S$) are distinct.

The HSV ICP34.5 (also called γ34.5) gene, which has been extensively studied, has been sequenced in HSV-1 strains F and syn17+ and in HSV-2 strain HG52. One copy of the ICP34.5 gene is located within each of the RL repeat regions. Mutants inactivating one or both copies of the ICP34.5 gene are known to lack neurovirulence, i.e. be avirulent/non-neurovirulent (non-neurovirulence is defined by the ability to introduce a high titre of virus (approx $10^6$ plaque forming units (pfu)) to an animal or patient without causing a lethal encephalitis such that the $LD_{50}$ in animals, e.g. mice, or human patients is in the approximate range of $\geq 10^6$ pfu), and be oncolytic.

Preferred oncolytic Herpes Simplex Virus (oHSV) are replication-competent virus, being replication-competent at least in the target tumor/cancer cells.

Oncolytic HSV that may be used in the present invention include HSV in which one or both of the γ34.5 (also called ICP34.5) genes are modified (e.g. by mutation which may be a deletion, insertion, addition or substitution) such that the respective gene is incapable of expressing, e.g. encoding, a functional ICP34.5 protein. Preferably, in HSV according to the invention both copies of the γ34.5 gene are modified such that the modified HSV is not capable of expressing, e.g. producing, a functional ICP34.5 protein.

In some embodiments the oncolytic herpes simplex virus may be an ICP34.5 null mutant where all copies of the ICP34.5 gene present in the herpes simplex virus genome (two copies are normally present) are disrupted such that the herpes simplex virus is incapable of producing a functional ICP34.5 gene product. In other embodiments the oncolytic herpes simplex virus may lack at least one expressible ICP34.5 gene. In some embodiments the herpes simplex virus may lack only one expressible ICP34.5 gene. In other embodiments the herpes simplex virus may lack both expressible ICP34.5 genes. In still other embodiments each ICP34.5 gene present in the herpes simplex virus may not be expressible. Lack of an expressible ICP34.5 gene means, for example, that expression of the ICP34.5 gene does not result in a functional ICP34.5 gene product.

Oncolytic herpes simplex virus may be derived from any HSV including any laboratory strain or clinical isolate (non-laboratory strain) of HSV. In some preferred embodiments the HSV is a mutant of HSV-1 or HSV-2. Alternatively the HSV may be an intertypic recombinant of HSV-1 and HSV-2. The mutant may be of one of laboratory strains HSV-1 strain 17, HSV-1 strain F or HSV-2 strain HG52. The mutant may be of the non-laboratory strain JS-1. Preferably the mutant is a mutant of HSV-1 strain 17. The herpes simplex virus may be one of HSV-1 strain 17 mutant 1716, HSV-1 strain F mutant R3616, HSV-1 strain F mutant G207, HSV-1 mutant NV1020, or a further mutant thereof in which the HSV genome contains additional mutations and/or one or more heterologous nucleotide sequences. Additional mutations may include disabling mutations, which may affect the virulence of the virus or its ability to replicate. For example, mutations may be made in any one or more of ICP6, ICP0, ICP4, ICP27. Preferably, a mutation in one of these genes (optionally in both copies of the gene where appropriate) leads to an inability (or reduction of the ability) of the HSV to express the corresponding functional polypeptide. By way of example, the additional mutation of the HSV genome may be accomplished by addition, deletion, insertion or substitution of nucleotides.

A number of oncolytic herpes simplex viruses are known in the art. Examples include HSV1716, 83616 (e.g. see Chou & Roizman, Proc. Natl. Acad. Sci. Vol. 89, pp. 3266-3270, April 1992), G207 (Toda et al, Human Gene Therapy 9:2177-2185, Oct. 10, 1995), NV1020 (Geevarghese et al, Human Gene Therapy 2010 Sep.; 21(9):1119-28), RE6 (Thompson et al, Virology 131, 171-179 (1983)), and Oncovex™ (Simpson et al, Cancer Res 2006; 66:(9) 4835-4842 May 1, 2006; Liu et al, Gene Therapy (2003): 10, 292-303), dlsptk, hrR3,R4009, MGH-1, MGH-2, G47Δ, Myb34.5, DF3γ34.5, HF10, NV1042, RAMBO, rQNestin34.5, R5111, R-LM113, CEAICP4, CEAγ34.5, DF3γ34.5, KeM34.5 (Manservigi et al, The Open Virology Journal 2010; 4:123-156), rRp450, M032 (Campadelli-Fiume et al, Rev Med. Virol 2011; 21:213-226), Baco1 (Fu et al, Int. J. Cancer 2011; 129(6):1503-10) and M032 and C134 (Cassady et al, The Open Virology Journal 2010; 4:103-108).

In some preferred embodiments the herpes simplex virus is HSV-1 strain 17 mutant 1716 (HSV1716). HSV 1716 is an oncolytic, non-neurovirulent HSV and is described in EP 0571410, WO 92/13943, Brown et al (Journal of General Virology (1994), 75, 2367-2377) and MacLean et al (Journal of General Virology (1991), 72, 631-639). HSV 1716 has been deposited on 28 January 1992 at the European Collection of Animal Cell Cultures, Vaccine Research and Production Laboratories, Public Health Laboratory Services, Porton Down, Salisbury, Wiltshire, SP4 OJG, United Kingdom under accession number V92012803 in accordance with the provisions of the Budapest Treaty on the International Recognition of the Deposit of Microorganisms for the Purposes of Patent Procedure (herein referred to as the 'Budapest Treaty').

In some embodiments the herpes simplex virus is a mutant of HSV-1 strain 17 modified such that both ICP34.5 genes do not express a functional gene product, e.g. by mutation (e.g. insertion, deletion, addition, substitution) of the ICP34.5 gene, but otherwise resembling or substantially resembling the genome of the wild type parent virus HSV-1 strain 17+. That is, the virus may be a variant of HSV1716, having a genome mutated so as to inactivate both copies of the ICP34.5 gene of HSV-1 strain 17+ but not otherwise altered to insert or delete/modify other protein coding sequences.

In some embodiments the genome of an oncolytic Herpes Simplex Virus according to the present invention may be further modified to contain nucleic acid encoding at least one copy of a polypeptide that is heterologous to the virus (i.e. is not normally found in wild type virus) such that the polypeptide can be expressed from the nucleic acid. As such, the oncolytic virus may also be an expression vector from which the polypeptide may be expressed. Examples of such viruses are described in WO2005/049846 and WO2005/049845.

In order to effect expression of the polypeptide, nucleic acid encoding the polypeptide is preferably operably linked to a regulatory sequence, e.g. a promoter, capable of effecting transcription of the nucleic acid encoding the polypeptide. A regulatory sequence (e.g. promoter) that is operably linked to a nucleotide sequence may be located adjacent to that sequence or in close proximity such that the regulatory sequence can effect and/or control expression of a product of the nucleotide sequence. The encoded product of the nucleotide sequence may therefore be expressible from that regulatory sequence.

In some preferred embodiments, the oncolytic Herpes Simplex Virus is not modified to contain nucleic acid encoding at least one copy of a polypeptide (or other nucleic acid encoded product) that is heterologous to the virus. That is the virus is not an expression vector from which a heterologous polypeptide or other nucleic acid encoded product may be expressed. Such oHSV are not suitable for, or useful in, gene therapy methods and the method of medical treatment for which they are employed may optionally be one that does not involve gene therapy.

Monocyte, Monocyte Derived Cell or Macrophage

Monocytes are a type of leukocyte (white blood cell) produced by the bone marrow. Following initial circulation in the blood they normally move into tissues where they differentiate into macrophages or dendritic cells. Monocytes and their macrophage and dendritic cell progeny are involved in phagocytosis, antigen presentation and cytokine production.

Phagocytosis involves the uptake (ingestion) of matter (e.g. microbial or particulate matter or, in some instances, of nutrients) into the cell followed by digestion and/or destruction of the matter within the cell. Phagocytosis is a specialised form of endocytosis. The process of phagocytosis usually involves engulfing the matter in a membrane bound vesicle (the phagosome) which is internalised into the cell. The phagosome may then fuse with a lysosome to form a phagolysosome in which digestion of the matter may occur.

Considering the role of monocytes and their progeny in the innate immune system, phagocytosis plays a major role in the removal of pathogens and cell debris.

Monocytes or monocyte derived cells may be isolated from peripheral blood or other tissues (e.g. see de Almeida et al (A Simple Method for Human Peripheral Blood Monocyte Isolation. Mem Inst Oswaldo Cruz, Rio de Janeiro, Vol. 95(2): 221-223, March/April 2000); Elkord et al (Human monocyte isolation methods influence cytokine production from in vitro generated dendritic cells. Immunology. February 2005; 114(2):204-212); Repnik et al (Simple and cost-effective isolation of monocytes from buffy coats. Journal of Immunological Methods Vol. 278, Issues 1-2, July 2003, pages 283-292); Zhang et al (The Isolation and Characterization of Murine Macrophages. Curr. Protoc. Immunol. 83:14.1.1-14.1.14. 2008); John Q. Davies and Siamon Gordon (The Isolation and Culture of Human Macrophages. Basic Cell Culture Protocols Methods in Molecular Biology Vol 290, 2005, pp105-116).

Macrophages are mononuclear phagocytes that are widely distributed throughout the body, where they participate in innate and adaptive immune responses. The physiology of macrophages can vary depending on the tissue environment in which they reside and the local stimuli to which they are exposed. As such a range of different tissue-specific macrophages can be identified, e.g. adipose tissue macrophages from adipose tissue, monocytes from blood or bone marrow, Kupffer cells from liver. Macrophages are secretory cells, and can promote and regulate immune responses by secretion of cytokines and chemokines. Human macrophages can be isolated by flow cytometry in view of their specific expression of proteins such as CD14, CD40, Cd11b and CD64. Macrophages can be isolated from other mammals, e.g. mice or other rodents, by similar techniques. For reviews of monocytes and macrophages see Nature Reviews Immunology, 11, (2011).

Monocytes and their progeny such as macrophages are attracted to hypoxic tissue (tissue having a low oxygen tension), which is a hallmark feature of mammalian and experimental tumors, often because of limited tumor vascularisation. Monocytes are continually recruited into tumors where they accumulate and differentiate into tumor associated macrophages (TAMs). TAMs are abundant in solid and haemotological malignancies and have been linked with progression, metastasis and resistance to therapy (Cook and Hagemann. Tumor-associated macrophages and cancer. Current Opinion in Pharmacology, Vol. 12, Issue 4, August 2013, pages 595-601). Studies have shown that macrophages respond to levels of hypoxia found in tumors by up-regulating hypoxia inducible transcription factors which activate a broad range of mitogenic, proinvasive, proangiogenic and prometastatic genes (Lewis and Murdoch. Macrophage Responses to Hypoxia, Implications for Tumor progression and Anti-Cancer Therapies. Am J Pathol. September 2005; 167(3): 627-635).

The present invention is concerned with monocytes, or monocyte derived cells such as macrophages or dendritic cells capable of being infected with an oncolytic Herpes Simplex Virus, and optionally capable of uptaking an exogenous magnetic material, e.g. by phagocytosis, to produce a cell that is 'loaded' with the magnetic material. The cells may be non-human, preferably mammalian e.g. rabbit, guinea pig, rat, mouse or other rodent (including cells from any animal in the order Rodentia), cat, dog, pig, sheep, goat, cattle, horse, non-human primate, or may be human cells. In some embodiments it is preferred that the cell is a macrophage, e.g. a human or mammalian macrophage.

The monocyte or monocyte derived cell may be isolated or obtained from a subject to be treated, e.g. by isolation from a sample of peripheral blood as described above. Alternatively, it may be isolated or obtained from a donor subject, e.g. another mammal or human (preferably of the same species). Donor monocytes may be screened for immunocompatibility. Monocytes or monocyte derived cells may be isolated from other cell types to provide a culture or preparation that is substantially free of cells that are not monocytes or monocyte derived cells. Optionally, suitable support or feeder cells may be present in the culture or preparation.

The isolated cells may be cultured in vitro where they may be infected with the oncolytic Herpes Simplex Virus and loaded with the magnetic material.

Infection of monocytes or monocyte derived cells refers to contacting the cells with oncolytic Herpes Simplex Virus under conditions and for a sufficient amount of time suitable to allow the Herpes Simplex Virus to enter the cells. Such infection may preferably be performed under conditions of in vitro cell culture. Techniques for the in vitro infection of human and mammalian cells are known to those of ordinary skill in the art, e.g. see Szántó et al. Peristent infection of BHK cells with herpes simplex virus types 1 and 2 in the absence of specific anti-herpetic antibody. Acta Virol. 1976 February; 20(1); 40-7); Conner et al. Herpes simplex virus type 1 strain HSV1716 grown in baby hamster kidney cells has altered tropism for non-permissive Chinese hamster ovary cells compared to HSV1716 grown in vero cells. J Virol. 2005 August; 79(15):9970-81. Techniques for the in vitro culture of macrophages are also known to those of ordinary skill in the art, e.g. see John Q. Davies and Siamon Gordon (The Isolation and Culture of Human Macrophages. Basic Cell Culture Protocols Methods in Molecular Biology Vol. 290, 2005, pp105-116).

Accordingly, methods of preparing a monocyte, monocyte derived cell or macrophage infected with an oncolytic herpes simplex virus, may comprise contacting one or a plurality (optionally a population) of monocytes, monocyte derived cells or macrophages with a quantity of oncolytic herpes simplex virus under suitable conditions, e.g. of in vitro cell culture, and for sufficient time to permit productive infection of the monocytes, monocyte derived cells or macrophages.

Optionally, the cells may be maintained in culture under conditions in which the virus is able to induce cell death. Although not wishing to be bound by theory, the inventors believe that following infection of a monocyte, monocyte derived cell or macrophage oncolytic herpes simplex undergoes replication and viral progeny subsequently lyse the cells, causing cell death. As such, the culture conditions and duration may be suitable to produce a culture having a mixture of intact and dead, e.g. lysed, monocytes, monocyte derived cells or macrophages.

Cells may be contacted with a virus so as to achieve a multiplicity of infection (MOI) in the range 0.5-100, optionally one of 0.5-5, 1-10, 10-20, 20-30, 30-40, 40-50, 50-60, 60-70, 70-80, 80-90, 90-100, 1-30, 5-30, 5-50, or 30-50.

Optionally, cells may be administered to a subject within a predetermined time from infection. This may be to ensure that death (e.g. lysis) of cells occurs in the target tissue or tumor, allowing dissemination and spread of virus in the target tissue. As such, administration of cells may be within 1 hour, 2 hours, 3 hours, 6 hours, 12 hours, 18 hours, 24 hours, 30 hours, 36 hours, 42 hours, 48 hours, 3 days, 4 days, 5 days, 6 days or 7 days, 8 days, 9 days, 10 days, 11 days, 12 days, 13 days, or 14 days of infection.

Loading of monocytes or monocyte derived cells with magnetic material may also be performed under in vitro culture conditions and this step may be performed prior to, together with, or after infection of the cells with the oncolytic Herpes Simplex Virus. Techniques for loading monocytes or monocyte derived cells with magnetic material are, for example, described in Kaim et al. MR imagaing with ultrasmall superparamagentic iron oxide particles in experimental soft-tissue infections in rats. Radiology 2002 December; 225(3):808-14, and in Muthana et al. A novel magnetic approach to enhance the efficacy of cell-based gene therapies. Gene Therapy (2008) 15, 902-910). Cells may be loaded with magnetic material by contacting the cells with a suspension of magnetic particles having a concentration of particles of about 20 to 300 µg/ml, or one of about 50 to 150 µg/ml, 75 to 125 µg/ml, 90 to 110 µg/ml or about 100 µg/ml.

Accordingly, methods of preparing a monocyte, monocyte derived cell or macrophage may comprise, in addition to infection with an oncolytic herpes simplex virus, the step of contacting the cells with a quantity of magnetic material under suitable conditions, e.g. of in vitro cell culture, and for sufficient time to permit uptake, e.g. by phagocytosis, of magnetic material into monocytes, monocyte derived cells or macrophages.

Following infection and/or uptake of magnetic material, cells may be further cultured for as long as is desired, collected, isolated, purified or separated and formulated into a suitable preparation.

The monocytes, monocyte derived cells or macrophages described herein may be formulated as preparations, e.g. pharmaceutical compositions or medicaments for clinical use and in such formulations may be combined with a pharmaceutically acceptable carrier, diluent or adjuvant. A method of formulating or producing a preparation may comprise mixing the selected cells, with a pharmaceutically acceptable carrier, adjuvant, diluent or buffer.

A preparation may comprise a population of monocytes, monocyte derived cells or macrophages meaning that the preparation is made up of a plurality of said cells having common characteristics, e.g. monocyte, monocyte derived cells or macrophages infected with an oncolytic Herpes Simplex Virus, and optionally containing an exogenous magnetic material. The preparation may take any form, as described herein. Purely by way of example, the preparation may be a pharmaceutical composition or medicament comprising the population of cells together with a pharmaceutically acceptable carrier, adjuvant, diluent or buffer.

By way of example, the preparation may be formulated for parenteral, systemic, intracavitary, intravenous, intra-arterial or intratumoral routes of administration which may include injection or delivery by catheter. Suitable formulations may comprise the cells in a sterile or isotonic medium. Medicaments and pharmaceutical compositions may be formulated in fluid form suitable for injection, e.g. as a liquid, solution, suspension, or emulsion, or may be formulated as a depot or reservoir, e.g. suitable for implantation in the subject's body, from which the rate of release of the cells may be controlled. Depot formulations may include gels, pastes, boluses or capsules. The preparation may be provided in a suitable container or packaging. Fluid formulations may be formulated for administration by injection or via catheter to a selected region of the human or animal body.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation. Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

A population of cells refers to a plurality of cells having common characteristics, e.g. monocyte, monocyte derived cells or macrophages infected with an oncolytic Herpes Simplex Virus, and optionally containing an exogenous magnetic material. In some embodiments the population will contain approximately several hundred cells or more of a given type i.e. of monocytes, monocyte derived cells or macrophages. The population may have several thousand cells or more of the given type or a number of cells of the approximate order $1 \times 10^4$, $1 \times 10^5$, $1 \times 10^6$, $1 \times 10^7$ or more. A population may exist in, or be isolated from, an in vitro culture of cells, or may exist in a preparation of cells, e.g. in a pharmaceutical composition or medicament.

The population of cells may refer to all cells, or substantially all cells, in a culture or preparation being of the given type, i.e. all cells, or substantially all cells, in the culture or preparation being monocytes, monocyte derived cells or macrophages. In some embodiments a preparation or culture of cells may contain other types of cell, e.g. feeder cells or fibroblasts, which may optionally not be considered part of the population. In some embodiments it is preferred that in a population of cells at least 80% of the cells are monocytes, monocyte derived cells or macrophages. In some embodiments this percentage may be one of 81, 82, 83, 84, 85, 86, 87, 88, 89, 90, 91, 92, 93, 94, 95, 96, 97, 98, 99 or 100%.

Preferably, in a population of cells at least 80%, or one of 81, 82, 83, 84, 85, 86, 87, 88, 89, 90, 91, 92, 93, 94, 95, 96, 97, 98, 99 or 100% of the monocytes, monocyte derived cells or macrophages in the population are infected with the oHSV, and optionally also contain an exogenous magnetic material. In some preferred embodiments substantially all, e.g. 95% or more, of the monocytes, monocyte derived cells or macrophages in the population are infected with the oHSV and optionally also contain an exogenous magnetic material.

In a population of cells, some of the monocytes, monocyte derived cells or macrophages that are infected with oHSV may have undergone cell death (e.g. lysed by the oHSV). Dying or dead (e.g. lysed) cells may account for 1-50% of the monocytes, monocyte derived cells or macrophages that are infected with oHSV or of the population of monocytes, monocyte derived cells or macrophages. In some embodiments this range may be one of 0.5%-5%, 1-5%, 1-10%, 1-20%, 10-20%, 10-30%, 20-40% or 30-50%. This may be the percentage of dying or dead (e.g. lysed) cells in a population at the time of administration to a subject.

In some preferred embodiments, the monocyte, monocyte derived cell or macrophage is not modified to contain nucleic acid encoding at least one copy of a polypeptide (or other nucleic acid encoded product) that is heterologous to the cell. That is the cell is not modified to express the heterologous polypeptide or other nucleic acid encoded product. Such cells are not suitable for, or useful in, gene therapy methods and the method of medical treatment for which they are employed may optionally be one that does not involve gene therapy (i.e. a medical method or treatment reliant on expression of an heterologous polypeptide or other nucleic acid encoded product).

Optionally, and as described elsewhere herein, the oHSV with which the monocyte, monocyte derived cell or macrophage is infected may also be one that is not modified to contain a nucleic acid encoding a polypeptide (or other nucleic acid encoded product) that is heterologous to the virus and as such is also not suitable for, or useful in, gene therapy methods, and the method of medical treatment for which they are employed may optionally be one that does not involve gene therapy.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

In some embodiments replication or proliferation of the oncolytic Herpes Simplex Virus is not responsive to an hypoxic environment. That is, the oncolytic Herpes Simplex Virus is not modified (or further modified), relative to the wild type virus or to a parental oncolytic virus (e.g. HSV1716), so as to become responsive to an hypoxic environment. For example, viral replication and/or gene expression is not under the control of one or more regulatory elements, e.g. promoter(s), that are responsive (e.g. activated or repressed) to hypoxia in the infected cell or surrounding tissue.

In some embodiments the oncolytic Herpes Simplex Virus is not modified (or further modified), relative to the wild type virus or to a parental oncolytic virus (e.g. HSV1716), so as to replicate or proliferate in specific tissue types, including tumor tissue. For example, viral replication and/or gene expression is not under the control of one or more regulatory elements, e.g. promoter(s), that respond (e.g. are activated or repressed), to location in a specific tissue. For example, viral replication and/or gene expression is not placed under the control of one or more tissue specific or tumor specific promoters (or other regulatory elements).

Infection of Monocytes, Monocyte Derived Cells or Macrophages Induces Formation of a Distinct Population of Cells Gene expression analysis of macrophages infected with oncolytic Herpes Simplex Virus indicates that following infection the cells undergo a change in expression of certain factors, including some pro-inflammatory cytokines, such as IL-6, IL-8, TNF-α, IL-1, CXCL-1, some anti-inflammatory cytokines, such as IL-10, CXCL-6 and other factors, such as NFκB, VEGF-A, and TGF-β.

As such, infection with oncolytic Herpes Simplex Virus leads to formation of a distinct population of cells characterised as being monocytes, monocyte derived cells or macrophages having a distinct pattern of expression of certain genes/proteins. The cells may further be characterised by the conditions of culture or formulation, i.e. normoxic (about 18 to 22% $pO_2$) or hypoxic (less than 5% $pO_2$ and preferably 0.1 to 3% $pO_2$). The cells may be provided as an in vitro or ex vivo preparation of cells, optionally isolated or purified, and may be cells maintained in culture or in a formulation under respective normoxic or hypoxic conditions.

In some embodiments, compared to uninfected cells of the same type, expression of one or more of the pro-inflammatory cytokines IL-6, IL-8, TNF-α, IL-1, CXCL-1 may be upregulated. Such upregulation may preferably occur when the cells are in hypoxic conditions (e.g. about 0.1% $pO_2$). Upregulation of IL-8 and/or IL-1 may be at least 2-fold, optionally 3-fold, or 5-fold. Upregulation of NFκB or TGF-β or CXCL6 expression may also be observed under hypoxic conditions. Upregulation of NFκB and other factors may be consistent with induction of a type 1 T cell response (Th1 and/or Tc1), which is desirable for the treatment of cancers and may be additive to an anti-virus Th1 type immune response initiated in the subject when viral particles are released from the cells.

In some embodiments, compared to uninfected cells of the same type, expression of one or more of IL-8, IL-1, NFκB, IL-10, and VEGFA may be upregulated. Such upregulation may preferably occur when the cells are in hypoxic conditions (e.g. less than 5% $pO_2$ and preferably 0.1 to 3% $pO_2$). Such upregulation may be at least 2-fold, optionally 3-fold, or 5-fold, or more.

In some embodiments, compared to uninfected cells of the same type, expression of one or more of the anti-inflammatory cytokines IL-10, CXCL-6 may be down regulated. Such down regulation may occur when the cells are in normoxic conditions.

In some embodiments, under normoxic conditions one or more of IL-6, IL-8, TNF-α, IL-1, and VEGFA may be upregulated and one or more of NFκB, TGF-β, IL-10, CXCL6 and CXCL1 may be down regulated.

In some embodiments, under hypoxic conditions one or more of IL-6, IL-8, TNF-α, IL-1, NFκB, TGF-β, IL-10, VEGFA, CXCL6 and CXCL1 may be upregulated.

Upregulation or over-expression of a gene/protein comprises expression of the marker at a level that is greater than would normally be expected for a cell or tissue of a given type. As such, upregulation may be determined by comparing the level of expression between virus infected and non-infected cells of the same type.

Levels of expression may be quantitated for absolute comparison, or relative comparisons may be made. Expression may be determined by measuring gene expression, e.g. by measurement of mRNA levels, or by measuring protein expression.

In some embodiments upregulation may be considered to be present when the level of expression in the test sample is at least 1.1 times that in the control sample. In some embodiments the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that in the control sample.

Down regulation may be determined in a corresponding manner, e.g. in some embodiments down regulation may be considered to be present when the level of expression in the test sample is less than 0.9 times that in the control sample. In some embodiments the level of expression may be selected from one of less than 0.8, less than 0.7, less than 0.6, less than 0.5, less than 0.4, less than 0.3, less than 0.2, or less than 0.1 times that in the control sample.

Accordingly, the infected cells represent a distinct and identifiable population of cells, which may be useful in methods of adoptive immunotherapy (e.g. as described in Darcy et al., Current Opinion in Immunology 2014, 27:46-52 and in Andreesen et al., Journal of Leukocyte Biology Volume 64, October 1998, p 419-426) in which the cell provides a therapeutic effect through its expression and/or secretion of defined factors or cytokines which promote an immune response in the subject's body, preferably an anti-tumor response. This action of the cell population is additional to its ability to transport oncolytic Herpes Simplex Virus to diseased tissue and release it in the tissue leading to a separate virus-mediated anti-tumor response.

Accordingly, in one aspect of the present invention a method is provided, the method comprising obtaining a blood or tissue sample from a subject, separating monocyte, monocyte derived cells or macrophages from said blood or tissue sample, infecting said cells with an oncolytic Herpes Simplex Virus, formulating a preparation comprising said infected cells and administering said preparation to said subject. The method may be part of a method of adoptive immunotherapy.

Magnetic Material

A magnetic material can include a material that is magnetically susceptible, a magnetisable material or a material that can be manipulated (e.g. moved) and/or positioned by a magnetic field. The magnetic material can be non-magnetic but susceptible to manipulation or positioning by a magnetic field, or be magnetic (e.g. a source of a magnetic field lines). As such, the magnetic material may be inherently magnetic or one which reacts, e.g. moves, in a magnetic field.

In preferred embodiments the magnetic material is a magnetically susceptible particle or is a fluid, e.g. a fluid in which magnetically susceptible particles are in suspension, often called a ferrofluid, Magnetically susceptible particles can include magnetically susceptible particles, magnetisable particles or particles that can be manipulated (e.g. moved) and/or positioned by a magnetic field. The magnetically susceptible particles can be non-magnetic but susceptible to manipulation or positioning by a magnetic field, or be magnetic (e.g. a source of a magnetic field lines).

Typically the particles are of a size suitable to deliver the reagent into the cell without causing damage to the cell. In one aspect, the particles have a mean size of between 10 µm and 5 nm, such as between 1 µm and 10 nm, for example between 200 nm and 20 nm or between 5 nm and 50 nm. In another aspect the magnetically susceptible particles may be spherical beads and may have a diameter of at least about 0.05 µm, at least about 1 µm, at least about 2.5 µm, and typically less than about 20 µm, or may have a diameter of about 5 to 50 nm, 10 to 40 nm, 20 to 30 nm or about 25 nm.

Not wishing to be limited by theory, it is believed that larger particles will give improved uptake into monocytes, monocyte derived cells or macrophages. For example, magnetite particles >30 nm will experience a torque in an oscillating magnetic field as dictated by the formula $T=\mu B \sin \theta$, where T is the torque, µ is the magnetic moment, B is the magnetic flux density and θ is the angle between the applied field and the particle's magnetization vector. For example, the precise amount of torque is influenced by the particle shape. The movement of the particle induced by this torque is believed to 'drag' the particle into and across the surface of the cell, inducing uptake of the particle by an endocytic mechanism. The uptake of the particle by normal cellular processes means that there is no mechanical damage to the cell (as compared to, for example, biolistic methods or electroporation), thus improving the rate of cellular survival post particle delivery.

A magnetically susceptible particle can be, for example, a magnetically susceptible particle described, in U.S. Patent Application Publication Nos. 20050147963 or 20050100930, or U.S. Pat. No. 5,348,876, each of which is incorporated by reference in its entirety, or commercially available beads, for example, those produced by Dynal AS (Invitrogen Corporation, Carlsbad, Calif. USA) under the trade name DYNABEADS™ and/or MYONE™. In particular, antibodies linked to magnetically susceptible particles are described in, for example, United States Patent Application Nos. 20050149169, 20050148096, 20050142549, 20050074748, 20050148096, 20050106652, and 20050100930, and U.S. Pat. No. 5,348,876, each of which is incorporated by reference in its entirety.

In one aspect the particle comprises a paramagnetic, superparamagnetic, ferromagnetic and/or antiferromagnetic material, such as elemental iron, chromium, manganese, cobalt, nickel, or a compound and/or a combination thereof (e.g. manganese and cobalt ferrites). A particle may be a super-paramagnetic iron oxide (SPIO) particle. For example, suitable compounds include iron salts such as iron oxide, magnetite ($Fe_3O_4$), maghemite ($\gamma Fe_2O_3$), greigite ($Fe_3S_4$) and chromium dioxide ($CrO_2$).

The particles may comprise the magnetic material embedded in a polymer, for example within the pores of a polymer matrix. Alternatively, the particles may comprise a magnetic core surrounded by a biocompatible coating, for example silica or a polymer such as dextran, polyvinyl alcohol or polyethylenimine.

The magnetically susceptible particle may comprise a reagent. The reagent may be associated with (e.g. conjugated to) the particle by covalent or non-covalent bonds (for example, hydrogen bonding, electrostatic interactions, ionic bonding, lipophillic interactions or van der Waals forces). In one aspect the reagent and particle are covalently linked, for example by exposing the reagent to particles bearing reactive side chains, for example benzidine for linking to the tyrosine residues of proteinaceous reagent, or periodate for linking to carbohydrate groups. In another aspect the particle may be linked to a molecule with binding activity (e.g. avidin) and the reagent may be linked to a ligand of said binding molecule (e.g. biotin). This enables the particle and reagent to be easily conjugated in vitro. In a further aspect the particle may comprise the reagent absorbed into a matrix, such as a polymer matrix.

The magnetic material is preferably exogenous to the monocyte, monocyte derived cell or macrophage, i.e. originating outside of the monocyte, monocyte derived cell or macrophage and optionally not being a material that is normally present in a monocyte, monocyte derived cell or macrophage.

Application of a Magnetic Field

In embodiments where monocytes, monocyte derived cells or macrophages are loaded with an exogenous magnetic material, following administration of the monocytes, monocyte derived cells or macrophages to a subject a magnetic field may be applied to the subject in order to direct the administered cells to a desired location in the subject's body, e.g. to a tumor. The cells are thereby subjected to a magnetic force, being the force that is exerted on the magnetic material when it is in a magnetic field having a gradient. The magnetic force may cause the magnetic material to move toward the source of the magnetic field. The magnetic force may also cause the particle to experience a torque. In some arrangements, the magnetic force may cause the particle to move away from the source of the magnetic field. This can occur if the particle is magnetically blocked and unable to rotate.

As used herein, the 'force field' of a magnet, or of a magnet array, describes the volume of space surrounding the magnet or magnet array in which a magnetic material will experience a magnetic force.

The magnetic field may be provided by a magnet field source, typically a magnet, or array of magnets. The magnet may be an electromagnet. The type and size/power of magnet selected will depend on the application. For example, where cells are administered locally to tumor near the surface of the body, e.g. a primary melanoma, a handheld magnet may be sufficient to apply a suitable magnetic force to direct the cells, e.g. through tissue or blood vessels, toward the site of the tumor. In other instances, for example where the tumor is located deeper within the body and/or where administration is non-local to the tumor, e.g. systemic administration, the subject may be placed in a variable or oscillating, and preferably controllable, magnetic field, such as that of an electromagnet or that provided by a magnetic resonance imaging (MRI), nuclear magnetic resonance imaging (NMRI) or magnetic resonance topography (MRT) apparatus.

In some preferred embodiments methods and uses according to the present invention involve the direction or targeting of monocytes, monocyte derived cells or macrophages loaded with a magnetic material to a selected tissue or tumor that is not located near the skin, i.e. to a deep tissue or organ. A deep tissue or organ may be one that is at least 4 cm or 5 cm or more away from the surface of the skin (measured as shortest distance to the surface of the skin from the centre of the region of the tissue or tumor to be treated). The tissue or tumor may be in the core of the subject's body (i.e. the part of the body that does not include the legs and arms). The tissue or tumor may be in the head, neck, thorax, abdomen, or pelvis. The tissue or tumor may be one of the major organs, or in one of the major organs, such as the adrenal gland, adrenal medulla, anus, appendix, bladder, bone, bone marrow, brain, breast, cecum, central nervous system (including or excluding the brain) cerebellum, cervix, colon, duodenum, endometrium, gallbladder, oesophagus, heart, ileum, intestines, jejunum, kidney(s), lacrimal glad, larynx, liver, lung(s), lymph, lymph node, mediastinum, mesentery, myometrium, nasopharynx, omentume, ovary, pancreas, parotid gland, peripheral nervous system, peritoneum, pleura, prostate, rectum, salivary gland, sigmoid colon, small intestine, spleen, stomach, testis, thymus, thyroid gland, or uterus. The monocytes, monocyte derived cells or macrophages may be directed or targeted to a region of a tissue or tumor that is hypoxic.

To effect treatment, the subject may be administered cells loaded with the magnetic material, and be positioned within a magnetic field. The magnetic field may then be varied or otherwise manipulated relative to the subject and/or to the cells so as to apply a magnetic force to the magnetic material contained within the cells, directing the magnetic material (and cells) toward a desired location in the subject's body, taking account as necessary of the architecture of the tissue, e.g. blood vasculature, to which the cells were administered.

Apparatus and techniques for magnetically guiding and/or localising cells loaded with a magnetic material, and other agents, to a target site within the body (sometimes called Magnetofection) are known to those of ordinary skill in the art, and are described, by way of example, in Muthana et al., (A novel magnetic approach to enhance the efficacy of cell-based gene therapies. Gene Therapy (2008) 15, 902-910); Polyak and Friedman, (Magnetic targeting for site-specific drug delivery: applications and clinical potential. Expert Opinion on Drug Delivery, January 2009, Vol. 6, No. 1: Pages 53-70); Plank et al., (Magnetically enhanced nucleic acid delivery. Ten years of magnetofection—Progress and prospects. Advanced Drug Delivery Reviews. Vol. 63, Issues 14-15, November 2011, pages 1300-1331); and in Li et al., (Targeting Cancer Gene Therapy with Magnetic Nanoparticles Oncotarget. April 2012; 3(4):365-370).

In preferred embodiments, the application of a magnetic field to the body of a subject is non-invasive and non-surgical. The magnetic field source is normally external to the subject's body and in preferred embodiments does not physically contact the subject's body.

Cancer

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentume, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In some embodiments the cancer may be a solid tumor.

Hypoxia

In some embodiments, a tissue or cancer may be one that has a hypoxic environment and treatment may be directed to cells within that environment, either together with surrounding normoxic cells or independent of them.

Physiological normoxia varies between tissues, between animals and between individuals. A tissue or organ may have variable measurements, for example depending on the pattern of vascularisation. In general, healthy mammalian internal tissues and organs will typically have a mean average partial pressure of oxygen greater than 20 mmHg [about 2.62% oxygen] (e.g. about >35 mmHg in brain, >50 mmHg in intestinal tissue, >35 mmHg in liver, >25 mmHg in muscle)

Techniques for measurement of physiological normoxia and hypoxia in live subjects are described in Carreau et al., (J. Cell. Mol. Med. Vol. 15, No. 6, 2011 pp. 1239-1253), incorporated herein by reference. These include non-invasive and invasive techniques. Non-invasive techniques include imaging techniques such as positron emission tomography (PET), magnetic resonance spectroscopy (MRS, e.g. $^{19}$F-MRI, blood oxygen dependent-MRI, or dynamic contrast-enhanced MRI), near-infrared spectroscopy (NIRS), and electron paramagnetic resonance spectroscopy (EPR), optionally in conjunction with a hypoxia marker such as a nitroimidazole (e.g. azomycin). Other techniques include use of a polarographic sensor (often considered the gold standard for measuring oxygen tension), an optical fibre-based sensor in conjunction with a $pO_2$ sensitive fluorescent dye such as ruthenium chloride, and mass spectrometry.

In some embodiments a method of treatment may comprise measuring or determining the state of normoxia and/or hypoxia in a tissue in a subject, e.g. measurement of oxygen partial pressure, and selecting the subject and/or a tissue or part of a tissue in the subject, for treatment with a monocyte, monocyte derived cell or macrophage infected with an oncolytic herpes simplex virus. In embodiments where the cells contain an exogenous magnetic material and the determination of the state of normoxia/hypoxia is made using a magnetic resonance method both determination of the state of normoxia/hypoxia and direction of cells towards the selected tissue or part of tissue may optionally be performed simultaneously.

Hypoxia is known to occur in tumors. Rapid growth of the tumor without corresponding angiogenesis or neovascularisation leads to regions of the tumor in which the oxygen concentration is lower than in normal (normoxic) healthy tissues. As such, hypoxic microenvironments develop and the metabolism of the tumor cells may become adapted to the hypoxic environment. Tumor hypoxia is reviewed in Kizaka-Kondoh et al., (Tumor hypoxia: A target for selective cancer therapy. Cancer Sci December 2003, vol. 94, no. 12, 1021-1028) and Höckel and Vaupel (Journal of the National Cancer Institute Vol. 93, No. 4, Feb. 21, 2001, p 266-276), each of which are specifically incorporated by reference herein.

Tumor hypoxia is common in solid tumors. Many solid tumors contain areas of low $O_2$ partial pressure that cannot be predicted by clinical size, stage, grade or histology. In some embodiments hypoxia may be defined by a partial pressure of oxygen of one of less than about 20 mmHg, less than about 15 mmHg, less than about 14 mmHg, less than about 13 mmHg, less than about 12 mmHg, less than about 11 mmHg, less than about 10 mmHg, less than about 9 mmHg, less than about 8 mmHg, less than about 7 mmHg, less than about 6 mmHg, less than about 5 mmHg, less than about 4 mmHg, less than about 3 mmHg, less than about 2 mmHg, or less than about 1 mmHg. In some embodiments hypoxia may be defined as tissue having a partial pressure of oxygen in the range 0.01 to 15 mmHg, 5 to 15 mmHg, 0.01 to 10 mmHg, 3 to 10 mmHg, 5 to 10 mmHg, 7 to 10 mmHg, 8 to 10 mmHg, 8 to 11 mmHg, or 7 to 12 mmHg. In some embodiments hypoxia may be defined as tissue having a partial pressure of oxygen of one of about 1, 2, 3, 4, 5, 6, 7, 8, 9, 10, 11, or 12 mmHg. [Note: 1 mmHg=133.322 Pa; 1% oxygen=1.013 kPa or about 7.64 mmHg]

As cellular metabolism may be adapted in hypoxic conditions, hypoxia may also be determined by measuring expression of one or more markers.

Such markers include transcription factors, e.g. NFκB or one of the hypoxia inducible factor (HIF) family, e.g. the isoforms HIF-1a, HIF-2α. HIF-1 has two subunits, HIF-1α and HIF-1β. HIF-1α and HIF-2α are induced within minutes of occurrence of hypoxia. HIF-1α is primarily an acute response to hypoxia and HIF-1α levels tend to reduce in prolonged hypoxia. HIF-2α levels tend to continue to increase with time in hypoxia. Induction of HIF-1α normally requires a lower $pO_2$ (<5% [Carreau et al]) than is required for induction of HIF-2α. As such, in some embodiments hypoxia may be determined by measuring upregulation of expression of NFκB, HIF-1α or HIF-2α, which measurement may be compared to a corresponding tissue considered to be at physiological normoxia.

Another group of markers are the hypoxia regulated microRNAs (HRMs), which include miR-21, 23a, 23b, 24, 26a, 26b, 27a, 30b, 93, 103, 106a, 107, 125b, 181a, 181b, 192, 195, 210 and 213, which may be upregulated in hypoxic cells. Some microRNAs may be down-regulated in hypoxic cells, such as miR-15b, 16, 19a, 20a, 20b, 29b, 30b, 30e-5p, 101, 141, 122a, 186, 197, 320. As such, in some embodiments hypoxia may be determined by measuring upregulation, or downregulation, of one or more hypoxia regulated microRNAs. Measurement may be compared to a tissue considered to be at physiological normoxia.

Hypoxia may induce proteome changes, which in the case of tumor hypoxia may promote tumor propagation and adaptation to the hypoxic environment. Such adaptation may involve adapting to nutritional deprivation, e.g. by stimulating transcription of glycolytic enzymes, glucose transporters (e.g. GLUT1 and GLUT3), angiogenic molecules, survival and growth factors (e.g. VEGF), angiogenin, PDGF-β, or TGF-β.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a cancer, or be suspected of having a cancer.

Kits

In some aspects of the present invention a kit of parts is provided. In some embodiments the kit may have at least one container having a predetermined quantity of oncolytic Herpes Simplex Virus, e.g. predetermined viral dose or number/quantity/concentration of viral particles. The oncolytic Herpes Simplex Virus may be formulated so as to be suitable for infection of cells. The kit may further comprise at least one container having a predetermined quantity of magnetic material.

The kit may be provided together with instructions for the infection of monocytes, monocyte derived cells or macrophages with the oncolytic Herpes Simplex Virus and/or for the loading of monocytes, monocyte derived cells or macrophages with the magnetic material. Such instructions may be for carrying out said infection and/or loading ex vivo or in vitro, e.g. under conditions of in vitro cell culture.

Methods according to the present invention may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo"

refers to something present or taking place outside an organism, e.g. outside the human or animal body, which may be on tissue (e.g. whole organs) or cells taken from the organism.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which.

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

EXAMPLES

The examples presented below show that tumour-conditioned macrophages infected with oncolytic HSV1716 (Seprehvir) display a classic activated (M1) profile characterized by the expression of pro-inflammatory factors such as iNOS, IL-6, IL-8 and TNF-α. Furthermore, the M1 macrophages can be magnetically labeled using super-paramagnetic iron oxide nanoparticles (SPIOs) and then non-invasively steered from the bloodstream into deep target tissues, including primary and secondary tumours, using pulsed magnetic-field gradients inherent to all magnetic resonance imaging systems (MRI). We have used this magnetic resonance targeting (MRT) approach to deliver a cell-based oncolytic virotherapy. Relaxometry measurements suggest that standard MR imaging can then be used to monitor the efficacy of this therapy.

Example 1

HSV1716 and Human Primary Macrophages

Figure 1:
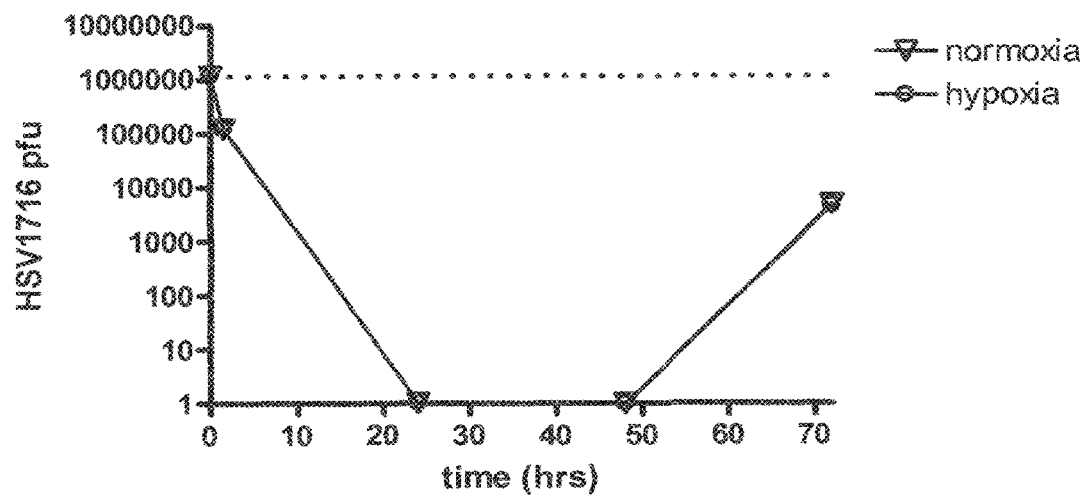
FIG. 1. Chart showing titration of human macrophages at various times after infection with 4 pfu/cell HSV1716 and culture in normoxia or hypoxia. Approximately 300,000 primary human macrophages were infected with 1,180,000 pfu HSV1716 with samples collected at various times post infection and HSV1716 titrated on Vero cells. Total titratable virus was graphed against time and the dotted line represents the amount of input virus FIG. 2. Chart showing output (total pfu) from human macrophages after 72 hrs of normoxia infection with HSV1716 at various input moi. Approximately 300,000 primary human macrophages were infected HSV1716 at moi 40, 4, 0.4 and 0.04 with samples collected at 72 hrs post infection only and HSV1716 titrated on Vero cells.

1) In an initial study human macrophages were infected with HSV1716 at approximately 4 pfu/cell and the cells were then incubated under normal and hypoxic conditions. Samples were removed at various time points after infection (+1.5 hr, +24 hrs, +48 hrs and +72 hrs) and titrated (FIG. 1).

Within 1 hour 90% of the virus had been adsorbed by the macrophages and then no virus was detectable at 24 or 48 hrs in either normoxia or hypoxia (detection limit of titration is 100 pfu/ml).

Significantly, virus was detectable at 72 hrs but the amounts at this time were similar in the normoxic vs hypoxic macrophages. This emergent virus is of significant interest as it could either be the original input which had entered some transient latent state or represent the first wave of replication in the macrophages.

Figure 2:
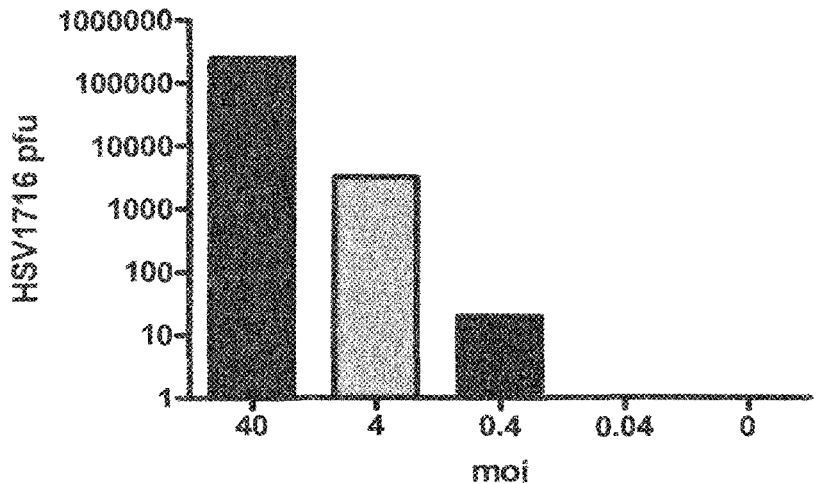

2) Macrophages were infected with decreasing HSV1716 moi (40, 4, 0.4 and 0.04) and samples were titrated after 72 hrs only. Virus was detected from the macrophages infected at moi 40, 4 and 0.4 but not from those infected at 0.04 moi (FIG. 2). Interestingly, the ratio of virus detected after 72 hrs relative to the input pfu was approximately the same and similar to those from the two other 72 hr normoxia/hypoxia time points shown in FIG. 1.

In summary, human primary macrophages were found to have a high capacity to adsorb HSV1716, and active virus can be recovered from the macrophages after 48 hrs in culture.

Example 2

Three different cancer cell lines were used (LNCaP, PC3, T47D) and macrophages were derived from human mononuclear cells; multicellular spheroids were prepared on agarose-coated culture plates; HSV1716GFP was used, to allow quantification of uptake by cancer cells and tumor spheroids by fluorescence microscopy and flow cytometry; finally, RT-PCR was performed to analyse changes in macrophage gene expression after HSV1716 infection.

Results showed that HSV1716 induces cell death in prostate and breast cancer cell lines and that macrophages infected by HSV1716 are effectively killed within 96 hours; moreover, infiltration of spheroids with HSV1716-infected macrophages causes tumor spheroid cell death.

Materials and Methods

Cell Lines

Human prostate carcinoma cell lines LNCaP and PC3 and human breast carcinoma cell line T47D were provided by Dr Helen Bryant (Department of Oncology, The Medical School, Sheffield, UK). Cells were cultured in RPMI supplemented with 10% Fetal Bovine Serum.

Preparation of Human MDM

Macrophages were derived from human mononuclear cells, which were isolated from platelet-depleted buffy coats (Blood Transfusion Service, Royal Hallamshire Hospital, Sheffield, UK). Mononuclear cells were separated from blood by using Ficoll gradient centrifugation (BURKE 2003). After isolation, mononuclear cells were seeded into T75 tissue culture flasks (~70×10$^6$ cells/flask) and cultured in IMDM supplemented with 2% AB serum for 3 days.

Herpes Simplex Virus 1716

HSV1716 was provided by Virttu Biologics (Glasgow, UK). Infection of tumor cells was performed by using multiplicity of infection (MOI), that is, the number of virus particles added per cell during infection, of 0.5 and 5. For macrophage infection, MOI of 5 and 50 were used. The labelling with GFP allowed detection of HSV1716 (measured by flow cytometry and fluorescent microscopy).

Infection of Primary MDM

MDM were cultured for 3 days in IMDM supplemented with 2% AB serum; after 3 days, cells were washed with PBS and medium was replaced with RPMI supplemented with 10% FBS. Cells were infected at MOI 50 and incubated overnight (normoxic conditions: 20% pO$_2$; hypoxic conditions: 0.1% pO$_2$). After 24 hours, conditioned medium was replaced with fresh medium and cells were incubated for further 72 hours. After 96 hours (4 days) from infection, cell viability was measured by flow cytometry.

Infiltration of Primary MDM into Tumor Spheroids

Tumor spheroids were prepared using LNCaP cells by seeding 2×10$^4$ cells/well into 2% agarose-coated 96-well plates in 100 μl RPMI (+10% FBS). After 72 hours (3 days), 5×10$^3$ infected macrophages were added to each well. Analysis of cell death was performed after a further 5 days; each day, spheroids were observed under the fluorescence microscope to detect the presence of HSV1716GFP in the hypoxic core.

Flow Cytometry

Cell viability/death and GFP expression were measured by flow cytometry. Cells were harvested, re-suspended in PBS and labelled with PI (1 μl/sample) to quantify cell death. Attune Acoustic Focusing Cytometer (Life Technologies) was used to analyse percentage of PI positive cells and GFP positive cells in each sample. PI (excitation wavelength: 488 nm; maximum emission: 617 nm) was detected by BL3 detector; BL1 was used for GFP detection (excitation at 488 nm and maximum emission at 509 nm).

RT-PCR

Reverse transcription-polymerase chain reaction (RT-PCR) was performed to detect RNA levels in infected macrophages and determine whether HSV1716 causes changes in gene expression. Cells (1.5×10$^6$) were plated into 6-well plates and infected with HSV1716 at MOI 50. After incubation for 48 hours (normoxic conditions: 20% pO$_2$; hypoxic conditions: 0.1% pO$_2$), cells were harvested and RNA extraction was performed using the RNeasy Mini Kit (Qiagen). cDNA was synthesised from RNA using the Primer design Precision nanoScript RT Kit and the T100 Thermal Cycler (Bio-Rad). cDNA was plated in 384-well PCR plates with primers of genes of interest. PCR was performed using the ABI7900 Real Time PCR.

```
IL-6
forward:
                                            (SEQ ID NO: 1)
5'-CGAAAGTCAACTCCATCTGCC-3' reverse:
                                            (SEQ ID NO: 2)
5'-GGCAACTGGCTGGAAGTCTCT-3'

IL-8
forward:
                                            (SEQ ID NO: 3)
5'-GGGCCATCAGTTGCAAATC-3' reverse:
                                            (SEQ ID NO: 4)
5'-TTCCTTCCGGTGGTTTCTTC-3'

TNFα
forward:
                                            (SEQ ID NO: 5)
5'-CCAGGAGAAAGTCAGCCTCCT-3' reverse:
                                            (SEQ ID NO: 6)
5'-TCATACCAGGGCTTGAGCTCA-3')

IL-1
forward:
                                            (SEQ ID NO: 7)
5'-CACCTCTCAAGCAGAGCACAG-3' reverse:
                                            (SEQ ID NO: 8)
5'-GGGTTCCATGGTGAAGTCAAC-3')

NFκB
forward:
                                            (SEQ ID NO: 9)
5'-ACCTGAGTCTTCTGGACCGCTG-3' reverse:
                                            (SEQ ID NO: 10)
5'-CCAGCCTTCTCCCAAGAGTCGT-3'

TGFβ
forward:
                                            (SEQ ID NO: 11)
5'-TAGGAACAGGCGGCGACGAATACA-3' reverse:
                                            (SEQ ID NO: 12)
5'-CACAATCACAAGGCAACTTCAAT-3'

IL-10
forward:
                                            (SEQ ID NO: 13)
5'-GCCTAACATGCTTCGAGATC-3' reverse:
                                            (SEQ ID NO: 14)
5'-CTCATGGCTTTGTAGATGCC-3'

VEGF-A
forward:
                                            (SEQ ID NO: 15)
5'-GAAGTTCATGGACGTCTACCAG reverse:
                                            (SEQ ID NO: 16)
5'-CATCTGCTATGCTGCAGGAAGCT-3'

CXCL-6
forward:
                                            (SEQ ID NO: 17)
5'-GAATTTCCCCAGCATCCCAAAG-3' reverse:
                                            (SEQ ID NO: 18)
5'-TGCCTTCTGCACTCCCTTTATC-3'

CXCL-1
forward:
                                            (SEQ ID NO: 19)
5'-AGAATGTTTTCAAATGTTCTCCAGTC-3' reverse:
                                            (SEQ ID NO: 20)
5'-GGCCATTTGCTTGGATCCG-3'
```

Statistical Analysis

Data are reported as mean±SEM. Statistical analysis and graphics were performed using GraphPad Prism. Two-way ANOVA test for multiple comparisons and multiple t tests were performed to compare experimental data obtained. Statistical significance was limited to the value of p=0.05.

Results

HSV1716 Induces Tumor Cell Death

LNCaP Cell Line

Figure 3A:
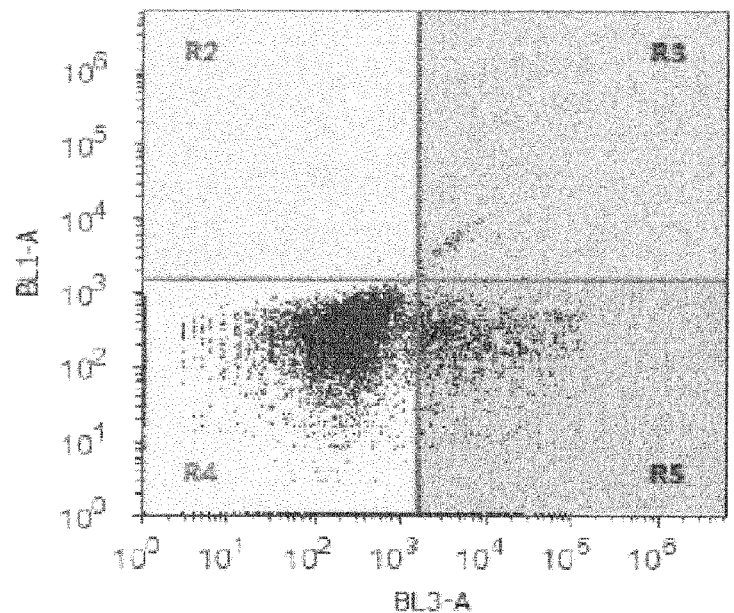
FIGS. 3A-B. Representative density plots of LNCaP cell population after 72 hours from infection at MOI 0 (control) (A) and 5 (B). BL3-A detector (X-axis) is a measure of PI, while BL1-A detector (Y-axis) is a measure of GFP. Each dot represents a cell. Quadrant R4 shows alive population not infected by HSV1716 (PI−/GFP−); quadrants R3 and R5 represent the quantity of dead cells (PI+); R2 shows living cells infected by HSV1716 (PI−/GFP+). While in the control (A) the cell population is mainly distributed in R4, at MOI 5 (B) cells move towards the right-hand side (R3+R5) and the upper side of the plot (R2), indicating respectively increased cell death and presence of a percentage of living cells infected by HSV1716. Plots have been obtained from the Attune cytometric software.
Figure 3B:
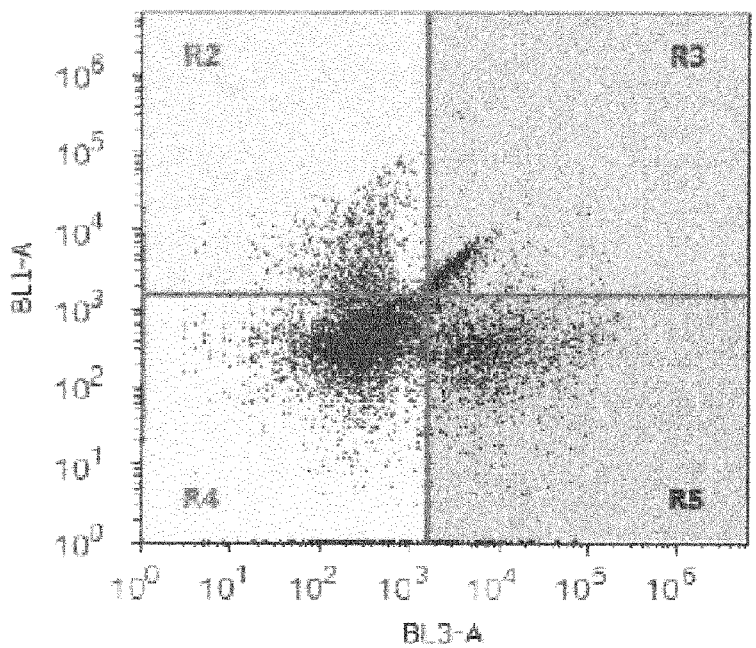
Figure 4A:
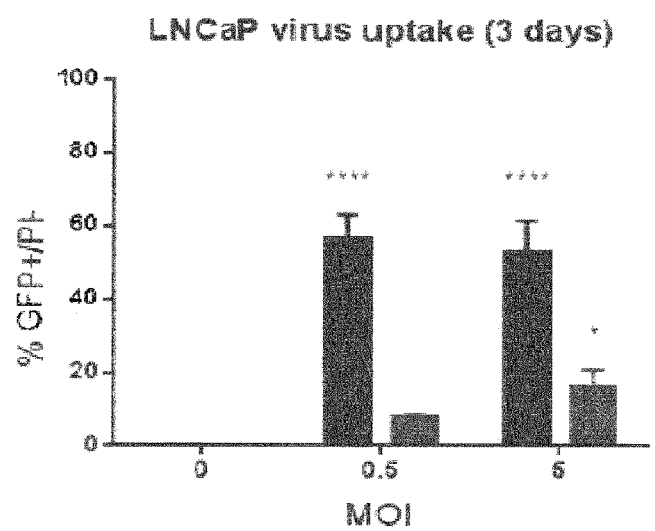
FIGS. 4A-B. HSV1716 induces LNCaP cell oncolysis. (A) X-axis shows MOI, Y-axis shows the percentage of living cells that have taken up HSV1716. Statistical significance was observed in normoxic conditions (left hand bar of each data point; hypoxic=right hand bar of each data point) at both MOI 0.5 and 5. (B) X-axis displays MOI, while percentage of cell death is reported on Y-axis. Cell death is statistically significant at MOI 5 in both normoxic and hypoxic conditions (normoxic=left hand bar of each data point; hypoxic=right hand bar of each data point). Of note, data are the mean±SEM of n=4 repeats. p-value<0.05, measured by using two-way Anova test for multiple comparisons.
Figure 4B:
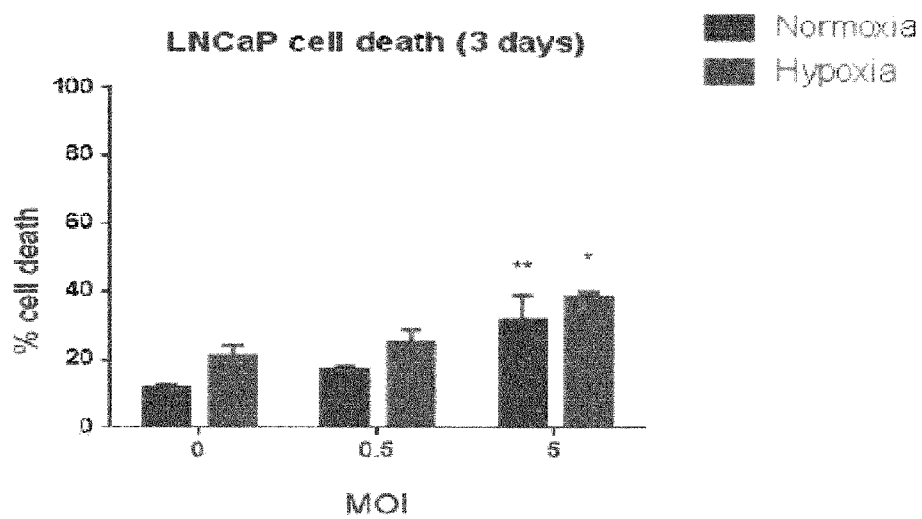

To analyse the oncolytic potentiality of HSV1716 on prostate cancer cells, LNCaP cells were seeded into 12-well plates (2×10$^4$ cells/well) and infected with HSV1716 at MOI 0 (control), 0.5 and 5. The infection was repeated using HSV1716-GFP in order to visualise virus uptake by living cells. Plates were kept in normoxic and hypoxic incubators, to investigate the ability of HSV1716 to kill cells in both oxygenated and non-oxygenated conditions. After 24 hours, conditioned medium was replaced with fresh medium. After 72 hours, plates were harvested and cells were analysed by flow cytometry. Cell death was measured as PI(+) cells; virus uptake in living cells was measured as GFP(+)/PI(−) cells (FIG. 3). After 72 hours from infection, virus uptake was observed in 56±6.35% of cells at MOI 0.5 (p<0.0001) and 53±8.7% of cells at MOI 5 (p<0.0001) in normoxic conditions, while levels were considerably lower in hypoxic conditions (16±4.73% at MOI 5, p<0.05). At MOI 5, statistically significant levels of cell death were observed in both normoxic (31±7.32%, p<0.01) and hypoxic (38±1.36%, p<0.05) conditions (FIG. 4). Interestingly, although virus uptake did not seem to be that high under hypoxic conditions, results revealed significant levels of cell death at MOI 5 (FIG. 4).

PC3 Cell Line

Figure 5A:
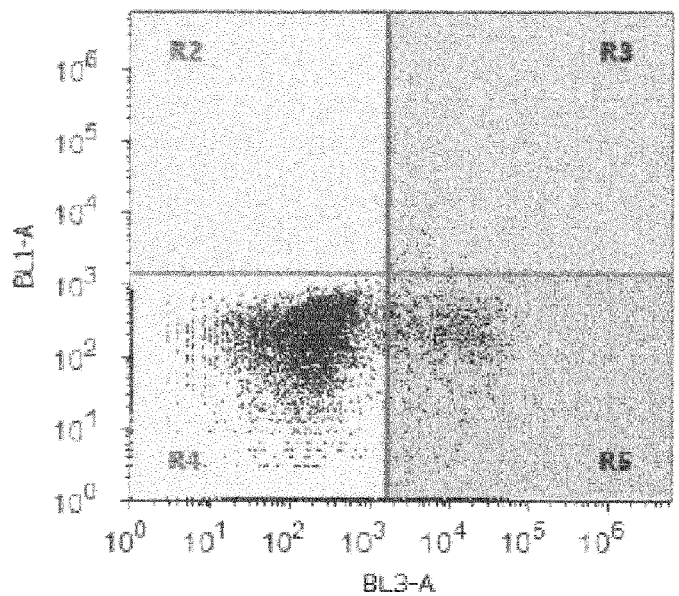
FIGS. 5A-B. Representative density plots of PC3 cell population after 72 hours from infection at MOI 0 (control) (A) and 5 (B). BL3-A detector (X-axis) is a measure of PI, BL1-A detector (Y-axis) is a measure of GFP. Each dot represents a cell. Quadrant R4 shows alive population not infected by HSV1716 (PI−/GFP−); quadrants R3 and R5 represent the quantity of dead cells (PI+); R2 shows living cells infected by HSV1716 (PI−/GFP+). Compared to the control (A), where cell population is mostly composed by living cells (events distributed in R4), at MOI 5 (B) a consistent proportion of cells has shifted towards the right-hand side (dead cells) and the upper side of the plot (R2: infected living cells). Plots have been obtained from the Attune cytometric software.
Figure 5B:
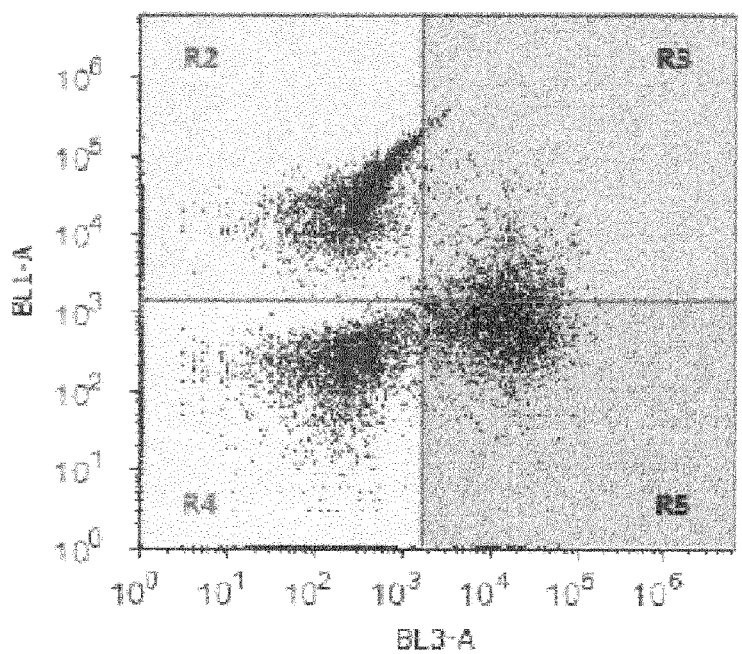
Figure 6A:
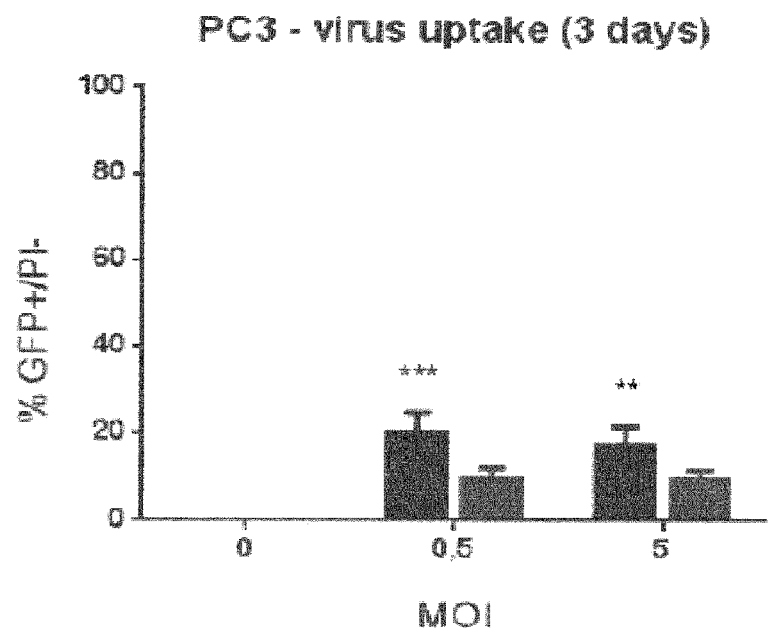
FIGS. 6A-B. HSV1716 has cytotoxic effect on PC3. (A) X-axis shows MOI, Y-axis shows the percentage of living cells that have taken up HSV1716. Statistical significance was observed in normoxic conditions (left hand bar of each data point; hypoxia=right hand bar of each data point) at both MOI 0.5 and 5. (B) X-axis displays MOI, Y-axis shows percentage of cell death. Cell death is statistically significant at MOI 0.5 and 5 in both normoxic and hypoxic conditions (normoxic=left hand bar of each data point; hypoxic=right hand bar of each data point). Results are the mean±SEM of 4 (A) and 8 (B) repeats. p-value<0.05, measured by using two-way Anova test for multiple comparisons.
Figure 6B:
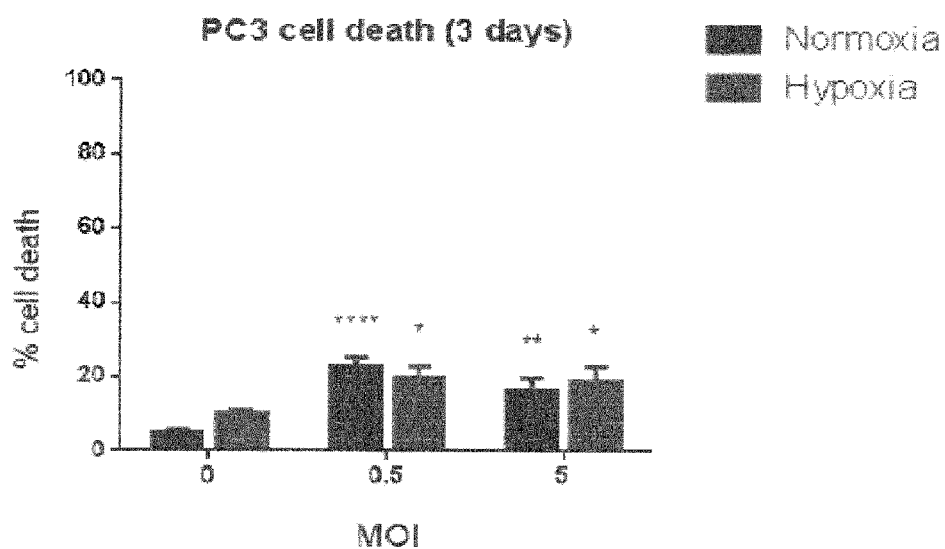

PC3s are a prostate cancer cell line with high metastatic capacity and considerably more aggressive than LNCaPs. $2 \times 10^4$ cells were seeded into 12-well plates and infected with HSV1716 at MOI 0, 0.5 and 5. Cells were incubated in normoxic and hypoxic conditions for 72 hours. After 24 hours, conditioned medium was replaced with fresh medium to eliminate viral particles not taken up by cells. After 72 hours, cells were analysed by flow cytometry and the amount of PI(−)/GFP(+) cells was plotted (FIG. 5). Percentages of virus uptake indicate a significant presence of living cells infected by viral particles in normoxic conditions (20±4.46% at MOI 0.5, 17±4.37% at MOI 5, p<0.05); cell death was statistically significant in both normoxic (23±2.49% at MOI 0.5, p<0.0001, and 17±3.14% at MOI 5, p<0.01) and hypoxic conditions (20±1.34% at MO10.5 and 19±2.68% at MOI 5, p<0.05). Percentages of virus uptake by living cells and cell death were reported graphically (FIG. 6).

T47D Cell Line

Figure 7A:
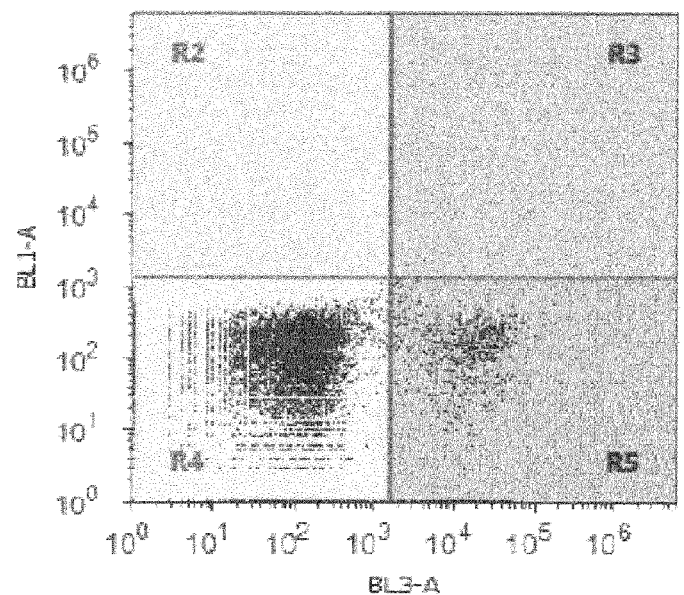
FIGS. 7A-B. Representative density plots of T47D cell population after 120 hours from infection at MOI 0 (control) (A) and 5 (B). BL3-A detector (X-axis) is a measure of PI, BL1-A detector (Y-axis) is a measure of GFP. Each dot represents a cell. Quadrant R4 shows alive population not infected by HSV1716 (PI−/GFP−); quadrants R3 and R5 represent the quantity of dead cells (PI+); R2 shows living cells infected by HSV1716 (PI−/GFP+). Living cell population (A, control) moves towards the right-hand side of the plot after 120 hours from infection (B, MOI 5), indicating the presence of dead cells. A marked proportion of cells was also observed in the R2 quadrant (infected living cells). Plots have been obtained from the Attune cytometric software.
Figure 7B:
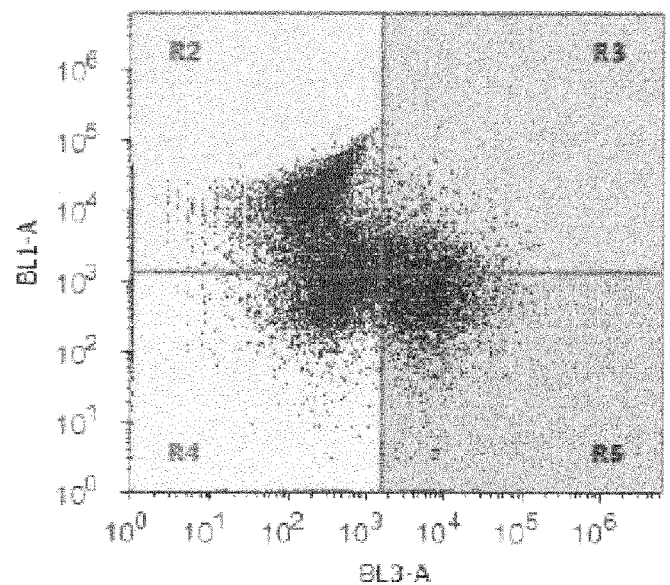
Figure 8A:
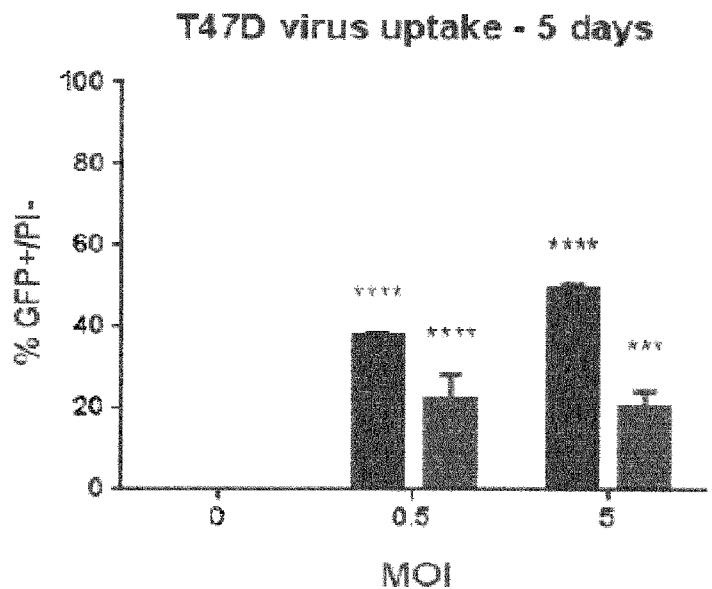
FIGS. 8A-B. HSV1716 infection induces T47D cell death. (A) X-axis shows MOI, Y-axis shows the percentage of living cells that have taken up HSV1716. Statistical significance was observed in normoxic and hypoxic conditions (normoxic=left hand bar of each data point; hypoxia=right hand bar of each data point) at both MOI 0.5 and 5. (B) X-axis shows MOI, Y-axis shows percentage of dead cells. Cell death is statistically significant at MOI 5 in both normoxic and hypoxic conditions. Results are the mean±SEM of n=3 (A) and n=5 (B) independent experiments. p-value<0.05, measured by using two-way Anova test for multiple comparisons.
Figure 8B:
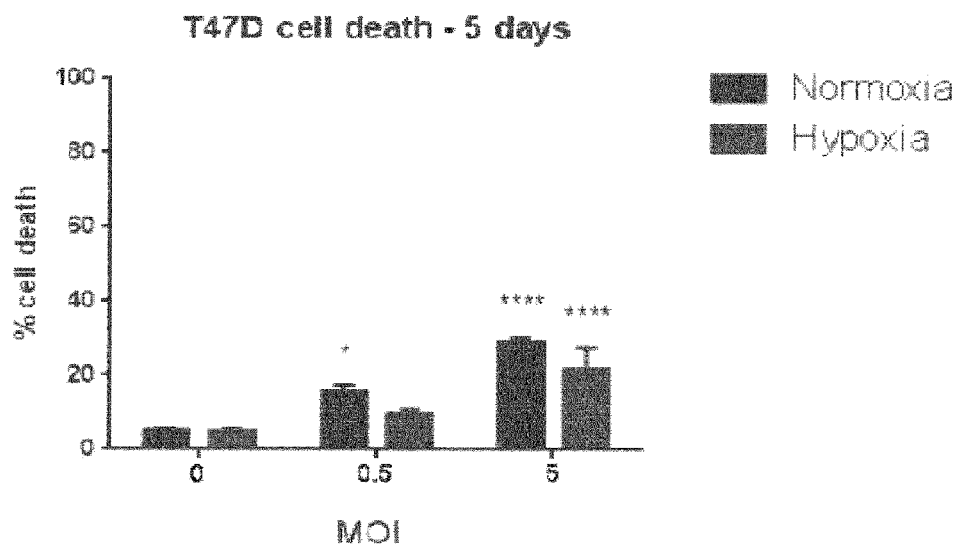

To investigate the oncolytic ability of HSV1716 on different types of solid tumors, effects of infection of a breast carcinoma cell line, T47D, was evaluated. $1 \times 10^5$ cells were seeded into 12-well plates and infected with HSV1716 and HSV1716-GFP at MOI 0, 0.5 and 5. Cells were incubated under normoxic and hypoxic conditions for 72 hours and analysed by flow cytometry. No signs of cell death were observed in any conditions, while virus uptake was markedly high even at MOI 0.5 (data not shown). Therefore, the analysis was repeated after 120 hours, to verify whether T47D cell line is either not responsive to the HSV1716, or just less sensitive than prostate carcinoma cell lines. After 120 hours, cells were observed by flow cytometry and the amount of PI(−)/GFP(+) cells was plotted (FIG. 7). Virus uptake by living cells was significant at MOI 0.5 and 5, with considerably higher levels in normoxia (38±0.35% at MOI 0.5, 49±0.49% at MOI 5, p<0.0001) than hypoxia (27±5.52% at MOI 0.5, 17±2.18% at MOI 5, p<0.001), and cell death was found to be significant at MOI 5 in both normoxic and hypoxic conditions (29±1.37% and 22±5.82% respectively, p<0.0001) (FIG. 8b).

Effects of HSV1716 Infection on Human Macrophages

HSV1716 Effectively Kills Human Macrophages

Figure 9A:
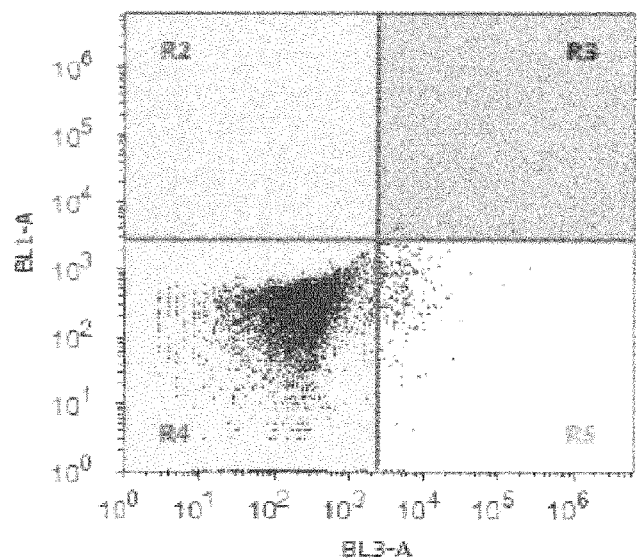
FIGS. 9A-C. Representative density plots of MDM cell population after 96 hours from infection at MOI 0 (control) (A), 5 (B) and 50 (C). BL3-A detector (X-axis) is a measure of PI, BL1-A detector (Y-axis) is a measure of GFP. Each dot represents a cell. Quadrant R4 shows alive population not infected by HSV1716 (PI−/GFP−); quadrants R3 and R5 represent the quantity of dead cells (PI+). Compared to the control (A), where cell population is mostly composed by living cells, at MOI 5 (B) a switch towards the right-hand side of the graph is observed (R3, R5), indicating an increase in the percentage of dead cells. At MOI 50 (C), a slight increment in cell death is detected, however there is not a considerable difference between MOI 5 and 50. Plots have been obtained from the Attune cytometric software.
Figure 9B:
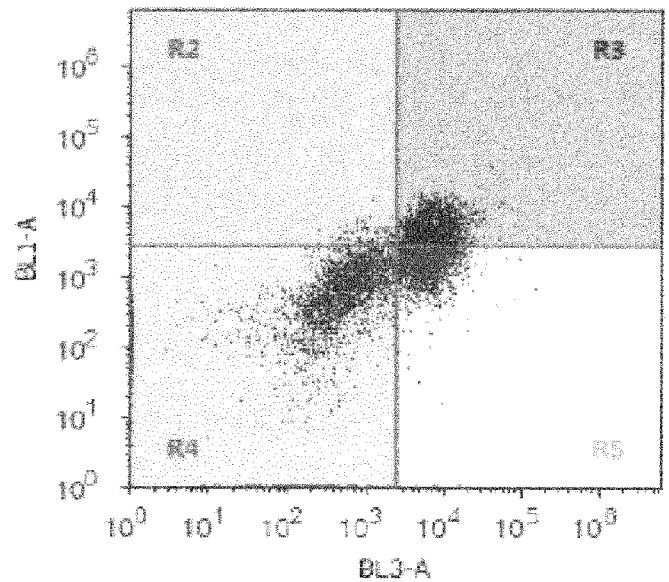
Figure 9C:
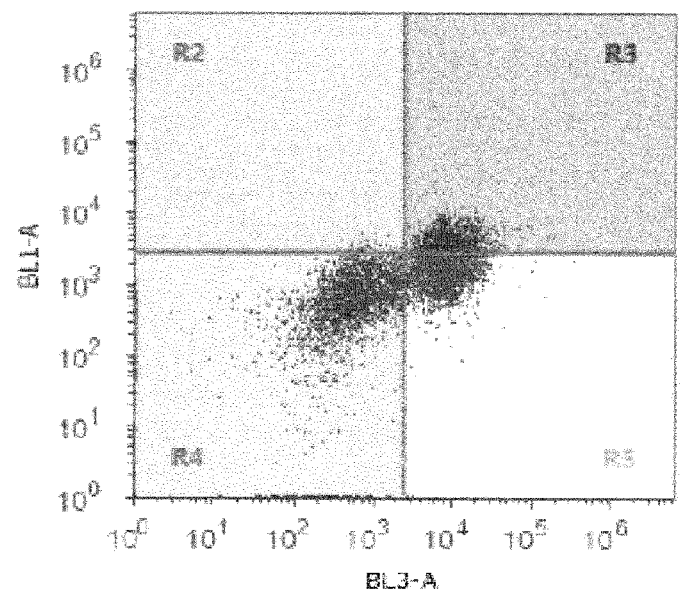
Figure 10:
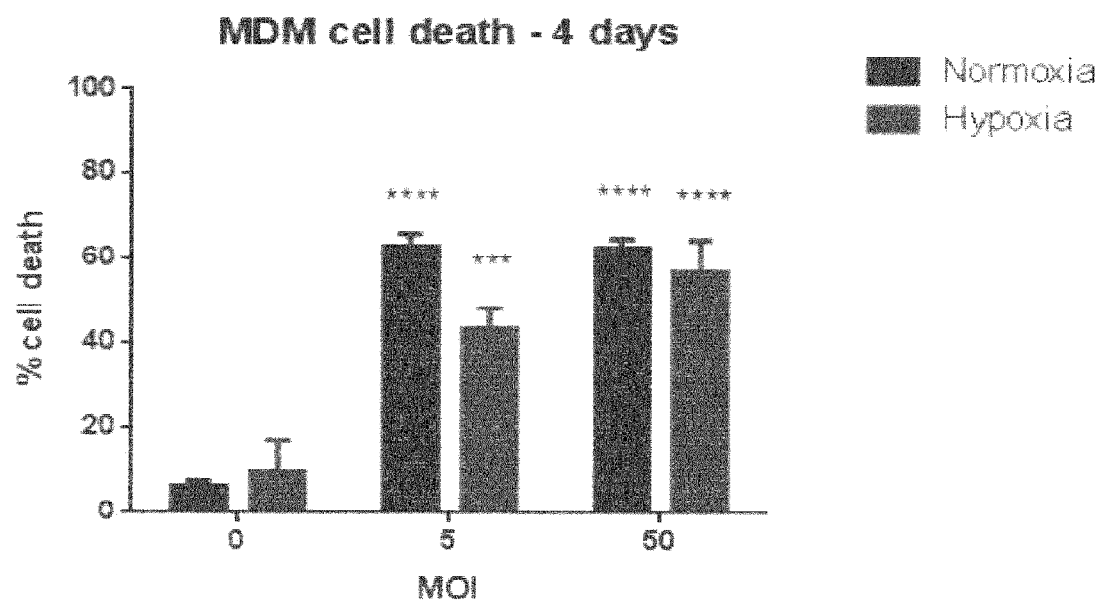
FIG. 10. HSV1716 causes MDM cell death. X-axis shows MOI, Y-axis shows percentage of dead cells. Cell death is statistically significant at MOI 5 and MOI 50 (p-value<0.001) in both normoxic and hypoxic conditions (normoxic=left hand bar of each data point; hypoxia=right hand bar of each data point). At MOI 50, an increment in cell death is observed under hypoxic conditions. Results are the mean±SEM of n=4 independent experiments. Statistical comparisons performed using two-way Anova test for multiple comparisons.

To determine if macrophages could be used as a delivery system for HSV1716 therapy, it was fundamental to test the consequences of viral infection on macrophage cells. After 3 days from isolation, MDM were harvested and counted; $1 \times 10^6$ cells were seeded in 6-well plates. Once cells attached to the plastic, infection was performed. HSV1716 was added at MOI 0 (control), 5 and 50. Cells were incubated in normoxic and hypoxic conditions for 96 hours. Medium was replaced with fresh medium after 24 hours, and on day 4 supernatant was collected from each well for further studies. After 96 hours, plates were harvested and cell viability was analysed by flow cytometry. Results showed an effective killing of cells at both MOI 5 and 50, with high percentages of cell death under both normoxic conditions (63±2.76% at MOI 5, 62±2.42% at MOI 50, p<0.0001) and hypoxic conditions (43±4.91% at MOI 5, p<0.001, and 57±7.34% at MOI 50, p<0.0001) (FIGS. 9, 10).

Infected Macrophages Release Viral Particles

Figures 11, 12:
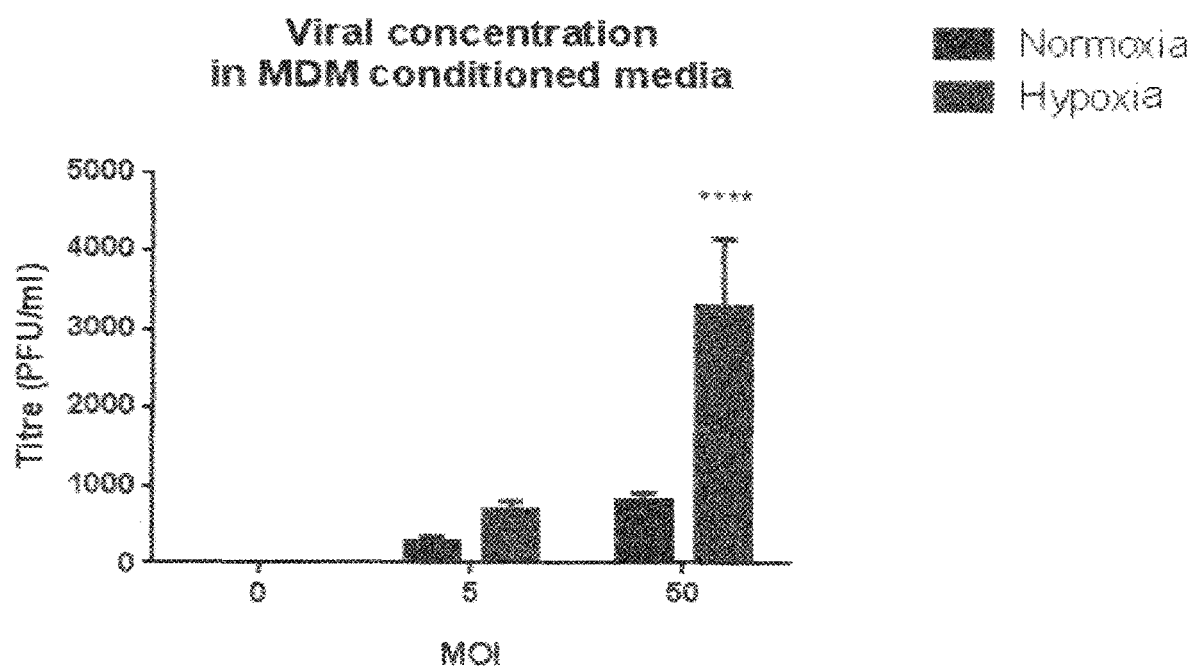
FIG. 11. Table 1: Concentration of HSV1716 (PFU/ml) detected in macrophage-conditioned medium. The table display the concentration of HSV1716 (PFU/ml) present in supernatant collected from MDM infected at MOI 0, 5, 50 and incubated under normoxic and hypoxic conditions. Rows show the different microenvironment (normoxia, hypoxia); columns indicate the viral infection performed (control, MOI 5, MOI 50). Viral particles were detected at both MOI 5 and 50, with greater concentration at MOI 50 in both normoxic and hypoxic conditions. Data are the mean±SEM of n=4 independent experiments.
FIG. 12. HSV1716 lyses human macrophages and is released into the microenvironment. X-axis shows MOI at which MDM were infected, Y-axis shows concentration (PFU/ml) of HSV1716 found in supernatant collected from plates. Results are statistically significant at MOI 50 under hypoxic conditions (p-value<0.0001, determined by using the two-way Anova test for multiple comparisons). Data show the mean±SEM of n=4 independent experiments. Normoxic=left hand bar of each data point; hypoxic=right hand bar of each data point.

Since more than half of cells are killed by HSV1716, the considerable viral replication following infection and lysis of cells should lead to the release of viral particles in the microenvironment. Therefore, to confirm the ability of HSV1716 to kill and replicate in macrophages, supernatant from each well was collected after 96 hours from infection and analysed. Samples, consisting of medium acquired from cells infected at M010, 5 and 50 in both normoxic and hypoxic conditions and the presence of viral particles in the supernatant was determined by titration. HSV1716 was detected in the supernatant of MDM infected at MOI 5 and 50, with higher concentration for the higher MOI, while no virus was observed in control groups (Table 1 (FIG. 11)). Interestingly, samples collected from cells infected under hypoxic conditions showed a 2.5-fold greater concentration (at MOI 5) and a 4-fold greater concentration (at MOI 50) of HSV1716 compared to their normoxic equivalents (FIG. 12).

To reaffirm this result, infection of tumor cells with conditioned medium collected from infected MDM was performed. LNCaP cells were seeded into 12-well plates ($1 \times 10^4$ cells/well) and infected with 100 µl of MDM supernatant in 1 ml RPMI. After 120 hours from infection, cells were harvested and analysed by flow cytometry. After PI staining, however, cell death was found to be only significant at MOI 50, in cells infected with conditioned medium collected from MDM under normoxic conditions (40±7.26%, p<0.01), in contrast with what was expected from titration studies (higher cell death under hypoxic conditions) (FIG. 8).

HSV1716 Infection Modifies Macrophage Gene Expression

Figures 13, 14:
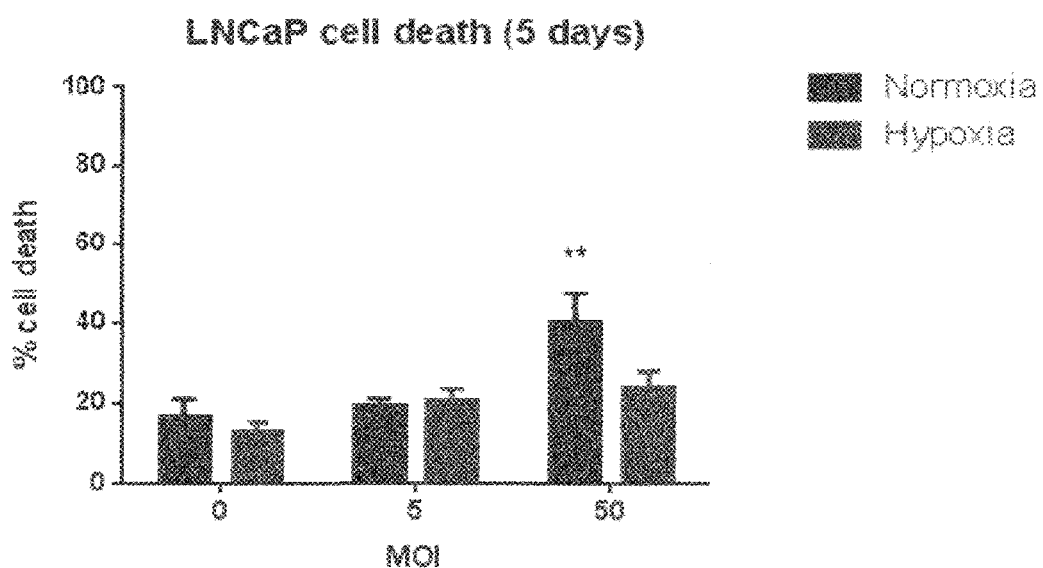
FIG. 13. Viral particles contained in MDM-conditioned medium induce LNCaP cell death. X-axis shows the MOI used to infect macrophages from which the conditioned medium was collected. Y-axis shows percentage of dead cells. Cell death is statistically significant at MOI 50 in normoxic conditions (p-value<0.01). Results are the mean±SEM of n=3 independent experiments. Statistical analysis was performed by using two-way Anova test for multiple comparisons. Normoxic=left hand bar of each data point; hypoxic=right hand bar of each data point.
FIG. 14. Table 2: HSV1716 induces alterations in MDM gene expression levels. Table 2 shows fold changes in MDM gene expression calculated for 10 genes of interest (named in the first row) after 48 hours from HSV1716 infection at MOI 50 in both normoxic (second row) and hypoxic (third row) conditions. Infection under each condition has been repeated twice. Underlined values represent indicatively relevant alterations in gene expression, either up-regulation (value>1) or down-regulation (value<1); i.e. the underlined value 5.13 means that, after infection at MOI 50, the cytokine IL-8 was found to be overexpressed in hypoxic conditions, resulting in a 5-fold increase compared to the control.

To investigate how infection with HSV1716 changes MDM gene expression, mRNA levels of cytokines and growth factors of interests were quantified using quantitative RT-PCR. $1.5 \times 10^6$ cells were seeded into 6-well plates and infected at MOI 50; plates were incubated under normoxic and hypoxic conditions, to understand possible alterations in gene expression due to the different environment. 48 hours post infection, cells were harvested and mRNA was extracted from infected cells and control groups. cDNA was then synthesised from RNA, and plated into 384-well plates with primers of genes of interest: the pro-inflammatory cytokines IL-6, IL-8, TNF-α, IL-1, CXCL1; the transcription factor NFκB, the anti-inflammatory cytokines IL-10 and CXCL-6, the growth factors VEGF-A and TGF-β. β-actin was chosen as constitutively expressed housekeeping gene. After performing RT-PCR, mRNA levels of each gene were normalised for β-actin concentration and fold changes in the expression were calculated. Gene induction profile caused by HSV1716 infection was obtained in duplicate. Fold changes in expression calculated for each gene were reported; results suggest that, at MOI 50, HSV1716 is an inducer of pro-inflammatory cytokines (higher induction profile of IL-8, IL-1 and the pro-inflammatory transcription factor NFκB in hypoxic conditions). At the same time, expression of NFκB and the anti-inflammatory TGF-β and IL-10 were reduced in normoxia (despite an apparent induction of the latter under hypoxic conditions), while no detectable alteration of gene expression was observed for the chemokines CXCL-1 and CXCL-6. Interestingly, a markedly high induction of VEGF-A after infection was observed under hypoxic conditions (Table 2 (FIG. 14)).

Infiltration of Spheroids with MDM Leads to Tumor Shrinkage

Figure 15:
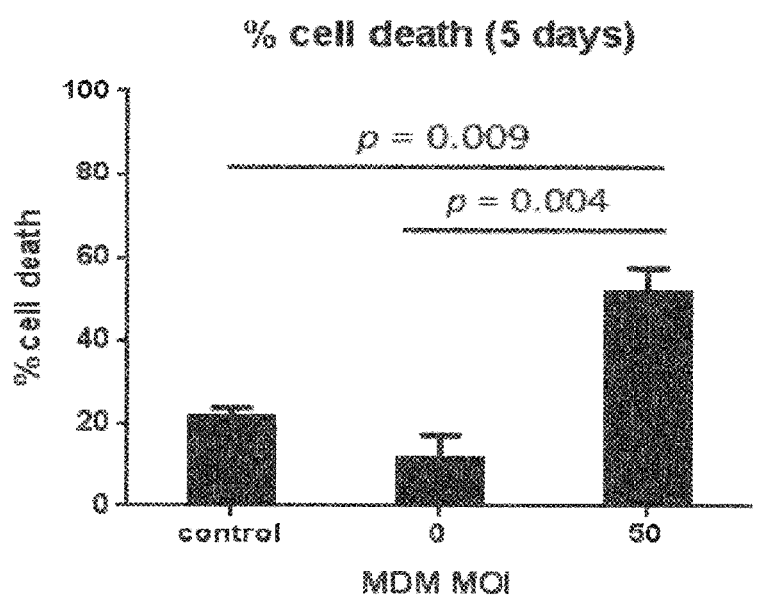
FIG. 15. Infiltration of spheroids with infected MDM (MOI 50) induces spheroid cell death. Graph shows cell death detected by flow cytometry after 5 days from infiltration (day 9 of experiment). Y-axis shows % cell death (PI+), X-axis shows the MOI at which MDM were infected before infiltration. While no significant differences in viability were observed between control spheroids (control) and infiltration with non-infected MDM (0), cell death was statistically significant when spheroids were infiltrated with MDM infected at MOI 50 (50) (51±5.92% cell death) when comparing the latter with both control and 0 (p-values=0.009, 0.004 respectively). Results are the mean±SEM of n=3 independent experiments. Statistical analysis was performed using multiple t tests.

To investigate if delivery of HSV1716 to tumors and, specifically, to the hypoxic core can be mediated by the use of macrophages, tumor spheroids were generated. The use of spheroids has the advantage, compared to 2D cultures, of being constituted by an oxygen-depleted central area surrounded by a well-oxygenated zone; therefore, a spheroid mimics 3D tumors. Tumor spheroids were generated on day 1 using LNCaP cells ($1.5 \times 10^4$ cells seeded into 2% agarose-coated 96-well plates). 3 days after plating cells (day 4), spheroids of 800 μm/1 mm diameter had developed. MDM were infected with HSV1716 at MOI 50 on day 3 and incubated for 24 hours, non-infected cells were used as controls. On day 4, cells were harvested and counted; spheroids were infiltrated with $5 \times 10^3$ MDM, both at MOI 0 (control MDM) and MOI 50 (infected MDM). In addition, control spheroids (non-infiltrated) were taken into account. Plates were incubated for further 120 hours (until day 9). On day 6, after 72 hours from MDM infection, pictures were taken using a fluorescence microscope, to visualise the presence of HSV1716 (labelled with GFP) inside the spheroids. Images revealed the presence of HSV1716-infected MDM; however, MDM seemed to be confined to the viable rim which surrounds the hypoxic core, while no GFP(+) cells were observed in the inner areas of spheroids. Central areas of spheroids (control groups) were found to be slightly necrotic and markedly darker than what was expected. On day 9, spheroids were further observed under the microscope and pictures were taken; no significant alterations in the shape and size of spheroids were detected. Spheroids were harvested and washed after 5 days from infiltration (day 9) and cell viability was analysed by flow cytometry; while no significant cell death was observed in control groups and in spheroids infiltrated with non-infected MDM, infiltration with MDM infected at MOI 50 caused oncolysis of 51±5.92% of cells (p-value<0.01) (FIG. 15).

Discussion

The findings revealed that prostate cancer cell lines LNCaP and PC3 and breast cancer cell line T47D are sensitive to HSV1716, indicating that this virus could be used as a therapy to treat a broad range of tumors. Although at different extent, both prostate and breast cancer cell lines were responsive to HSV1716 infection at MOI 5 after 72 hours (LNCaP, PC3) and 120 hours (T47D); in addition, the detection of high levels of virus uptake in living cells suggests that further cytotoxic effect could be induced over time. Percentages of cell death were similar in normoxic and hypoxic conditions for all the cell lines tested (no statistical significance was observed between the two groups): this result indicates that hypoxia does not confer resistance to HSV1716 to tumor cells in vitro; HSV1716, therefore, could potentially be used to kill difficult to treat hypoxic areas of cancer. Interestingly, despite the fact that significant cell death is observed under oxygen-depleted conditions, virus uptake in hypoxia is generally lower than the uptake in normoxia for both prostate and breast cancer cell lines—and is not significant for PC3. However, the high levels of cell death reported suggest a greater sensitivity to HSV1716 in hypoxic conditions.

The studies carried out on human macrophages showed that they are sensitive to HSV1716. The ability of HSV1716 to kill macrophages after 96 hours from infection has a fundamental importance, as it implies the possibility of exploiting MDM as a delivery system for the virus, which will be transported inside the hypoxic areas of tumors by MDM, replicate, lyse MDM and, subsequently, infect and kill the nearby cancer cells. To further demonstrate that HSV1716 replication in MDM leads to the release of viral particles in the microenvironment, supernatant was collected from infected macrophages, with the aim of analysing it and detecting the presence of HSV1716. Results revealed that the viral concentration increases with an increasing MOI, as expected; interestingly, under hypoxic conditions replication and release of viral particles were 3 fold greater than in normoxia. When LNCaPs were infected with the same supernatant, however, after 120 hours cell death was only significant in normoxia, at M0150, whereas no significant values were observed under hypoxic conditions or at lower MOI. This result could be explained by the fact that the amount of viral particles observed after titration of supernatant, although higher in hypoxia, is generally not greater than $3 \times 10^3$ PFU/ml: such quantity could be not sufficient for the virus to kill cells, considering that 100 μl of supernatant containing HSV1716 at $3 \times 10^3$ PFU/ml (or less, in case of MOI 5) were used to infect $2 \times 10^4$ cells; this means that LNCaPs were infected at MOI<0.05—an extremely low MOI (bearing in mind that, when performing infection with HSV1716, significant cell death was only observed at MOI 5). However, such low values of HSV1716 detected in MDM-conditioned media implies release of the virus, and the importance of this finding is clear when considering that, in a putative therapeutic approach, once delivered through MDM and released in the environment, viral particles would encounter tumor cells, infect them, replicate, further amplifying the amount of viral copies, and subsequently disseminate widely into tumors.

To test the ability of MDM to deliver HSV1716 to tumors, and specifically to hypoxic areas, multicellular 3D spheroids were prepared, with the aim of mimicking the structure of a real tumor. The main objective was to understand if MDM actually deliver the virus, sufficiently for cell death to be induced in 3D spheroids. The relatively large diameter of spheroids (800 μm–1 mm) allowed the observation of possible alterations in shape and size under the microscope. In addition, the presence of GFP-labelled HSV1716 gave the opportunity to detect the presence of infected MDM inside the spheroids and, therefore, to observe if MDM actually reached the hypoxic core.

Significant cell death was observed in spheroids infiltrated with infected MDM (MOI 50) compared to control groups (p-value=0.009) and spheroids infiltrated with non-infected MDM (p-value=0.004).

HSV1716GFP was observed in spheroids treated with infected MDM, after 72 hours from MDM infection (day 6) with weak gfp fluorescence co-localising with the oxygenated rim. The absence of pronounced green stains could be due to the small quantity of MDM used (only $5 \times 10^3$ cells were infiltrated with each spheroid). However, delivery of HSV1716 was successful as spheroids infiltrated with infected MDM showed significant levels of cell death (51±5.92%, p-value<0.01) suggesting that HSV1716 replicates inside MDM and spreads in the micro-environment, ultimately killing tumor cells.

To understand how HSV1716 infection modifies gene expression in MDM, RT-PCR was performed. Genes of interest were selected based on their immune properties, the pro-inflammatory cytokines IL-8, IL-6, TNF-α, CXCL-1, the anti-inflammatory cytokines IL-10, CXCL-6 and the factors NFκB, VEGF-A, TGF-β. Virus infection of human cells generally leads to activation of signalling pathways that cause the induction of pro-inflammatory cytokines and transcription factors (Mogensen, T. H., and S. R. Paludan, 2001 Molecular pathways in virus-induced cytokine production. Microbiology and Molecular Biology Reviews 65: 131-+). It was considered interesting, therefore, to analyse both the effect of HSV1716 infection at MOI 50 on MDM gene expression and differences between infections performed under normoxic and hypoxic conditions.

HSV1716 infection at MOI 50 caused the induction of pro-inflammatory cytokines by 48 hours, and the increase in expression was especially observed under hypoxic conditions, whereas no considerable changes were observed in normoxia. Cytokines IL-8 and IL-1 were found to be 5- and 7-fold upregulated, respectively, in hypoxia. A 5-fold increased expression under hypoxic conditions was also observed for NFκB; however, surprisingly, NFκB is down-regulated by 5 folds in normoxia. This finding suggests a different response of MDM to HSV1716 which could have higher inflammatory properties in the absence of oxygen. If this is the case, this would suggest that HSV1716 acquires a greater viral potency in hypoxia: this result would further support the rationale of using virus delivery by MDM to target central areas of tumor, difficult to access through different ways.

The anti-inflammatory cytokine IL-10 and the growth factor TGF-β are down-regulated by 5 folds after HSV1716 infection, but only in normoxic conditions. Indeed, under hypoxia, a 4-fold increase in the anti-inflammatory IL-10 expression was observed, possibly opposing the pro-inflammatory effect. Interestingly, there is strong up-regulation of VEGF-A under hypoxic conditions (21 fold), which could be partly due by the fact that VEGF-A is normally involved in the hypoxic response.

In summary, this study demonstrates that HSV1716 induces tumor cell death in prostate and breast cancer cell lines, and is able to replicate in MDM and disseminate in the surrounding microenvironment. In addition, results show that when delivered through MDM, HSV1716 causes cell death in multicellular 3D spheroids; therefore, the macrophage-mediated delivery of oncolytic HSV1716 to tumors constitutes a possible therapeutic approach to treat solid tumors. The great safety profile of HSV1716, shown by previously performed clinical trials, makes the possibility of using it as a MDM deliverable therapy an exciting opportunity to further increase the range of treatments that can be offered to cancer patients.

References for Example 2

Arenberg, D. A., M. P. Keane, B. DiGiovine, S. L. Kunkel, S. R. B. Strom et al., 2000 Macrophage infiltration in human non-small-cell lung cancer: the role of CC chemokines. Cancer Immunology Immunotherapy 49: 63-70.

Behnes, C. L., F. Bremmer, B. Hemmerlein, A. Strauss, P. Strobel et al., 2014 Tumor-associated macrophages are involved in tumor progression in papillary renal cell carcinoma. Virchows Archiv 464: 191-196.

Brown, L. F., B. Berse, R. W. Jackman, K. Tognazzi, A. J. Guidi et al., 1995 EXPRESSION OF VASCULAR-PERMEABILITY FACTOR (VASCULAR ENDOTHELIAL GROWTH-FACTOR) AND ITS RECEPTORS IN BREAST-CANCER. Human Pathology 26: 86-91.

Burke, B., 2003 Macrophages as novel cellular vehicles for gene therapy. Expert Opinion on Biological Therapy 3: 919-924.

Burke, B., S. Sumner, N. Maitland and C. E. Lewis, 2002 Macrophages in gene therapy: cellular delivery vehicles and in vivo targets. Journal of Leukocyte Biology 72: 417-428.

Chen, J. J. W., Y. C. Lin, P. L. Yao, A. Yuan, H. Y. Chen et al., 2005 Tumor-associated macrophages: The double-edged sword in cancer progression. Journal of Clinical Oncology 23: 953-964.

Cheng, W. S., H. Dzojic, B. Nilsson, T. H. Totterman and M. Essand, 2006 An oncolytic conditionally replicating adenovirus for hormone-dependent and hormone-independent prostate cancer. Cancer Gene Therapy 13: 13-20.

Coukos, G., A. Makrigiannakis, E. H. Kang, D. Caparelli, I. Benjamin et al., 1999 Use of carrier cells to deliver a replication-selective herpes simplex virus-1 mutant for the intraperitoneal therapy of epithelial ovarian cancer. Clinical Cancer Research 5: 1523-1537.

Di Caro, G., F. Marchesi, L. Laghi and F. Grizzi, 2013 Immune cells: plastic players along colorectal cancer progression. Journal of Cellular and Molecular Medicine 17: 1088-1095.

Dincer, Y., T. Akcay, N. Celebi, I. Uslu, O. Ozmen et al., 2002 Glutathione S-transferase and O-6-methylguanine DNA methyl transferase activities in patients with thyroid papillary carcinoma. Cancer Investigation 20: 965-971.

Eckert, A. W., M. Kappler, J. Schubert and H. Taubert, 2012 Correlation of expression of hypoxia-related proteins with prognosis in oral squamous cell carcinoma patients. Oral and maxillofacial surgery 16: 189-196.

Fukuhara, H., Y. Homma and T. Todo, 2010 Oncolytic virus therapy for prostate cancer. International Journal of Urology 17: 20-30.

Gollapudi, K., C. Galet, T. Grogan, H. Zhang, J. W. Said et al., 2013 Association between tumor-associated macrophage infiltration, high grade prostate cancer, and biochemical recurrence after radical prostatectomy. American Journal of Cancer Research 3: 523-529.

Graves, D. T., R. Barnhill, T. Galanopoulos and H. N. Antoniades, 1992 EXPRESSION OF MONOCYTE CHEMOTACTIC PROTEIN-1 IN HUMAN-MELANOMA INVIVO. American Journal of Pathology 140: 9-14.

Gray, L. H., A. D. Conger, M. Ebert, S. Hornsey and O. C. A. Scott, 1953 THE CONCENTRATION OF OXYGEN DISSOLVED IN TISSUES AT THE TIME OF IRRADIATION AS A FACTOR IN RADIOTHERAPY. British Journal of Radiology 26: 638-648.

Griffiths, L., K. Binley, S. Iqball, O. Kan, P. Maxwell et al., 2000 The macrophage—a novel system to deliver gene therapy to pathological hypoxia. Gene Therapy 7: 255-262.

Grimshaw, M. J., S. Naylor and F. R. Balkwill, 2002 Endothelin-2 is a hypoxia-induced autocrine survival factor for breast tumor cells. Molecular Cancer Therapeutics 1: 1273-1281.

Harris, A. L., 2002 Hypoxia—A key regulatory factor in tumor growth. Nature Reviews Cancer 2: 38-47.

Harrow, S., V. Papanastassiou, J. Harland, R. Mabbs, R. Petty et al., 2004 HSV1716 injection into the brain adjacent to tumor following surgical resection of high-grade glioma: safety data and long-term survival. Gene Therapy 11: 1648-1658.

He, K.-F., L. Zhang, C.-F. Huang, S.-R. Ma, Y.-F. Wang et al., 2014 CD163+ Tumor-Associated Macrophages Correlated with Poor Prognosis and Cancer Stem Cells in Oral Squamous Cell Carcinoma, BioMed research international 2014: 838632.

He, W. S., X. F. Dai, M. Jin, C. W. Liu and J. H. Ren, 2012 Hypoxia-Induced Autophagy Confers Resistance of Breast Cancer Cells to Ionizing Radiation. Oncology Research 20: 251-258.

Jiang, G., C. S. Yang, D. Xu, C. Sun, J. N. Zheng et al., 2014 Potent anti-tumor activity of a novel conditionally replicating adenovirus for melanoma via inhibition of migration and invasion. British Journal of Cancer 110: 2496-2505.

Kacinski, B. M., 1995 CSF-1 AND ITS RECEPTOR IN OVARIAN, ENDOMETRIAL AND BREAST-CANCER. Annals of Medicine 27: 79-85.

Kandel, J. J., D. J. Yamashiro and J. Kitajewski, 2011 Angiogenesis in Tumor Development and Metastasis, pp. 81-93 in *Therapeutic Angiogenesis for Vascular Diseases: Molecular Mechanisms and Targeted Clinical Approaches for the Treatment of Angiogenic Disease*, edited by M. Slevin. Springer-Verlag Berlin, Berlin.

Kim, J., J. Y. Cho, J. H. Kim, K. C. Jung and C. O. Yun, 2002 Evaluation of E1B gene-attenuated replicating adenoviruses for cancer gene therapy. Cancer Gene Therapy 9: 725-736.

Kim, S., S. W. Cho, H. S. Min, K. M. Kim, G. J. Yeom et al., 2013 The expression of tumor-associated macrophages in papillary thyroid carcinoma. Endocrinology and metabolism (Seoul, Korea) 28: 192-198.

Koong, A. C., N. C. Denko, K. M. Hudson, C. Schindler, L. Swiersz et al., 2000 Candidate genes for the hypoxic tumor phenotype. Cancer Research 60: 883-887.

Kurahara, H., S. Takao, T. Kuwahata, T. Nagai, Q. Ding et al., 2012 Clinical Significance of Folate Receptor Beta-expressing Tumor-associated Macrophages in Pancreatic Cancer. Annals of Surgical Oncology 19: 2264-2271.

Lan, C. Y., X. Huang, S. X. Lin, H. Q. Huang, Q. C. Cai et al., 2013 Expression of M2-Polarized Macrophages is Associated with Poor Prognosis for Advanced Epithelial Ovarian Cancer. Technology in Cancer Research & Treatment 12: 259-267.

Lewis, J., R. J. Landers, R. D. Leek, K. Corke, A. L. Harris et al., 1997 Role of macrophages in tumor angiogenesis: Regulation by hypoxia. Journal of Pathology 182: A1-A1.

Lewis, J. S., R. J. Landers, J. C. E. Underwood, A. L. Harris and C. E. Lewis, 2000 Expression of vascular endothelial growth factor by macrophages is up-regulated in poorly vascularized areas of breast carcinomas. Journal of Pathology 192: 150-158.

Li, X., H. Kimura, K. Hirota, H. Sugimoto and H. Yoshida, 2005 Hypoxia reduces constitutive and TNF-alpha-induced expression of monocyte chemoattractant protein-1 in human proximal renal tubular cells. Biochemical and Biophysical Research Communications 335: 1026-1034.

MacKie, R. M., B. Stewart and S. M. Brown, 2001 Intralesional injection of herpes simplex virus 1716 in metastatic melanoma. Lancet 357: 525-526.

Martinez, F. O., S. Gordon, M. Locati and A. Mantovani, 2006 Transcriptional profiling of the human monocyte-to-macrophage differentiation and polarization: New molecules and patterns of gene expression. Journal of Immunology 177: 7303-7311.

Mogensen, T. H., and S. R. Paludan, 2001 Molecular pathways in virus-induced cytokine production. Microbiology and Molecular Biology Reviews 65: 131-+.

Mukhtar, R. A., A. P. Moore, V. J. Tandon, O. Nseyo, P. Twomey et al., 2012 Elevated Levels of Proliferating and Recently Migrated Tumor-associated Macrophages Confer Increased Aggressiveness and Worse Outcomes in Breast Cancer. Annals of Surgical Oncology 19: 3979-3986.

Example 3

Isolation and Culture of Human Macrophages

Mononuclear cells were isolated from platelet-depleted buffy coats (Blood Transfusion Service, Sheffield, UK) using Ficoll-Paque Plus (Amersham Pharmacia, St. Albans, UK) and monocyte-derived macrophages (MDM) prepared as described previously[21,22].

Endothelial Cell Cultures

Human Umbilical Vein Endothelial Cells (HUVEC) were seeded for 24 h onto collagen-coated (0.1 mg/ml, human type IV) membranes containing a 5 µM pore PET membrane (Neuroprobe).

Human Multi-Cellular Tumor Spheroids

Human prostate cancer cell line, LNCaP, were seeded ($5 \times 10^3$) in 100 ul medium into each well of a 2% agarose (Sigma, Dorset, UK) coated 96-well tissue culture plate. After 7-10 days, each well contained a tumor spheroid with an average diameter of 700-800 um[21].

Infection of Primary Macrophages

Day 3 MDMs were infected with a replication deficient adenovirus (CMV-AdV5-GFP (driven by a CMV promoter). Virus optimization and GFP expression levels are described in[21].

Cellular Uptake of Magnetic Nanoparticles by Macrophages

MDMs (infected with AdCMV-GFP) were cultured overnight with 100 ug/ml SPIOs (25 nm) (Sigma-Aldrich, Poole, UK). SPIO accumulation in cells was previously assessed by flow cytometry and confirmed by attraction of the cells towards a magnet placed at the side of the culture dish as observed by light microscopy as described in Muthana, M. et al. A novel magnetic approach to enhance the efficacy of cell-based gene therapies. Gene Ther (2008). Cell viability following SPIO uptake by macrophages was also measured and compared to cells that were not incubated with SPIOs using the DNA dye propidium iodide (PI). No statistically significant difference was observed between the two groups p=0.4 (FIG. 20c) N=3.

In Vitro Trans-Endothelial Flow Assay

Figure 20A:
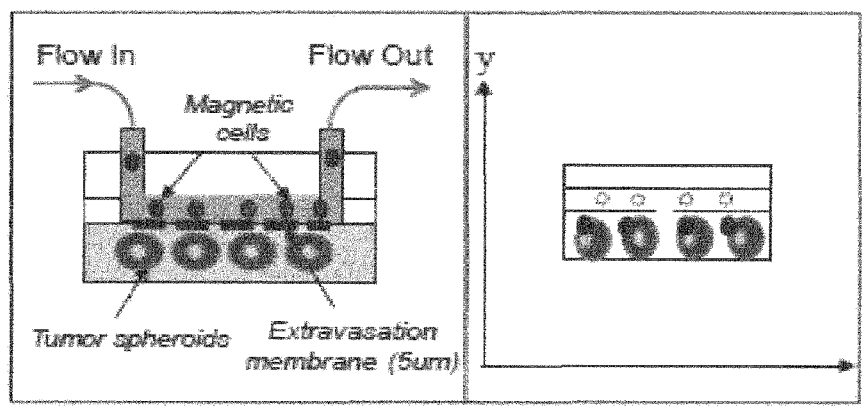
FIGS. 20A-C. Initial MRT investigations using a novel trans-endothelial migration (TEM) flow assay. A flow chamber that can accommodate 3D tumor spheroids as well as a vascular endothelial layer was designed. The flowing 'magnetic cells' will therefore need to cross the vascular barrier before entering a 3D tumor simulating the passage of cells across endothelial cells in a blood vessel wall (A:Left Panel). The TEM flow chamber is placed in the iso-centre of an MRI scanner with a spherical (6 mm diameter) homogenous 7 T magnetic field. A pulsed gradient (50% of max) with strength of 300 mT/m in the (−y) gradient direction was applied. The resulting heterogeneous magnetic field (dB/dy field) can steer magnetic particles towards the tumor spheroids for increased uptake (A:Right panel). (B) Graph showing the effect of the SPIOs on cell death; Uptake was confirmed by a distortion in the MRI image and a loss of signal compared to when no MRT was applied (Ci). Corresponding fluorescent images of whole spheroids infiltrated with macrophages carrying a reporter adenovirus (AdCMVGFP) are shown in (Cii). Flow cytometry of enzymatically dispersed spheroids revealed that the number of magnetic-cells infiltrating spheroids (% of all cells present in spheroids that were CD14+) was significantly (*P<0.03) increased when a gradient was applied (Ciii &iv). Data are Means±SEM and are representative of 6 replicate experiments. Statistical significance differences p=0.0001, compared with MRT treated cells. Bar=100 um.
Figure 20B:
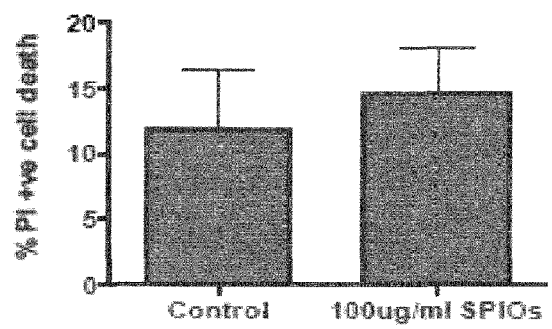

The trans-endothelial migration (TEM) chamber was assembled as shown in (FIG. 20a). SPIO-loaded MDM ($1.5 \times 10^5$ cells/mi in PBS+2% FCS) were allowed to flow over the HUVEC monolayer at typical venous flow rates (1.1885 ml/min) at a sheer stress of 1.4 Dynes/$cm^2$, this is equivalent to blood flow through post-capillary venules. The TEM chamber was positioned directly in the iso-centre at ~5 mm distal of a 7 Tesla magnet (Bruker BioSpecAVANCEII, 310 mm bore, MRI system B/C 70/30). The flow in the chamber was in the −z direction (in and out of the magnet bore). We used pulsed gradients 2 ms on, 7 ms off as described by Reigler et. al[13]. To steer SPIOs into the chamber containing tumor spheroids we applied a pulsed −y gradient at 50% strength to avoid over-heating (~300 mT/m) for 30 minutes. Post MRT a $^1$H volume resonator (Bruker, 300 MHz, 1 kW max, outer diameter 118 mm/inner diameter 72 mm) allowed capture of MR images (FLASH and RARE).

Spheroid infiltration by MDMs was then assessed using a fluorescent microscope to detect the GFP positive cells and flow cytometry using enzymatically-dispersed spheroids. To determine the iron content within SPIO-loaded macrophages, cell pellets were solubilized in 70% nitric acid for 7-14 days prior to analysis. Iron concentrations were quantified against a calibration standard iron solution (Fischer Scientific, Loughborough, UK) by Atomic Emission Spectroscopy using Varian Vista-M PX[14].

Orthotopic Prostate Xenograft Model

Male CD1 athymic mice were used in these studies (Charles Rivers, UK). One million LNCaP:LUC cells (a kind gift from Professor Magnus Essand, Uppsala Sweden) were mixed 1:1 in Matrigel and injected into the dorsolateral prostate. Tumor size was determined by assessment using bioluminescent IVIS imaging and measuring the daily weights of the mice as described in in Muthana, M. et al. Macrophage Delivery of an Oncolytic Virus Abolishes Tumor Regrowth and Metastasis After Chemotherapy or Irradiation. *Cancer Res*, doi:0008-5472.CAN-12-3056 [pii] 10.1158/0008-5472.CAN-12-3056 (2013). Tumor-bearing mice were used in experiments approximately 14 days following implantation or 21 days in the metastases model when the pulmonary tumors develop following implantation of the tumor cells into the prostate[21].

Use of the MRI Scanner to Direct Cell Movement

Three million MDMs with or without SPIOs were administered via tail vein in 100 µl volume of PBS (n=5), control groups received 100 ul PBS (n=5), or 100 ul PBS containing $3\times10^6$ macrophages without SPIOs (n=5). Immediately after MDM administration mice were anaesthetized with gaseous isoflurane and then secured within a magnet-compatible holding capsule and MR targeting was carried out immediately.

Mice were split into 2 groups of n=5. Group 1 was a time-matched control without MR targeting and Group 2 underwent 1 hour of MR targeting (see above) with gradients selected for coarse steering to the tumor site for the Prostate (−z, −y). For steering to the lungs (+z and −y gradients), the absence of an x gradient should ensure even distribution of magnetic particles in each lung.

The force on magnetically labeled cells is dependent on whether the SPIOs have become magnetically saturated. When unsaturated, the force is dependent on the magnetic susceptibility of the SPIOs, the magnetic field and also the magnetic field gradient (Pankhurst, Q. A., Connolly, J., Jones, S. K. & Dobson, J. Applications of magnetic 443" nanoparticles in biomedicine. *J Phys D Appl Phys* 36, R167-R181, (2003)).

However once the SPIOs reach saturation, the force is no longer dependent on the magnetic susceptibility of the particle but the saturation magnetization and as such only the magnetic field gradient will affect the force applied to the cells (Riegler, J. et al. Targeted magnetic delivery and tracking of cells using a magnetic resonance imaging system. *Biomaterials* 31, 5366-5371, (2010).) SPIOs typically reach magnetic saturation well below 1 T, for example in Riegler et al. 2013, where the SPIOs become saturated at around 300 mT, therefore MRT is feasible on clinical MRI systems provided the same magnetic field gradient is used ~300 mT/m.

Following MRI-steering, high-resolution RARE and FLASH images of the tumor (prostate only) were taken. Once complete relaxometry-using MSE and MGE was performed to assess the transverse relaxation rates. After treatment, animals were sacrificed and tissues including tumors, kidney, liver, lungs and spleen, were either paraffin wax embedded and fixed for immunohistochemistry or analyzed by flow cytometry to determine macrophage uptake.

Endothelial Cell Cultures

Human Umbilical Vein Endothelial Cells (HUVEC) were obtained from Promocell, (Heidelberg, Germany) and used in the experiments up to passage 8. Cells (150,000) were seeded for 24 h onto collagen-coated (0.1 mg/ml, human type IV) membranes containing a 5 µM pore PET membrane (Neuroprobe). This resulted in a confluent monolayer of HUVECs on filters as seen by CD31 staining (data not shown).

Infection of Primary Macrophages

Day 3 MDMs were infected with a replication deficient adenovirus (CMV-AdV5-GFP). The E1A/B-deleted adenoviral vectors, CMV-AdV5-GFP (driven by a CMV promoter) was isolated from a single plaque, expanded in 293 human embryonic kidney (HEK) cells All the viruses were purified by double caesium gradient centrifugation, and titered by plaque assay on 293 cells with the titer expressed as plaque forming units (PFU)/cell. Virus optimization and GFP expression levels in macrophages are described in[21].

Flow Cytometric Analysis

Single cell suspensions were obtained by trypsinizing MDMs (including co-transduced MDMs). Cells were then incubated for 30 min at 4° C. with mouse anti-CD14, 1:100 in PBS containing 1% BSA (Sigma) to prevent non-specific antibody binding. Alternatively, spheroids were digested using 0.25% trypsin/EDTA to separate the tumor cells and infiltrated macrophages and cell death was analysed by flow cytometry by adding propidium iodide (Sigma) to the cells immediately before running on the flow cytometer.

Cellular Uptake of Magnetic Nanoparticles by Macrophages

For the nanoparticle cellular uptake studies, MDMs (infected with AdCMV-GFP) were cultured overnight with magnetic nanoparticles 100 µg/ml SPIOs (25 nm) (Sigma-Aldrich, Poole, UK). MNP accumulation in cells following incubation with SPIOs was assessed by flow cytometry, this included measuring cell viability with propidium iodide (PI) as described by us[14] and confirmed by attraction of the cells towards a magnet placed at the side of the culture dish as observed by light microscopy (Leica Microsystems UK Ltd).

HSV1716 Virotherapy

For therapeutic studies LNCaPs or macrophages were infected with HSV1716GFP (an HSV1716 variant with a GFP expression cassette inserted in the deleted ICP34.5 loci) at a multiplicity of infection (MOI) of 5 or 50. Cell death was assessed by flow cytometry 96 h post infection using PI staining. Viral particles were detected in clarified supernatants of infected macrophages using a titration assay on Vero cells to determine plaque-forming units.

Mice received tail vein injections of either 3 million MDM alone or armed with HSV1716 at MOI 50, $1\times10^7$ pfu HSV1716 only or PBS (n=5 mice/group). Of note, 3 groups of mice were administered MDM+OV, one group underwent MRT for 1 h, one sat in the MRI scanner for 1 h but had no MRT (MDM+OV no MRT) and another group did not enter the MRI scanner (MDM+OV). Tumor size was monitored by IVIS Lumina II imaging (IVIS, Caliper Life Sciences). Animals were sacrificed once tumors reached the maximum volume permitted by UK Home Office Regulations, and 1 hour before sacrifice, mice were injected intravenously FITC:Lectin (used for detecting tumor vasculature). Of note, mice receiving PBS and MDM only were culled on day 14-post treatment due to large tumor size. All other tumors were removed on day 21. Excised tissues including tumors, kidney, liver, lungs, and spleen were embedded in OCT or paraffin wax for histologic labeling studies.

Analysis

Tissues were divided into two; one part was formalin fixed for immunohistological analysis and the other was dissected free of adherent fibrous and fatty tissue and treated with collagenase.

Flow cytometry: cell viability was determined using LIVE/DEAD Fixable Violet Dead Cell Stain Kit (Invitrogen). All FACS data were analyzed on an LSR II flow cytometer (BD Biosciences) using FlowJo software (Tree Star).

Histology: Five micron sections of all organs were incubated with specific antibodies for target antigens; for the vasculature we used CD31 (1:100), (AbD Serotec) and for macrophages human CD68 (Dako, Ely, UK) at 1:100 and to detect adenovirus we used E1A at 1:50 (Millipore, UK). A biotinylated secondary antibody system was used in conjunction with a streptavidin-conjugated HRP. Peroxidase activity was localised with diaminobenzidine (Vectastain Elite ABC kit, Vector Labs). To detect iron in the tumors (where cell densities were high) sections were stained with Perls Prussian blue and counter-stained with eosin for improved contrast. To detect cancer cells in the lungs all lung sections were stained with Epithelial cell adhesion molecule (EPCAM) or Hematoxylin and eosin (H&E). All immune-localization experiments were repeated on multiple tissue sections and included isotype-matched controls for determination of background staining.

Statistical Analysis

Data are means±SEM. Student's t test were used to analyze the statistical significance of the data. Differences were termed significant a P value of less than 0.05.

Supplementary Methods

Mouse procedures and human monocyte isolation were conducted in accordance with the University of Sheffield Ethics Committee and UK Home Office Regulations under the Animals (Scientific Procedures) Act 1986.

Results

We show that therapeutic cells armed with an oncolytic virus (HSV1716) can be magnetically labeled using superparamagnetic iron oxide nanoparticles (SPIOs) and then steered from the bloodstream into deep target tissues (primary and secondary tumors) using pulsed magnetic-field gradients within a magnetic resonance imaging (MRI) system. Use of this technique resulted in a marked increase in cell delivery to tumors and a significant reduction in tumor burden and metastasis. Our study, therefore, shows that clinical MRI scanners could be used, not only to image such magnetically labelled cells after their injection into the body, but also to steer them specifically to one or more target sites within the body. We describe the use of magnetic resonance targeting (MRT) to increase delivery of macrophages to tumors.

Figure 16:
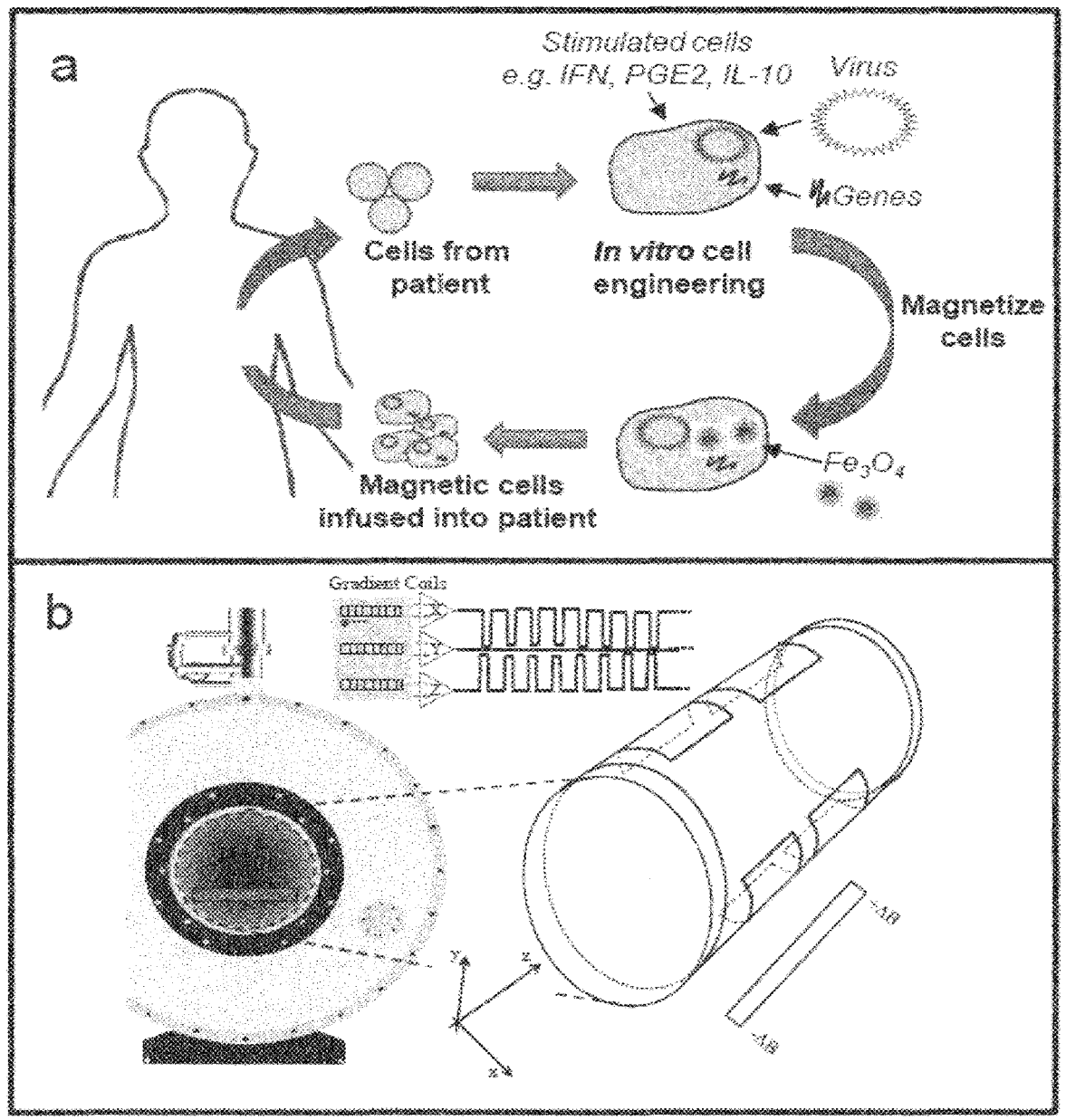
FIG. 16. Possible use of MR targeting to steer cell-based therapies to specific tissues in patients. (a) Schematic illustration: The cells used for these studies are derived from monocytes isolated from patient blood. These cells are cultured in the presence of various stimuli to produce 'therapeutic' macrophages (e.g. cytokines, therapeutic genes or viruses) and loaded with superparamagnetic iron oxide particles (SPIOs) before re-infusion back into the same patient. (b) Schematic illustration: The subject is then placed in the centre of an MRI scanner where linear spatial encoding magnetic gradients can be used to induce a force on a magnetized body. The magnetic cells injected into the bloodstream of the subject circulate and are targeted into the diseased organ/tissue under the influence of the applied magnetic field. Field map plots demonstrate that significant field gradients can be generated in various directions by the MRI gradient coils. The resulting magnetic field (dB/dy field) can steer magnetic cells towards the diseased tissue for increased cell uptake.

We show that it is possible to manipulate the spatial field gradient coils of the MRI scanner to shape the magnetic field in/around a tumor, thereby non-invasively steering magnetically labeled cells towards it (FIG. 16).

We previously showed that such MRT could be used to both image and move cells in an in vitro vascular bifurcation model (a 2D tube that mimics arterial bifurcation)[13]. Here, we show that MRT can also be used to 'steer' magnetic macrophages in vivo—i.e. from the bloodstream into two target organs, orthotopic prostate tumors and their pulmonary metastasis in mice. We have used macrophages as an example of a cellular vehicle as these cells are highly phagocytic allowing them to readily consume SPIOs whilst retaining their magnetic properties[14,18,19]. Such bone marrow-derived cells are increasingly being used in cell-based therapies for such diseases as cancer[20-22], infarcted myocardium[23], spinal cord injury[24], cerebral ischemia[25], degenerative diseases like Parkinson's Disease[26] and Alzheimer's Disease[27].

Before applying MRT techniques in vivo we first established that a pre-clinical 7 T MRI system fitted with a 600 mT/m gradient coil set could generate substantial actuation forces on magnetic macrophages in vitro by steering them across an endothelial layer into 3D human tumor spheroids (MTS). To do this, we designed a trans-endothelial migration (TEM) flow chamber in which human macrophages circulated across the surface of a perforated membrane coated with a layer of human vascular endothelial cells, thereby mimicking flow in tumor venules. MTS were cultured in a non-adherent chamber below the membrane (FIG. 20a). Human macrophages transfected to express a GFP reporter adenovirus (Ad-CMV-GFP) were loaded with SPIOs (1.18 ug/ml±0.3)[14] and then steered across the membrane into MTS when the chamber was placed in the iso-centre of a high-field (7 T) pre-clinical MRI system.

Figure 20C:
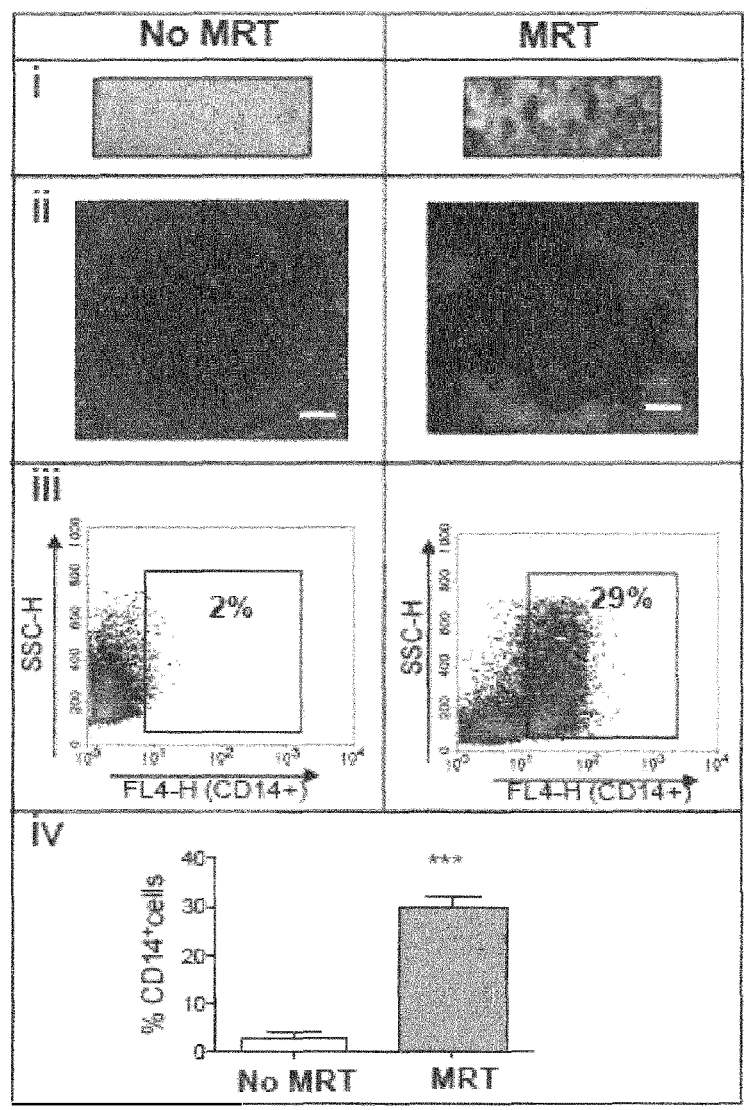

MRT experiments used a pulsed magnetic field gradient (2 ms on, 7 ms off, 50% strength ~300 mT/m[13]) for 1 hour in the direction of the spheroids (FIG. 20a) with an effective additional magnetic field offset, $B_{off}$~+1.5 mT around the MTS site. In control conditions samples were exposed to the magnetic field of the scanner but gradients were not pulsed. Using MRT, we found a $T_2^*$-weighted signal loss indicating higher concentration of iron in comparison to the control samples for MRT exposed samples (n=6) (FIG. 20ci) and GFP-expressing macrophages were clearly visible within MTS (FIG. 20cii). Flow analysis further confirmed macrophage uptake with significantly (P=0.0001) more viable infiltrating $CD14^+/PI^-$ expressing macrophages with MRT (29.7%±2.6) than without (2.9%±1.8) (FIG. 20c iii-iv).

We then investigated whether such an MRI gradient system could be used to steer magnetic macrophages to tumors in vivo (FIG. 17). Three million SPIO-loaded macrophages were administered intravenously to mice bearing orthotopic primary and metastatic (lung) prostate tumors. A pulsed magnetic field gradient[13] was applied for 1 hour, in the direction of the prostate (FIG. 17a), with an effective magnetic field offset, $B_{off}$~+7 mT on top of the static magnetic field of the scanner ($B_0$=7 T). The control group were exposed to the static magnetic field of the scanner in the absence of the steering gradients (no MRT).

Figure 17A:
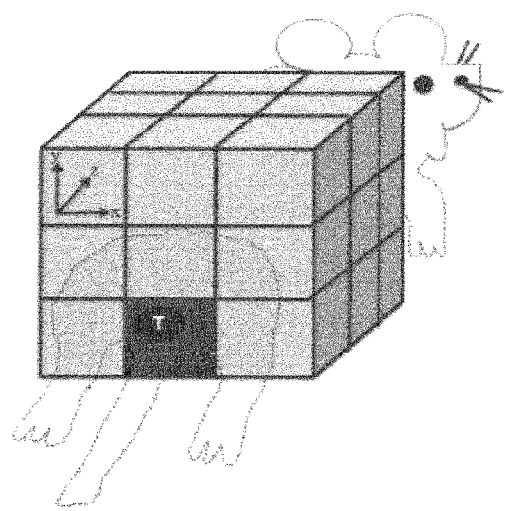
FIGS. 17A-E. Magnetic macrophages were steered into primary prostate tumors using MR Targeting. (a) Schematic of targeted regions using imaging gradients for MR Targeting. A-Y gradient is applied equally across the animal to target the location of the prostate as depicted (darkly shaded box). Three million magnetically labelled macrophages were then administered to mice via i.v. injection and anesthetised mice were then placed into the isocentre of a 7 T MRI scanner. Subjects were split into 2 groups. Group 1 were imaged after 1 hour (no MR Targeting). Group 2 underwent MRI targeting. Post mortem the increased levels of human macrophage uptake was confirmed by (b) FACS analysis of collagenase-treated tumors one hour after MRI targeting, and (c) histological staining of paraffin wax-embedded tumor sections with an anti-human CD68 antibody and Prussian blue (for SPIOs). Representative RARE images and R2 maps for each group are shown (d) and (e). Bars=200 µm.
Figure 17B:
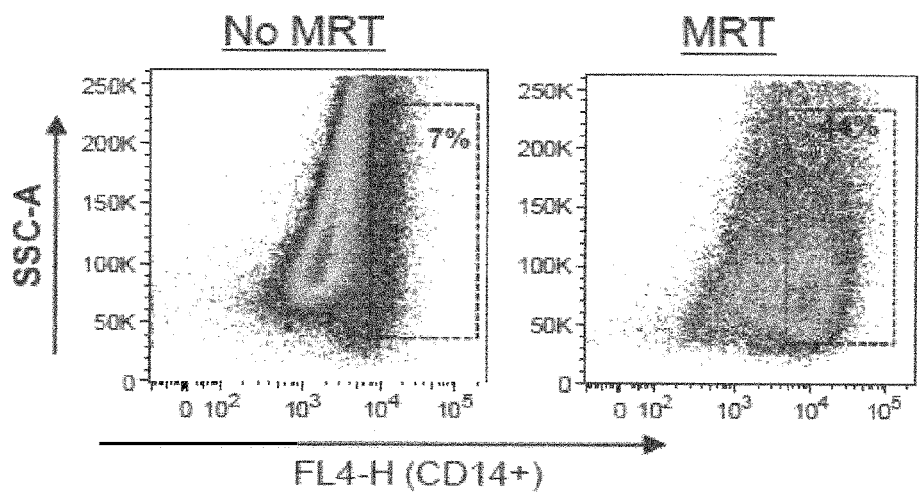
Figure 17C:
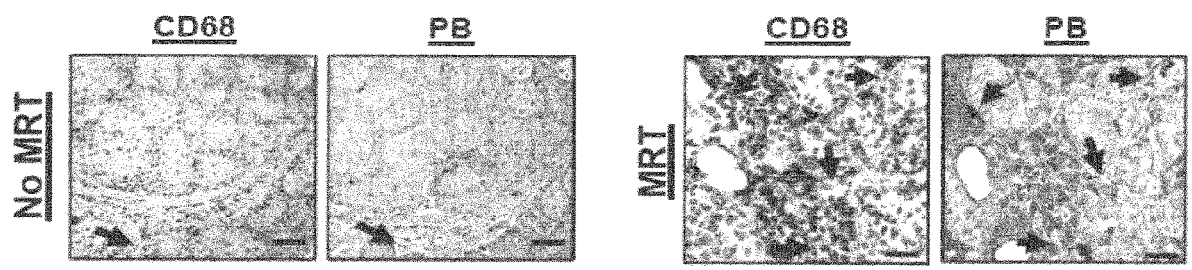
Figure 17D:
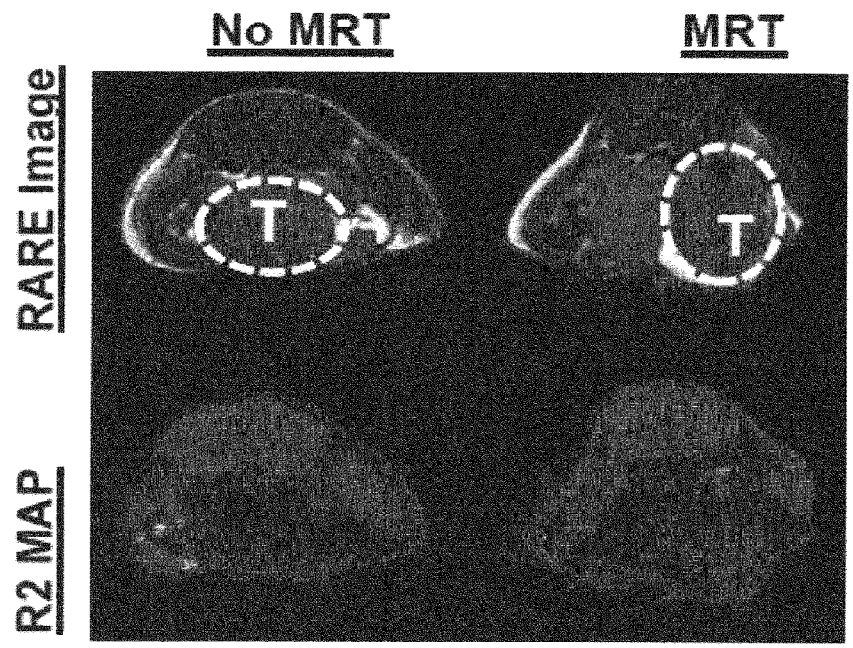
Figure 17E:
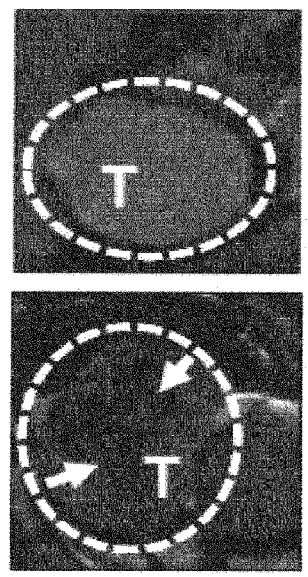
Figure 21A:
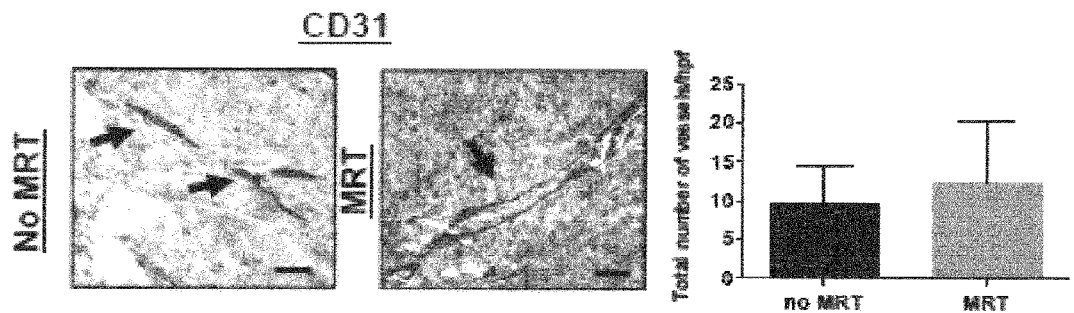
FIGS. 21A-D. Magnetic macrophages were steered into primary prostate tumors using magnetic fields generated in an MRI scanner. Three million magnetically labelled macrophages were administered via i.v. injection and mice were then placed into the isocentre of a 7 T MRI scanner. Subjects were split into 2 groups. Group 1 were imaged after 1 hour (no MRT). Group 2 underwent MRT. The number of vessels per high power field per view was recorded in sections of CD31 labelled tumors (a). Steering of macrophages into the tissue using MRT had no significant effect on vessel numbers in tumors (p=0.5165) compared to mice who received no MRT. Representative MRI images for each group following MRT into tumors show a qualitative decrease in signal and this was confirmed by analysis of the transverse relaxation rate in both groups (b). Group 2 shows an increased decay rate over group 1. The estimated best echo time for looking at signal differences with MRI is around 60 ms—MRI steering leads to a 10% decrease in signal at this echo time. This significant signal decrease suggests the presence of increased levels of iron in-group 2. The normal decay rate of tumor tissue is also shown for comparison (Control). This experiment was repeated but using macrophages without SPIOs (N=3 mice per group). Very little distortion was visible in the MRI images of tumors in (c), indicating low uptake of nonmagnetic macrophages and this was confirmed by FACS analysis of collagenase treated tissue (d). Data are presented are the means±SEM. Bar=200 um.
Figure 21B:
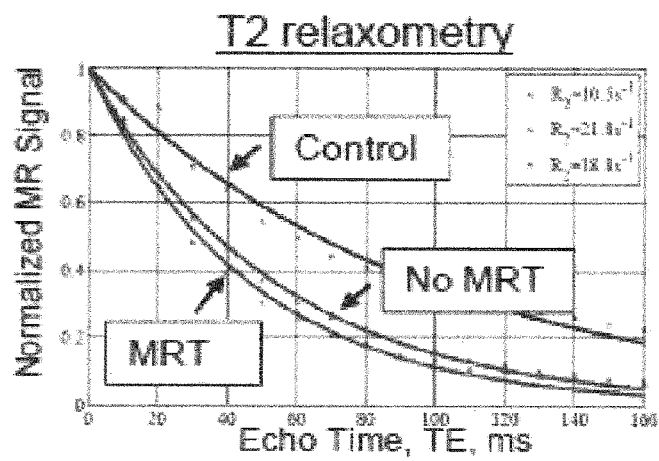

MRT significantly (p=0.0001) increased uptake of SPIO-loaded macrophages in primary prostate tumors (42.2%±2.5) compared to the control group (7.17%±0.8) (FIG. 17b). Moreover, these cells were present throughout tumors, with very few signs of cell clumping in the tumor vasculature following MR targeting as seen by labeling sequential sections of tumors using an antibody against human CD68 (a pan macrophage marker) and a histological stain for iron (Prussian Blue or 'PB') (FIG. 17c). MRI steering of macrophages did not adversely affect the tumor vasculature (FIG. 21a) and in the multi-echo RARE MR images of tumors little difference can be seen between the MRT and no MRT groups (FIG. 17d). This is most likely due to the blood pool iron content per voxel. However, a marked difference between SPIO injected and non-injected subjects is evident in the T2-weighted long TE images, with loss in signal intensity within the tumor (distorted MRI image with MRT compared to control) indicating the presence of high concentrations of iron (FIG. 17e). In an effort to assess the increased uptake of magnetic macrophages in vivo we used MR relaxometry to measure the MR transverse relaxation decay rate ($R_2$) in tumors in both groups. $R_2$ measurements were $21.8s^{-1}$ for the MRT group and $18.8s^{-1}$ for the control group. Normal $R_2$ decay rate f tumor tissue without the presence of any SPIOs is also included for comparison ($10.5s^{-1}$). A higher decay rate indicated increased iron uptake for the MRT group—suggesting it is possible to assess the uptake with MRI, as seen with the post mortem analysis. The significant difference in $R_2$ values was used to estimate the best echo time for analysing signal differences with spin echo-based MRI sequences at a TE of 60 ms, here MRT leads to a 10% decrease in signal over the time-matched controls.

Figure 21C:
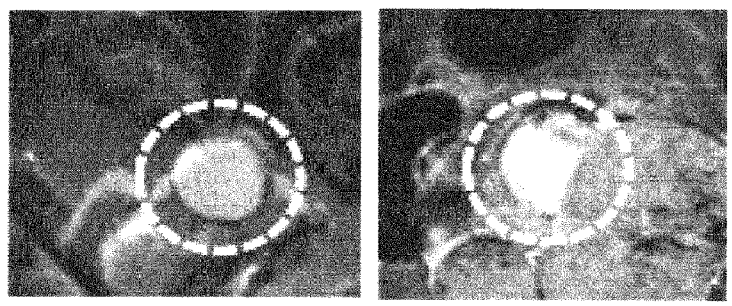
Figure 21D:
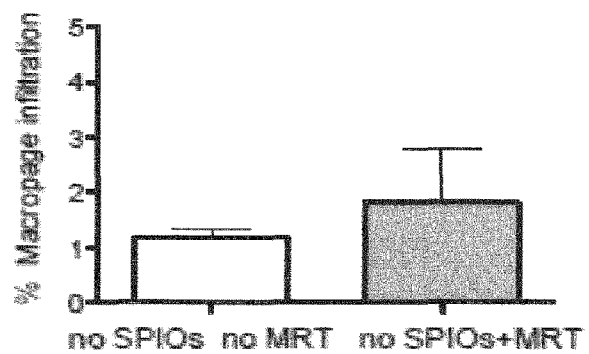
Figure 22:
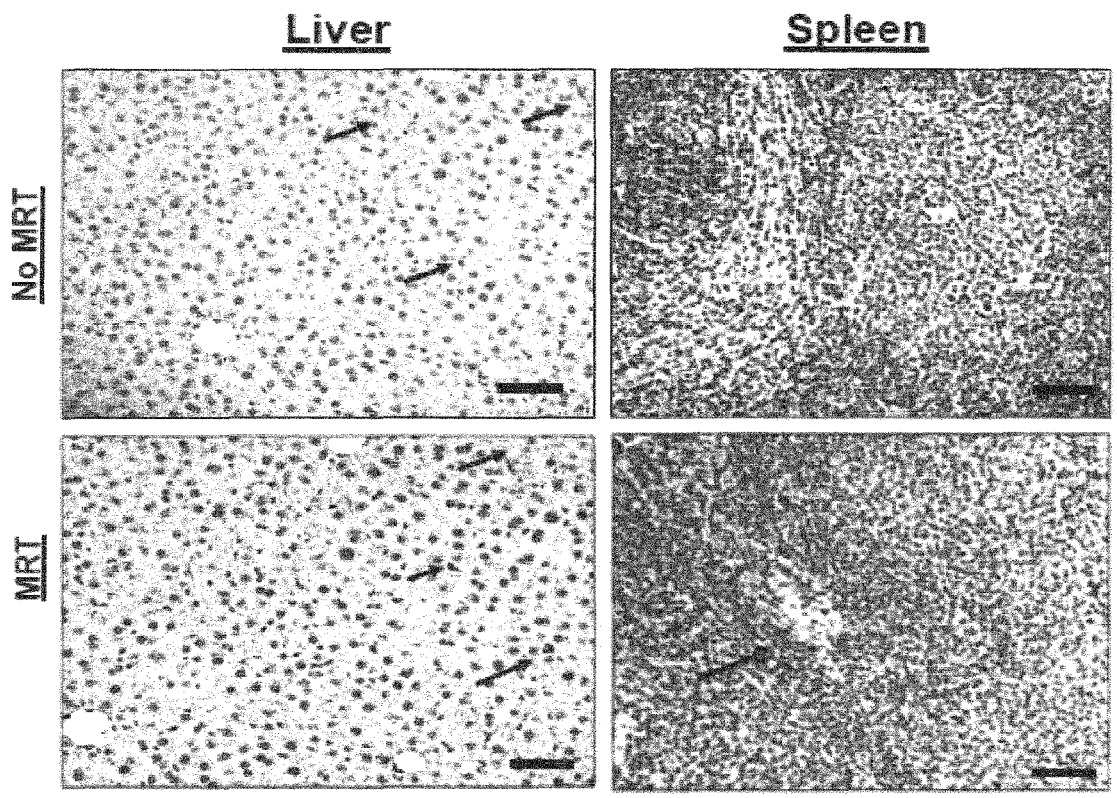
FIG. 22. Magnetic macrophages were detected in very low numbers in other tissues/organs. MRI steering of magnetic macrophages into tumors resulted in very few macrophages localising to other tissues. This was determined by histological staining of paraffin-wax embedded sections of tissues and organs removed post-mortem. Representative sections of the liver and spleen taken from tumor-bearing mice that received MRT or no MRT are shown. In both these tissues few human macrophages (<2%, Liver & <1% Spleen) following staining with anti-CD68 were detected. Bar=100 um FIGS. 23A-B. Magnetic macrophages were steered into areas of pulmonary metastasis using MRT. This was confirmed by histological staining of wax-embedded sequential sections of lung tissue with EPCAM (to detect the human prostate tumor cells) and Prussian Blue (PB) to detect the iron-positive human macrophages. Representative images show that macrophages positive for PB were detected in close proximity to the metastatic deposits within the lungs of mice following MRI steering (a). Of note, the iron with macrophages targeted to the lungs by MRT was also visible following H&E staining (b). Bar=200 um and Bar=50 um.

Additional controls included tumor-bearing mice: (i) with unlabelled macrophages and MR targeting, and (ii) with unlabelled macrophages without MR targeting. For these control groups, we detected very few macrophages within tumors as confirmed by MRI imaging (FIG. 21c) and flow cytometry of enzymatically dispersed tumors (FIG. 21d). Of note, we detected virtually no human CD68+ macrophages in other tissues including the liver (<2% of all cells/tissue section), spleen (<1%) and kidneys (none detected) (FIG. 22).

MRT has particular application when tumors are difficult or impossible to remove surgically, as in the lung, brain, liver or spinal cord. Separate MRT sessions could enable targeting of a cell-based therapy to one or more metastatic lesions in cancer patients. In a second in vivo experiment we steered magnetic macrophages into lungs containing micro-metastases in our tumor-bearing mice. MRT was again used to steer magnetic macrophages towards the lungs following administration of 3 million macrophages. Mice without application of MRT but exposed to the magnetic field of the scanner, for the same length of time were used as a time-matched control.

Figure 18A:
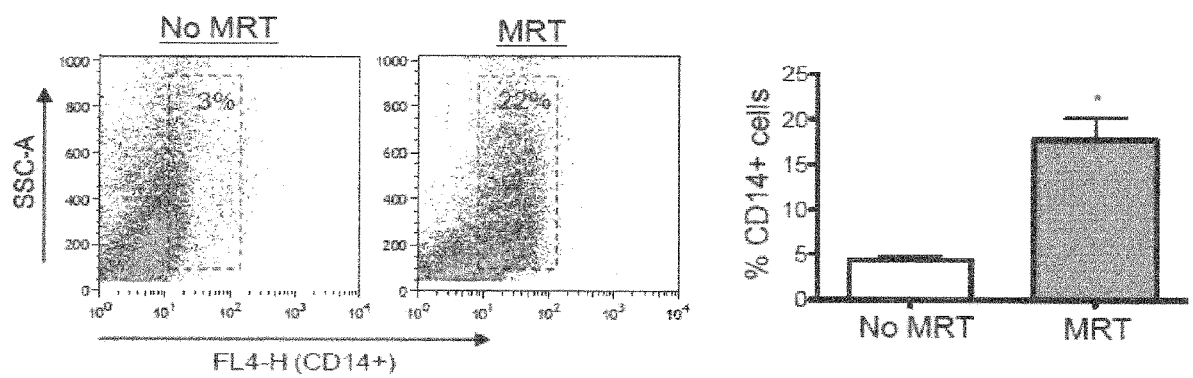
FIGS. 18A-C. Magnetic macrophages were steered in to pulmonary metastasis using MR Targeting. Short-pulsed magnetic gradients were used to steer SPIO-loaded macrophages towards the lungs. (a) FACS analysis of collagenase-treated lungs showed significantly more human CD14+ macrophages were present in lungs with rather than without MR targeting. (b) This was accompanied by increased immunostaining for human CD68 and Prussian blue in lung sections. (c) Immunostaining with CD31 and H&E indicated that MR targeted delivery of magnetic macrophages into the lungs had no adverse affects on the lung vasculature compared to delivery without targeting. Representative data are shown from one of two replicate experiments in which n=3 mice/group. SEMs are depicted. *P<0.01 compared with non-MR targeted lungs in panel A. Bar=50 µm.
Figure 18B:
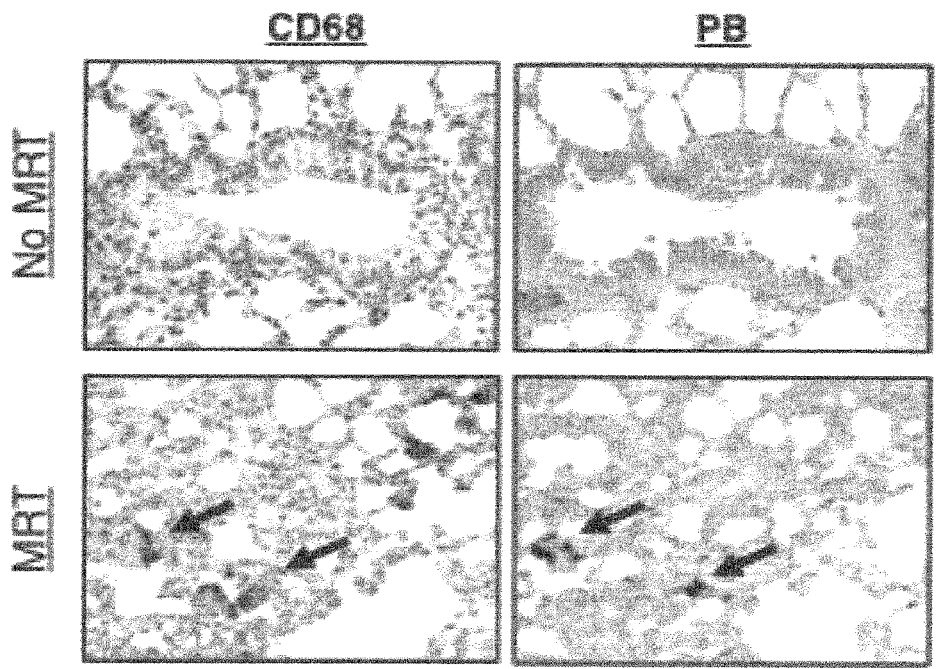
Figure 18C:
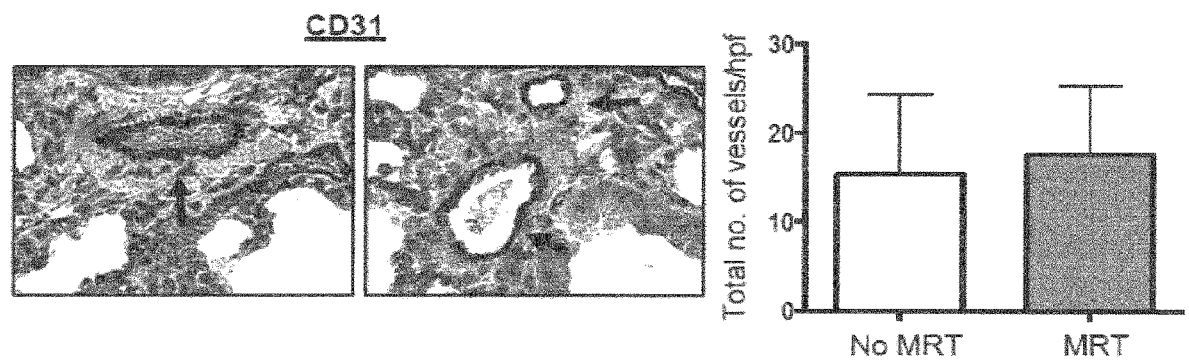
Figure 23A:
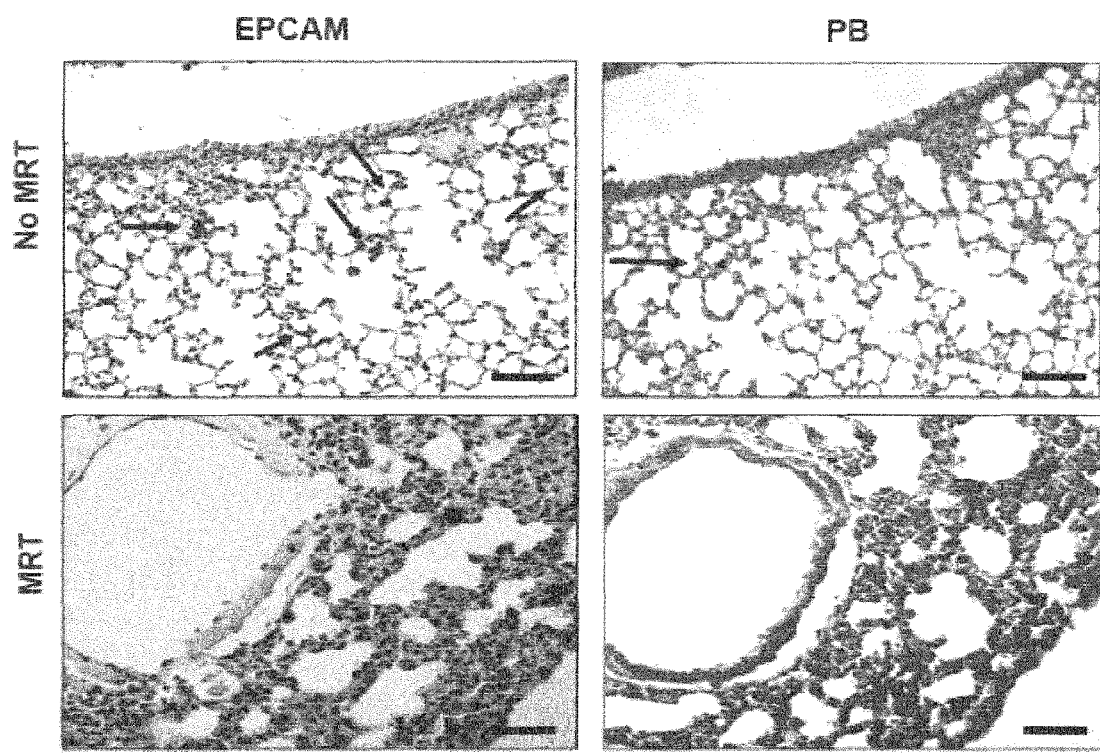
Figure 23B:
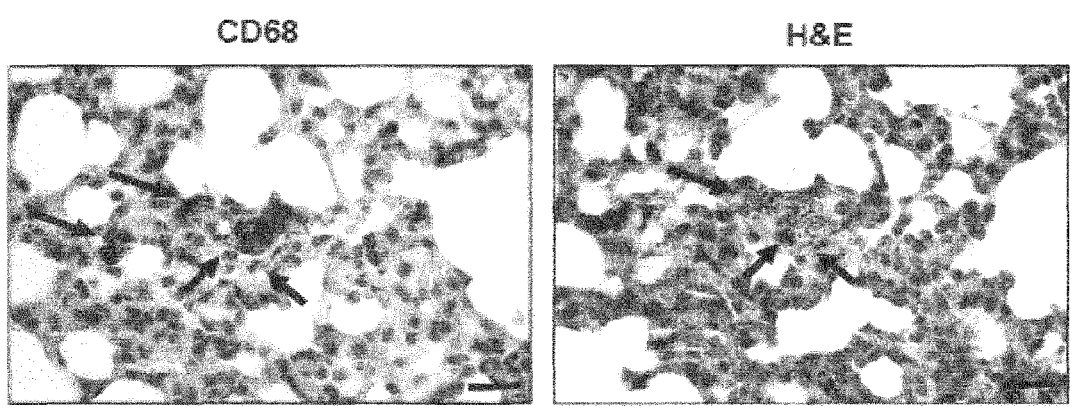

Flow cytometric analysis of enzymatically dispersed lungs showed the presence of significantly more human CD14+ macrophages following MRT than in the control group (17.7%±4 vs. 4.4%±2.6, respectively) (FIG. 18a). This was also confirmed by histological staining of lungs, where CD68+ human macrophages were detected in or close to the metastatic deposits within the lungs of mice following MRT (FIG. 18b and FIG. 23a). These macrophages were also positive for Prussian Blue (FIG. 18c) and their iron content was also visible following H&E staining (FIG. 23b). We inspected the morphology of CD31+ blood vessels in the lungs following their uptake of SPIO-labelled macrophages with or without MRT (FIG. 18c). In addition, we examined every blood vessel in each of the 5 tumors in these 2 groups of mice and found no differences between the two groups. We could not see signs of endothelial cell disruption, nor were there any signs of blood clotting (e.g. platelet aggregation) in, or on the abluminal side of blood vessels after MRI targeting. Due to the short T2/T2* of lung tissue it was not possible to image the lung parenchyma with conventional $^1$H MRI techniques at high field for in vivo validation of increased uptake. Future technical developments may make this possible, for example the use of hyperpolarised gases in the airspaces could be used as an indirect MR signal detection method[28]. Nevertheless, in different organs or soft tissues, or on clinical systems, T2* imaging may have a place."

Figure 19A:
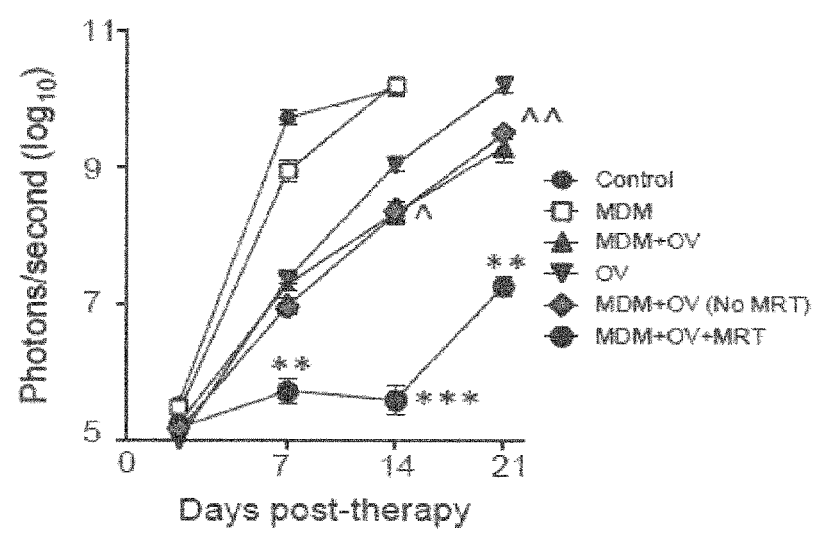
FIGS. 19A-F. Magnetic targeting increases the anti-tumor effects of macrophage virotherapy on human prostate (LUC-LNCaP) tumors. Tumor-bearing mice were administered with a single dose of human monocyte-derived macrophages (MDM) carrying the oncolytic virus, HSV1716 (MDM+OV). These were divided into three groups of mice (each with 5 mice/group). One group underwent MR targeting to either the prostate gland or lungs (MDM+OV+MRT) for 1 h, another was exposed to the MRI scanner but with no MR targeting (MDM+OV no MRT) and the third (MDM+OV) did not enter the MRI scanner. Additional groups of mice received 100 ul of PBS (Control), a single dose of 1×10$^7$ pfu HSV1716 (OV) or 3 million untreated MDM. Mice were imaged weekly using the IVIS imaging system and, after 21 days, tumors and lungs were removed and processed for histology. (a) Tumor luminosity showed MR Targeting significantly improved the effect of OV-MDM on tumor growth (b) Representative IVIS images and photographs of primary tumors following various treatments (c) Representative RARE images for MDM+OV with or without MR targeting show marked difference in tumor size at the beginning and end of therapy (d). Appearance of H&E stained sections to show (e) the presence of necrosis in primary tumors and (f) metastases in the lungs of mice receiving MDM+OV with or without MR targeting. Corresponding data from all groups are shown (e). Data shown are means+/−SEMs. Quantitative analysis was carried out on 10 high-power fields (HPF; ×20 magnification) per tissue section. Statistical significance differences, *P<0.05; P<0.001; *P<0.0001 compared with MDM+OV+MRT to MDM+OV (no MR targeting) and ˆ is comparing MDM+OV (no MR targeting) and free OV group; Bar, 200 µm.
Figure 19B:
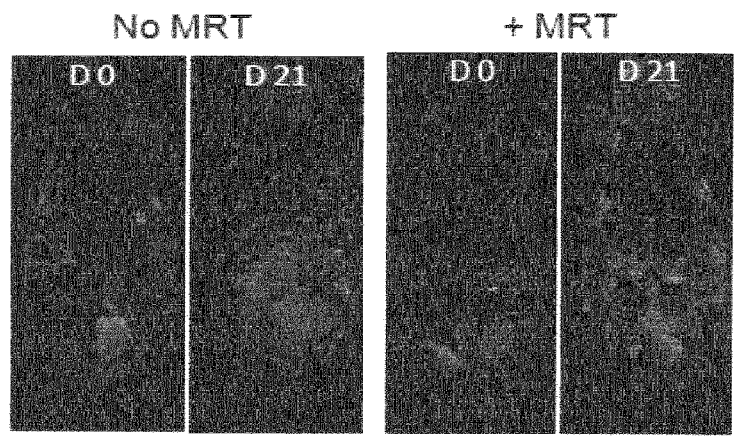
Figure 24A:
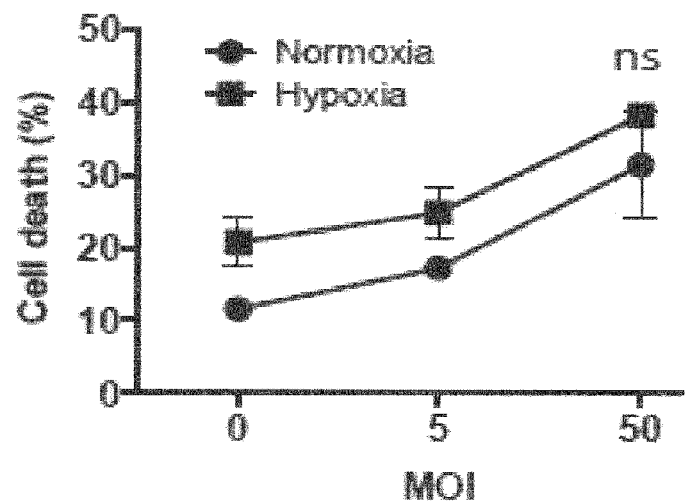
FIGS. 24A-D. Graphs showing HSV1716 induces LNCaP and macrophage oncolysis. HSV1716:GFP was added to cultures of LNCaP cells incubated in normoxic (20% $O_2$) and hypoxic (0.5% 02) culture conditions. Tumour cell death was assessed by flow cytometry using propidium iodide and was significantly increased over uninfected cells (a). This was dose dependent and in normoxia at MOI 5 p<0.03 at MOI 50 p<0.001 & in hypoxia at MOI 5 p<0.01 at MOI 50 p<0.001. No statistical significance was observed between normoxic and hypoxic conditions at both MOI 5 and 50. HSV1716 is effectively taken up by MDM at MOI 5 and 50 as assessed by flow cytometry 48 h post infection. Normoxic culture conditions resulted in significantly more GFP expressing macrophages at MOI 5 (p<0.0004) and MOI 50 (p<0.001) compared to hypoxic conditions (b) but interestingly the concentration of HSV1716 (PFU/ml) detected in macrophage supernatants 96 h following infection was greater at both M015 and 50 in hypoxia compared to normoxic conditions. Finally, macrophage cell death was equally infective in both normoxia and hypoxia (p<0.2) following infection with HSV1716 (c, d). Data are the mean±SEM of n=4 independent experiments.
Figure 24B:
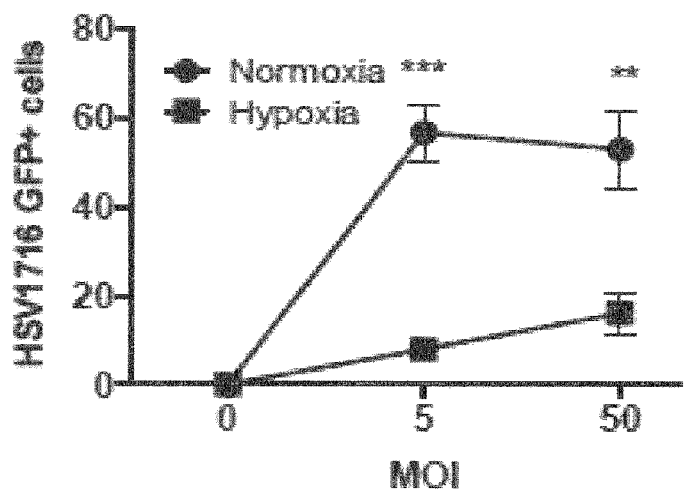
Figure 24C:
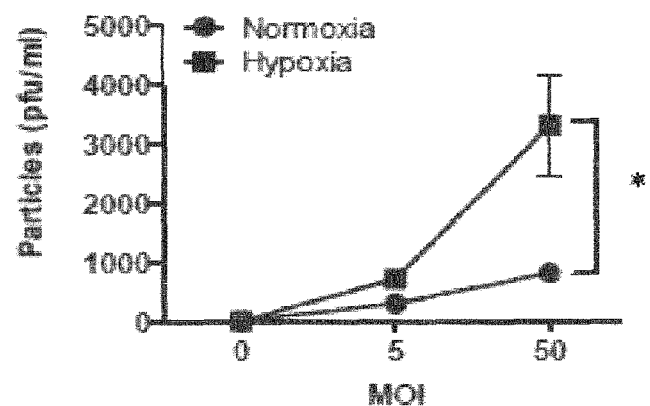
Figure 24D:
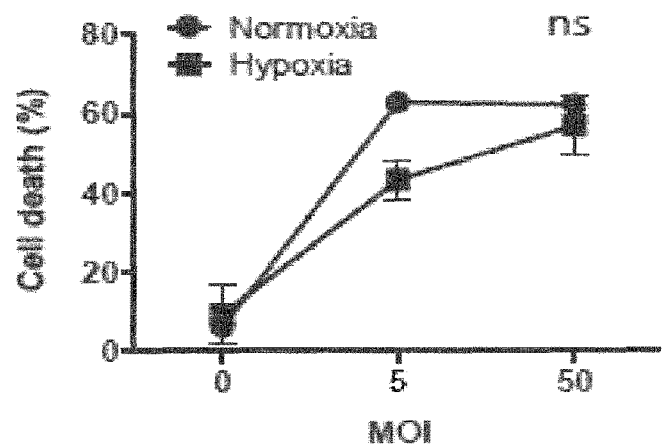
Figure 25A:
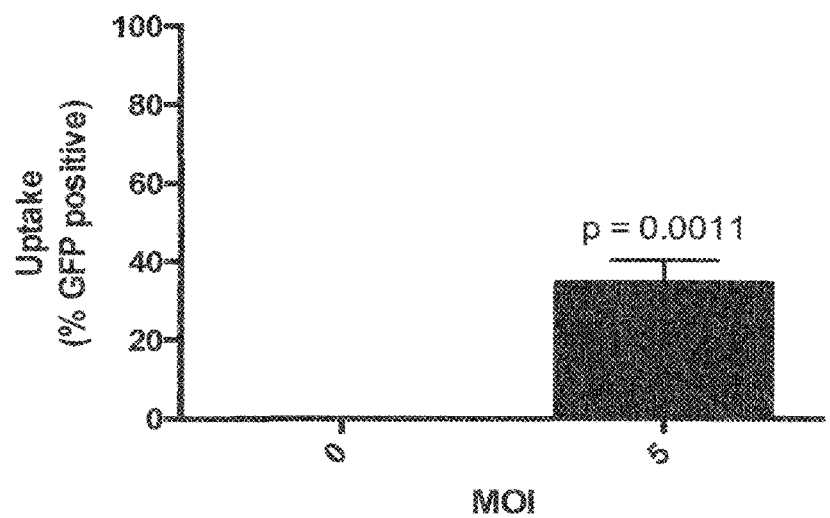
FIGS. 25A-B. HSV1716 infects, replicates in and kills human macrophages. Day 7 human monocyte-derived macrophages infected with GFP tagged HSV1716 demonstrate a significant increase in infection which correlates with an increase in cell death. Charts show (A) infection of human monocyte-derived macrophages, (B) macrophage death. All data were normalised to the house keeping gene GAPDH and 6 independent experiments were performed (n=6). X-axis 0=macrophages (no virus).
Figure 25B:
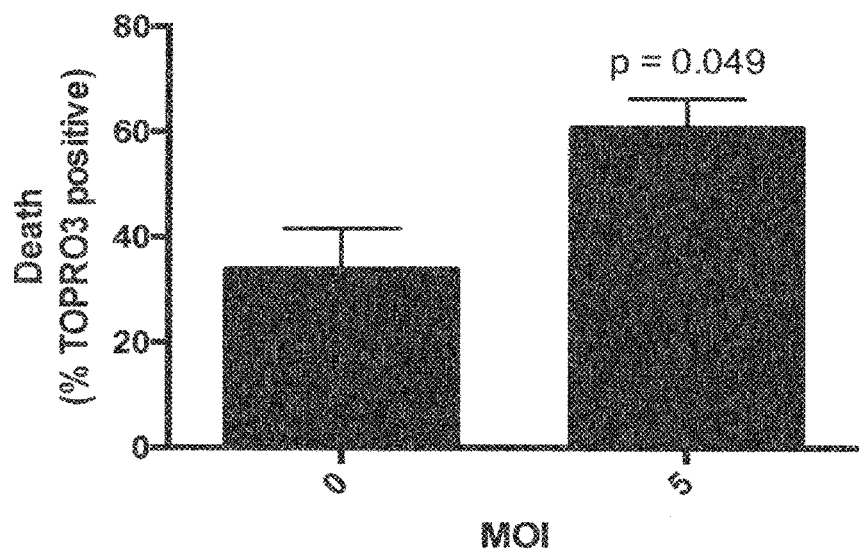
Figure 26A:
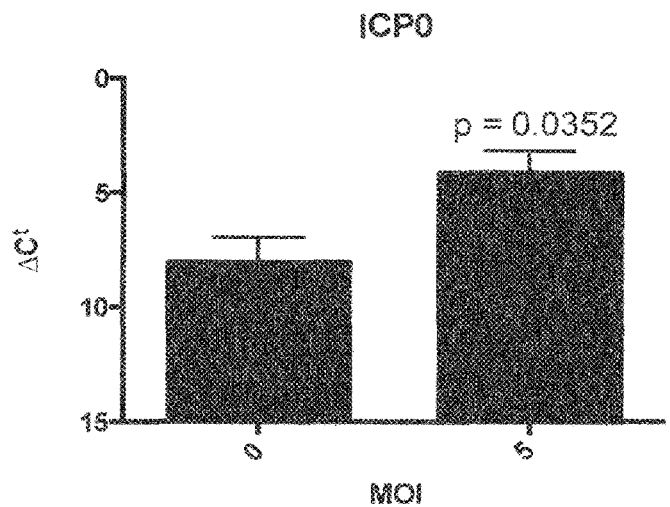
FIGS. 26A-C. HSV1716 replication within human macrophages. Investigation of the expression of viral proteins showed that both immediate early (ICP0) and late (gB) genes required for viral replication demonstrate significant gene expression in macrophages. Charts show (A) ICP0 expression, (B) ICP8 expression, (C) gB expression. All data were normalised to the house keeping gene GAPDH and 6 independent experiments were performed (n=6). X-axis 0=macrophages (no virus).
Figure 26B:
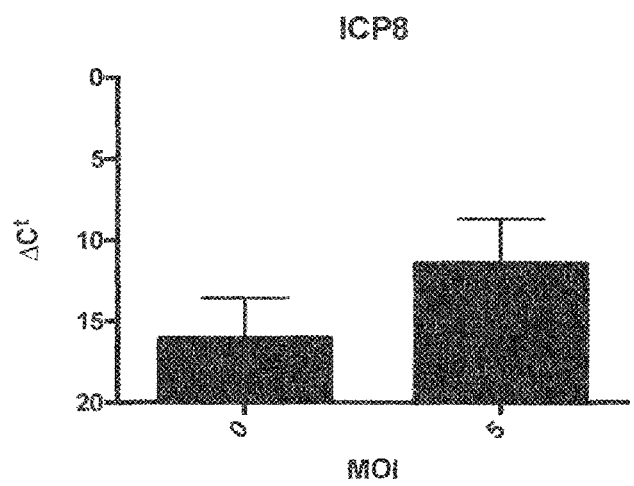
Figure 26C:
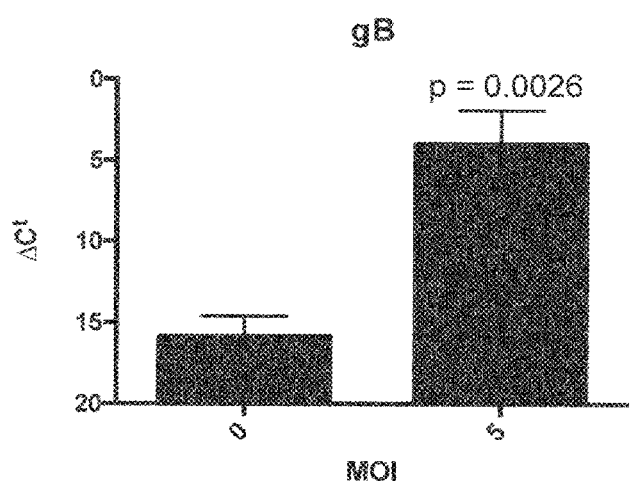
Figure 27A:
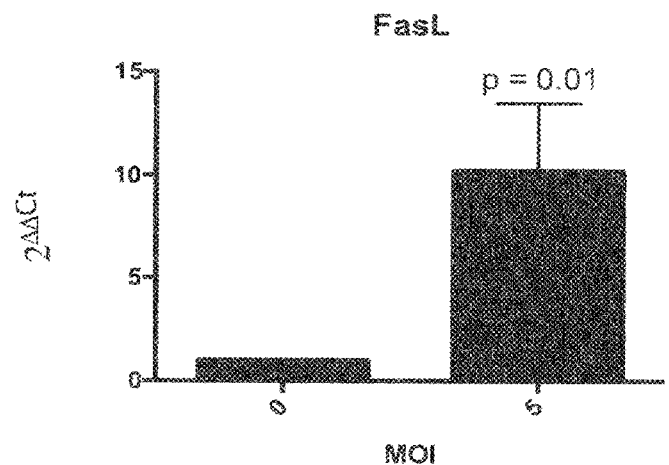
FIGS. 27A-D. Mechanism of cell death in human macrophages. HSV1716 kills macrophages via apoptosis and in a Fas dependent manner with both FasL and Bcl-2 gene expression up-regulated 24 hours after infection with HSV1716 at an MOI of 5. Expression of genes involved in autophagy (Atg5 and LC3B) were not significantly altered. Charts show expression of (A) FasL, (B) Bcl-2, (C) LC3B, (D) Atg5. All data were normalised to the house keeping gene GAPDH and 6 independent experiments were performed (n=6). X-axis 0=macrophages (no virus).
Figure 27B:
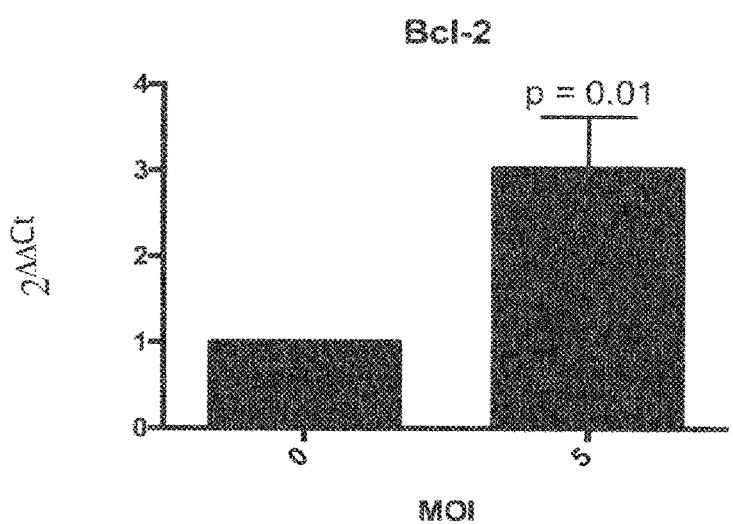
Figure 27C:
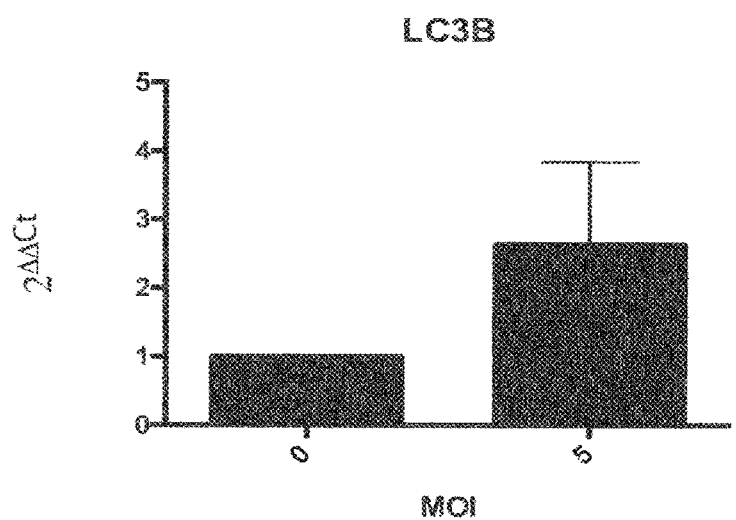
Figure 27D:
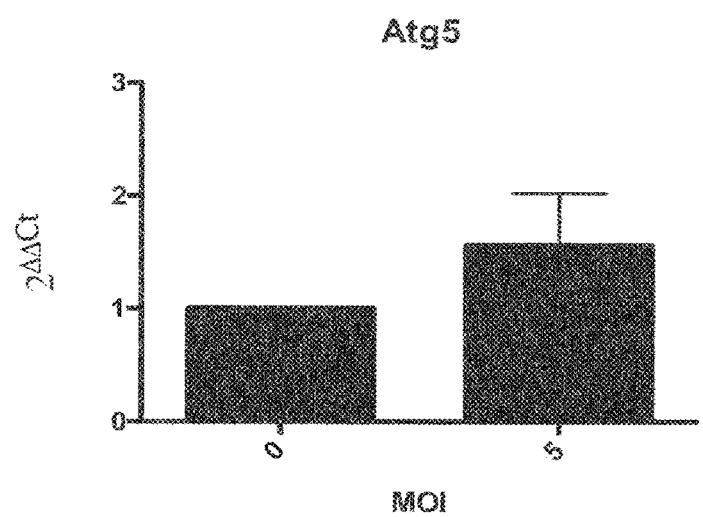
Figure 28A:
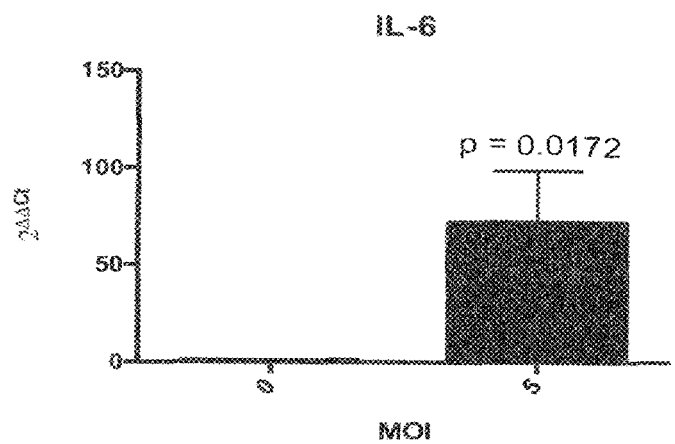
FIGS. 28A-F. HSV1716 infection induces an inflammatory phenotype in macrophages. HSV1716 infection of day 7 monocyte-derived macrophages significantly induces mRNA expression of typical markers of inflammation 24 hours post infection. Charts show expression of mRNA for (A) IL-6, (B) IL-8, (C) IL-10, (D) TNFalpha, (E) TGFbeta, (F) NFkappaB. All data were normalised to the house keeping gene GAPDH and 6 independent experiments were performed (n=6). X-axis 0=macrophages (no virus).
Figure 28B:
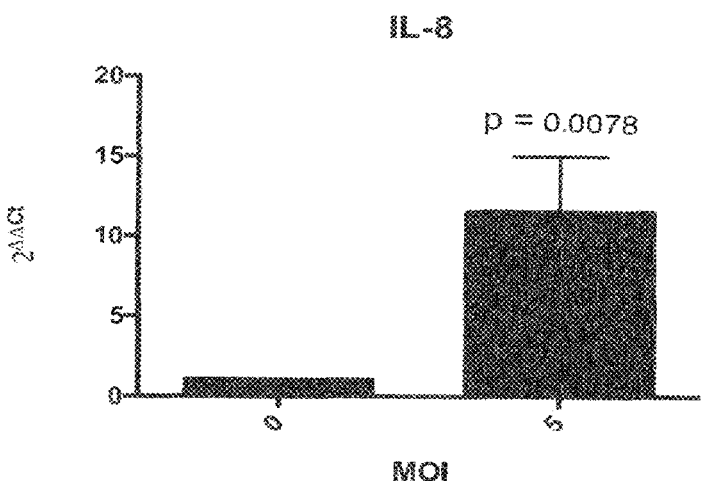
Figure 28C:
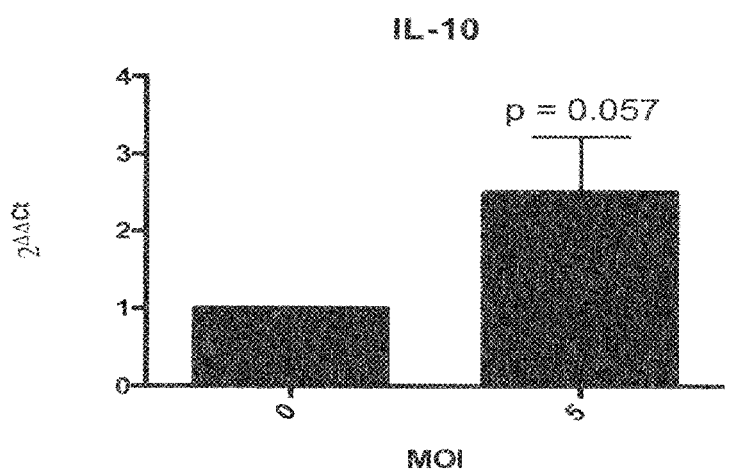
Figure 28D:
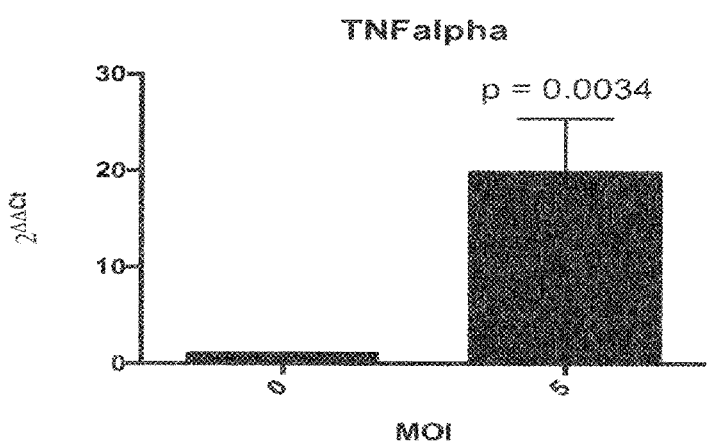
Figure 28E:
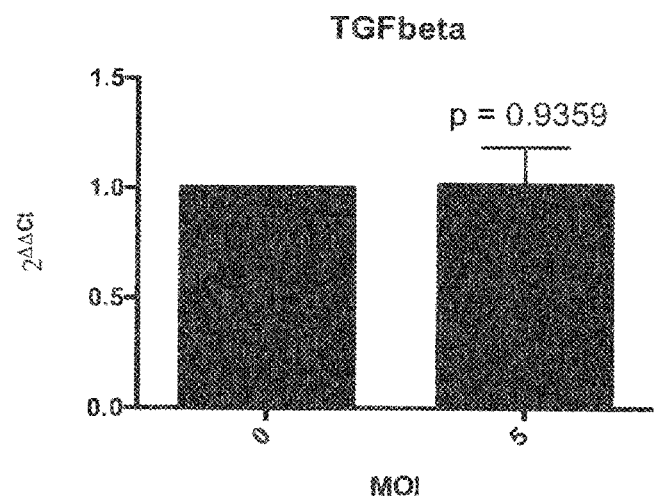
Figure 28F:
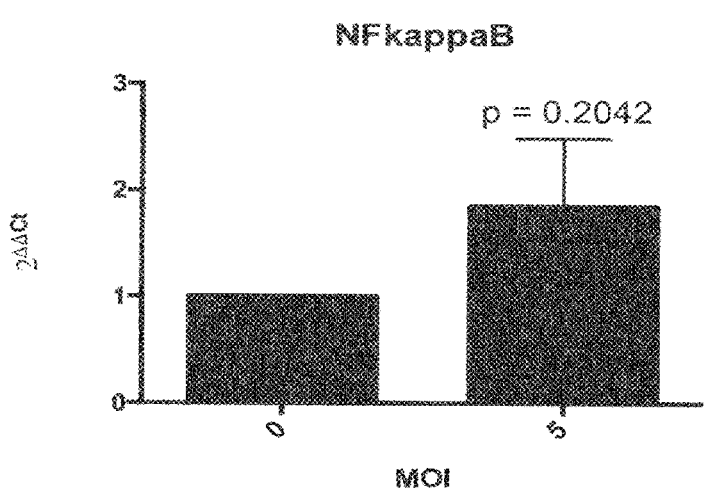
Figure 29A:
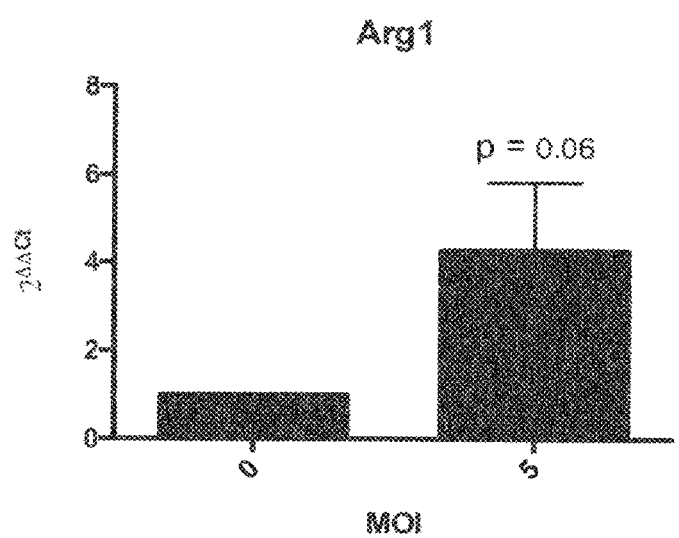
FIGS. 29A-E. HSV1716 infection induces an inflammatory phenotype in macrophages. HSV1716 infection of day 7 monocyte-derived macrophages significantly induces mRNA expression of typical inflammatory M1 macrophage markers (NOS2, CXCL10) and down regulates typical M2 markers expressed by tumour-derived macrophages (MRC1). Charts show mRNA expression of (A) Arg1, (B) Nos2, (C) MRC1, (D) VEGF, (E) CXCL10. All data were normalised to the house keeping gene GAPDH and 6 independent experiments were performed (n=6).
Figure 29B:
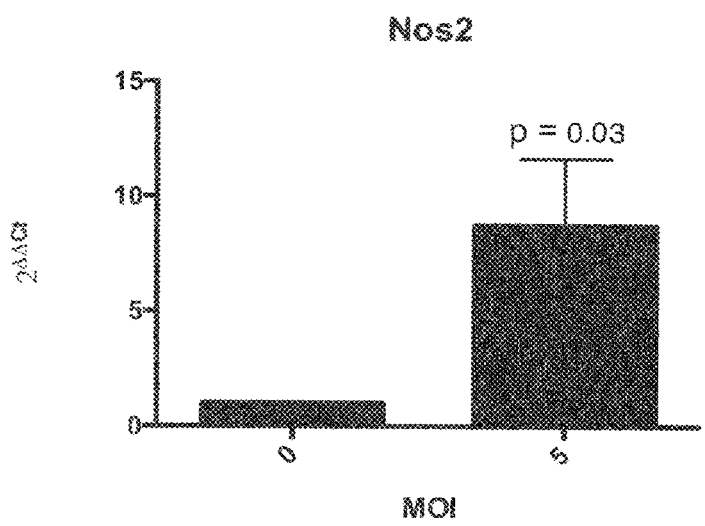
Figure 29C:
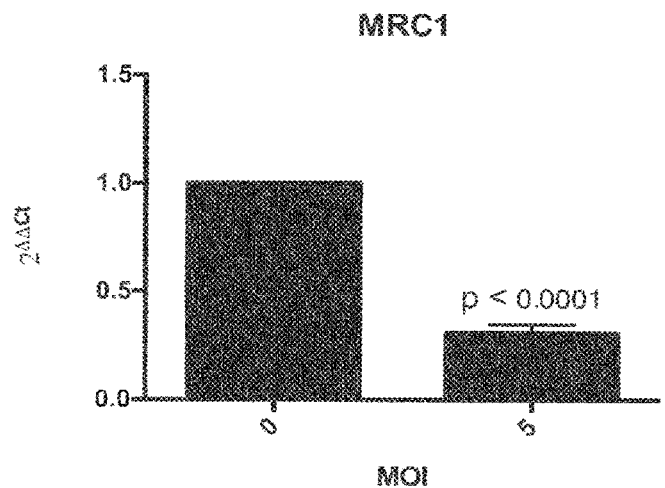
Figure 29D:
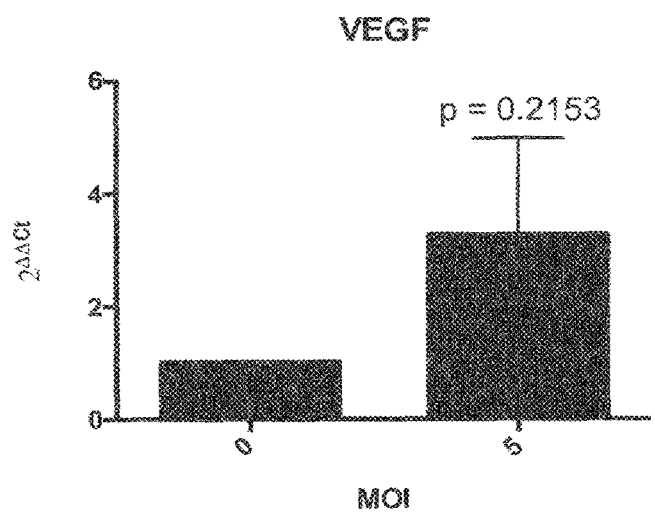
Figure 29E:
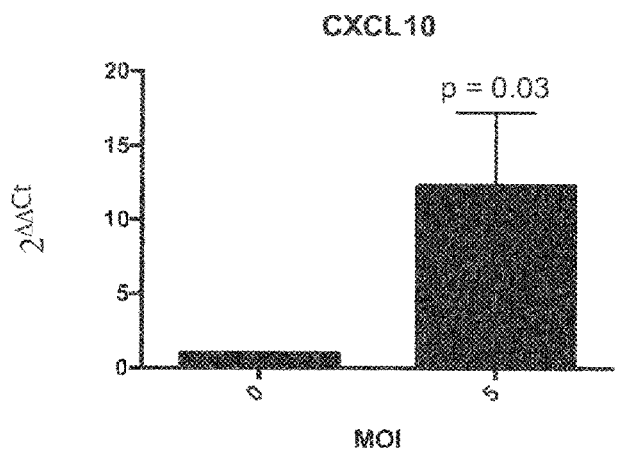
Figure 30:
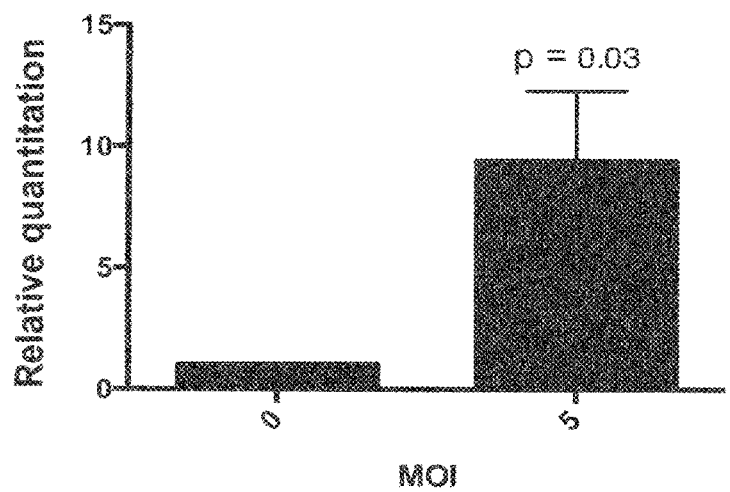
FIG. 30. Chart showing HSV1716 infection induces PCNA expression in macrophages. HSV1716 infection of day 7 monocyte-derived macrophages significantly induces PCNA expression. This is a potential mechanism for inducing viral replication and macrophage cell death in non-tumour cells that are terminally differentiated. All data were normalised to the house keeping gene GAPDH and 4 independent experiments were performed (n=4).

In a final experiment to assess the therapeutic benefits of MRT we targeted SPIO-loaded macrophages armed with the therapeutic oncolytic virus (OV) HSV1716 to tumor bearing mice. HSV1716 replication is supported by PC3 prostate cancer cells {Conner and Braidwood, Cancer Gene Ther. 2012 July; 19(7):499-507} and here we show for the first time oncolysis in LNCaP cells in both hypoxic (0.5% $O_2$) and normoxic (20% $O_2$) conditions (FIG. 24a). HSV1716 is readily taken up by macrophages and whilst uptake is significantly higher (p=0.002 at MO15 and p=0.001 at MO150) in normoxic culture conditions (FIG. 24b), viral replication is greater in hypoxia and macrophage cell death is equally effective in a hypoxic environment (FIG. 24c,d). In our in vivo model, tumor bearing mice received either a single intravenous injection of OV-carrying macrophages (MDM+OV) but were either not exposed to the MRI scanner, were static in the scanner but without MRT (MDM+OV (no MRT)), or were exposed to the scanner with MRT (MDM+OV+MRT). For the purpose of comparison "free" OV was administered to a separate group of mice. Additional control groups of mice received either 100 ul saline treatment (Control) or 3 million macrophages (MDM) intravenously. OV (1×10$^7$ pfu) {Sorensen et al., J Nucl Med 2012 53:647-654} alone significantly (P<0.03) delayed primary tumor growth for up to 7 days compared to mice receiving PBS or MDM only (FIG. 19a). This effect was significantly prolonged with macrophage-mediated delivery of HSV1716 (p<0.006 at day 14 and p<0.007 day 21). Of note, no differences were observed in mice receiving MDM+OV and MDM+OV (no MRT) where the latter is exposed to the scanner but with no steering. However, MRT targeting of our macrophage therapy was not only superior in reducing the size of the primary tumors from day 7 onwards this also delayed primary tumor regrowth for the entirety of the experiment (FIG. 19a).

Figure 19C:
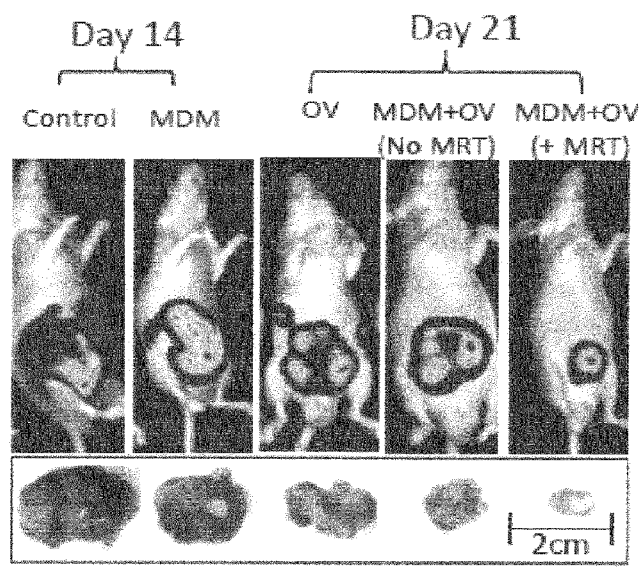
Figure 19D:
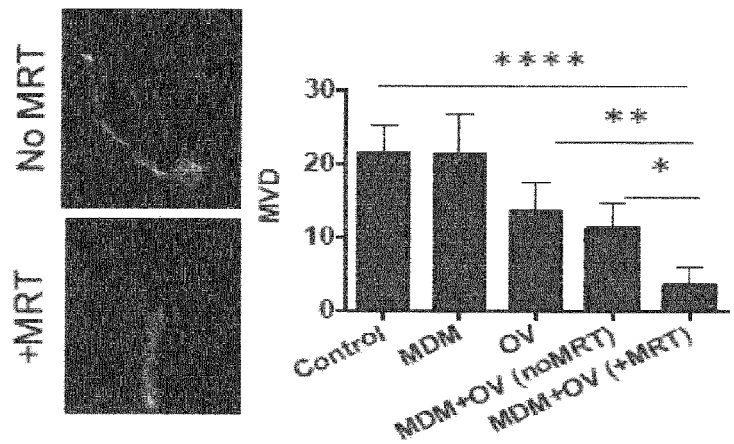
Figure 19E:
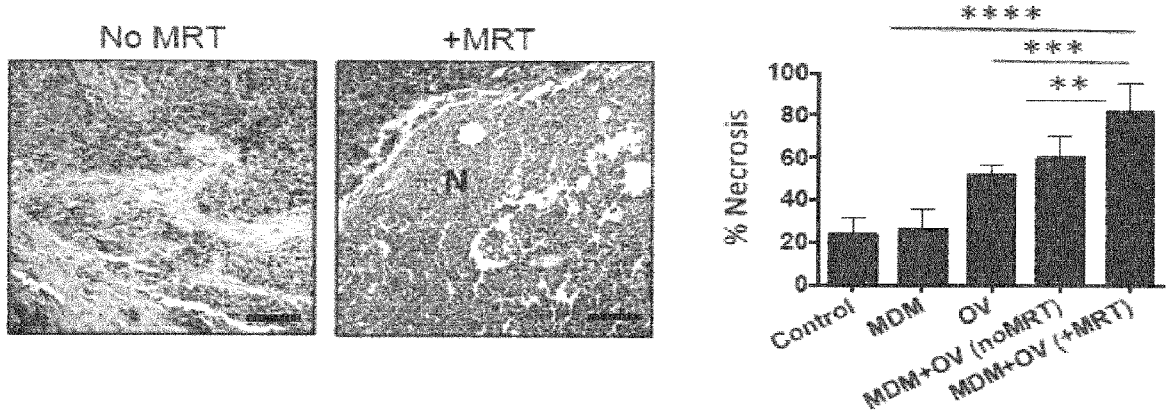

Bioluminescence of mice receiving macrophage OV therapy with or without MR targeting on the first day of treatment (day 0) and at the end of the experiment (day 21) showed this marked reduction of the primary tumor (FIGS. 19a & b). This was confirmed visually on the MRI scans (FIG. 19c). Furthermore, tumors undergoing MR targeting following macrophage-delivered OV were significantly more necrotic (p<0.001) than those not receiving MR targeting (FIG. 19e).

MR images of mice receiving macrophage OV therapy with or without MRT on the first day of treatment (day 0) and at the end of the experiment (day 21) reflect this marked reduction of the primary tumor. Interestingly, the tumors from mice treated with OV or MDM carrying OV were considerably paler and less vascularized and this correlated with a reduced microvessel density (MVD) compared with the PBS or MDM alone group. In mice undergoing MRT following macrophage-delivered OV significantly more necrosis (p<0.001) in tumors was observed than in the absence of MRT.

Figure 19F:
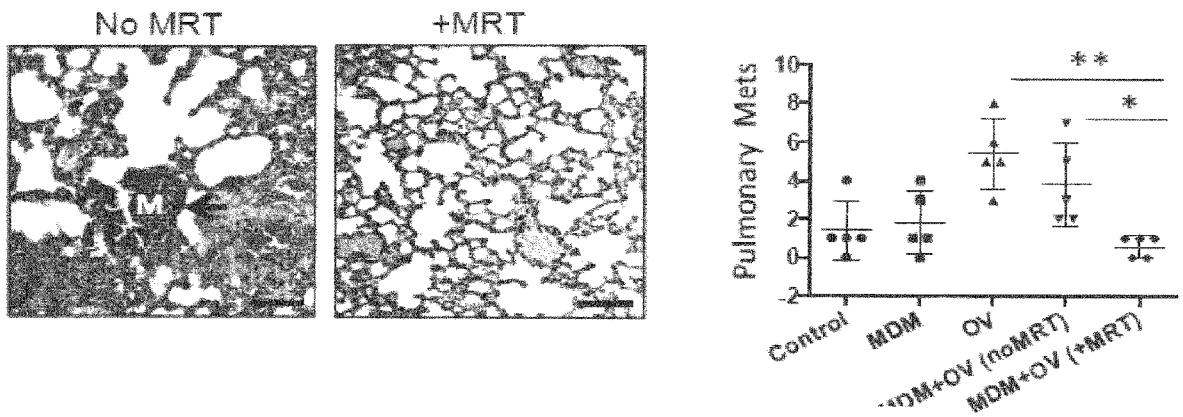

We next determined how these therapies influenced the development of pulmonary metastases. Few metastases were detected in mice injected with PBS or MDM alone since primary tumors in these groups had to be removed by day 14 (due to their size). Therefore, it was not valid to compare metastases in these control groups with the other experimental groups. However, the formation of lung metastases was markedly reduced when mice received MRT following delivery of OV-bearing macrophages in comparison to when no MRT was used (FIG. 19f 0.8±0.37 vs. 3.8±0.95 p<0.02).

In summary, we show that an MRI scanner can be used to non-invasively steer cells to both primary and secondary tumors within the body leading to a significant improvement in therapeutic outcome. Moreover, relaxometry measurements suggest that MRI post MRT can be used to assess the efficacy of this approach. Whilst this study has focused on cell delivery to tumors, the technology could be used to target any cells (e.g. stem cells) to a given tissue including non-phagocytic cell types which could be 'magnetised' using SPIO-conjugated antibodies directed against proteins on their cell surface.

The use of magnetic resonance targeting, which exploits the magnetic field gradients within magnetic resonance imaging systems to increase delivery of cells, is ideally suited to deep or superficial tissue. The question of clinical translation is dependent on the ability to provide the same targeting force on a clinical MRI system. Clinical scanners, with high performance magnetic field gradient systems of 300 mT/m, are already in use and as such have the potential to produce similar forces. Moreover, we were able to image the cell distributions following MRT, indicating the possibility for real-time image-guided targeting using an MRI system. These findings support the potential value of MRT with concomitant imaging for improved targeting of cells for therapy.

References for Example 3

1 Culme-Seymour, E. J., Davie, N. L., Brindley, D. A., Edwards-Parton, S. & Mason, C. A decade of cell therapy clinical trials (2000-2010). *Regenerative medicine* 7, 455-462, doi:10.2217/rme.12.45 (2012).
2 Menasche, P. Cardiac cell therapy: lessons from clinical trials. *Journal of molecular and cellular cardiology* 50, 258-265, doi:10.1016/j.yjmcc.2010.06.010 (2011).
3 Fischbach, M. A., Bluestone, J. A. & Lim, W. A. Cell-based therapeutics: the next pillar of medicine. *Sci Transl Med* 5, 179ps177, doi:10.1126/scitranslmed.3005568 (2013).
4 Syed, B. A. & Evans, J. B. Stem cell therapy market. Nature reviews. *Drug discovery* 12, 185-186, doi: 10.1038/nrd3953 (2013).
5 Kandalaft, L. E., Powell, D. J., Jr. & Coukos, G. A phase I clinical trial of adoptive transfer of folate receptor-alpha redirected autologous T cells for recurrent ovarian cancer. *J Transl Med* 10, 157, doi:10.1186/1479-5876-10-157 1479-5876-10-157 [pii] (2012).
6 Kershaw, M. H. et al. A phase I study on adoptive immunotherapy using gene-modified T cells for ovarian cancer. *Clin Cancer Res* 12, 6106-6115, doi:12/20/6106 [pii]10.1158/1078-0432.CCR-06-1183 (2006).
7 Engell-Noerregaard, L., Hansen, T. H., Andersen, M. H., Thor Straten, P. & Svane, I. M. Review of clinical studies on dendritic cell-based vaccination of patients with malignant melanoma: assessment of correlation between clinical response and vaccine parameters. *Cancer Immunol Immunother* 58, 1-14, doi:10.1007/s00262-008-0568-4 (2009).
8 Bartholeyns, J., Lopez, M. & Andreesen, R. Adoptive immunotherapy of solid tumors with activated macrophages: experimental and clinical results. *Anticancer Res* 11, 1201-1204 (1991).
9 Bartoleyns, J., Romet-Lemonne, J. L., Chokri, M. & Lopez, M. Immune therapy with macrophages: present status and critical requirements for implementation. *Immunobiology* 195, 550-562 (1996).
10 Studeny, M. et al. Bone marrow-derived mesenchymal stem cells as vehicles for interferon-beta delivery into tumors. *Cancer Res* 62, 3603-3608 (2002).
11 Kyrtatos, P. G. et al. Magnetic tagging increases delivery of circulating progenitors in vascular injury. *JACC. Cardiovascular interventions* 2, 794-802, doi:10.1016/j.jcin.2009.05.014 (2009).
12 Arbab, A. S. et al. In vivo trafficking and targeted delivery of magnetically labeled stem cells. *Hum Gene Ther* 15, 351-360, doi:10.1089/104303404322959506 (2004).
13 Riegler, J. et al. Targeted magnetic delivery and tracking of cells using a magnetic resonance imaging system. *Biomaterials* 31, 5366-5371, doi:10.1016/j.biomaterials.2010.03.032 S0142-9612(10)00388-1 [pii] (2010).
14 Muthana, M. et al. A novel magnetic approach to enhance the efficacy of cell-based gene therapies. Gene Ther (2008).

14 Yellen, B. B., Hovorka, O. & Friedman, G. Arranging matter by magnetic nanoparticle assemblers. *Proc Natl Acad Sci USA* 102, 8860-8864 (2005).
16 Martel, S. et al. Medical and technical protocol for automatic navigation of a wireless device in the carotid artery of a living swine using a standard clinical MRI system. *Medical image computing and computer-assisted intervention:MICCAI . . . International Conference on Medical Image Computing and Computer-Assisted Intervention* 10, 144-152 (2007).
17 Chanu, A. & Martel, S. Real-time software platform design for in-vivo navigation of a small ferromagnetic device in a swine carotid artery using a magnetic resonance imaging system. *Conf Proc IEEE Eng Med Biol Soc* 2007, 6585-6588, doi:10.1109/IEMBS.2007.4353868 (2007).
18 18 von zur Muhlen, C. et al. Imaging monocytes with iron oxide nanoparticles targeted towards the monocyte integrin MAC-1 (CD11b/CD18) does not result in improved atherosclerotic plaque detection by in vivo MRI. *Contrast media & molecular imaging* 5, 268-275, doi:10.1002/cmmi.384 (2010).
19 Daldrup-Link, H. E. et al. MRI of tumor-associated macrophages with clinically applicable iron oxide nanoparticles. *Clin Cancer Res* 17, 5695-5704, doi:1078-0432.CCR-10-3420 [pii]10.1158/1078-0432.CCR-10-3420 (2011).
20 De Palma, M. et al. Tumor-targeted interferon-alpha delivery by Tie2-expressing monocytes inhibits tumor growth and metastasis. *Cancer Cell* 14, 299-311, doi: 10.1016/j.ccr.2008.09.004 (2008).
21 Muthana, M. et al. Use of macrophages to target therapeutic adenovirus to human prostate tumors. *Cancer Res* 71, 1805-1815, doi:0008-5472.CAN-10-2349 [pii] 10.1158/0008-5472.CAN-10-2349 (2011).
22 Muthana, M. et al. Macrophage Delivery of an Oncolytic Virus Abolishes Tumor Regrowth and Metastasis After Chemotherapy or Irradiation. *Cancer Res*, doi:0008-5472.CAN-12-3056 [pii]10.1158/0008-5472.CAN-12-3056 (2013).
23 Surder, D. et al. Cell-based therapy for myocardial repair in patients with acute myocardial infarction: rationale and study design of the SWiss multicenter Intracoronary Stem cells Study in Acute Myocardial Infarction (SWISS-AMI). *American heart journal* 160, 58-64, doi:10.1016/j.ahj.2010.03.039 (2010).
24 Kim, B. G., Hwang, D. H., Lee, S. I., Kim, E. J. & Kim, S. U. Stem cell-based cell therapy for spinal cord injury. *Cell transplantation* 16, 355-364 (2007).
25 Garbayo, E. et al. Neuroprotective properties of marrow-isolated adult multilineage-inducible cells in rat hippocampus following global cerebral ischemia are enhanced when complexed to biomimetic microcarriers. *Journal of neurochemistry* 119, 972-988, doi:10.1111/j.1471-4159.2011.07272.x (2011).
26 Biju, K. C. et al. Bone marrow-derived microglia-based neurturin delivery protects against dopaminergic neurodegeneration in a mouse model of Parkinson's disease. *Neuroscience letters* 535, 24-29, doi:10.1016/j.neulet.2012.12.034 (2013).
27 Magga, J. et al. Production of monocytic cells from bone marrow stem cells: therapeutic usage in Alzheimer's disease. *Journal of cellular and molecular medicine* 16, 1060-1073, doi:10.1111/j.1582-4934.2011.01390.x (2012).

28 Branca, R. T. et al. Molecular MRI for sensitive and specific detection of lung metastases. *Proc Natl Acad Sci USA* 107, 3693-3697, doi:10.1073/pnas.1000386107 (2010).

28 Setsompop, K. et al. Pushing the limits of in vivo diffusion MRI for the Human Connectome Project. *NeuroImage* 80, 220-233, doi:10.1016/j.neuroimage.2013.05.078 (2013).

The invention claimed is:

1. An isolated ex vivo cell productively infected with an oncolytic herpes simplex virus wherein the cell is a macrophage and wherein the oncolytic herpes simplex virus is HSV1716 or a mutant thereof, wherein the oncolytic herpes simplex virus mutant is an ICP34.5 null mutant.

2. The cell of claim 1, further comprising super-paramagnetic iron oxide nanoparticles.

3. A method of treating a disease in a subject in need of treatment, the method comprising administering to said subject a preparation comprising a population of oncolytic herpes simplex virus-infected cells of claim 1.

4. The method of claim 3, wherein the disease is cancer.

5. The method of claim 3, wherein the population of oncolytic herpes simplex virus-infected cells further comprises super paramagnetic iron oxide nanoparticles.

6. The method of claim 5, wherein the method further comprises applying a magnetic field to the subject in order to direct the population of cells of the administered preparation to a desired location in the subject's body.

7. The method of claim 6, wherein the desired location is the site of a tumor.

8. The method of claim 7, wherein the tumor is in an organ selected from the group consisting of the adrenal gland, adrenal medulla, anus, appendix, bladder, bone, bone marrow, brain, breast, cecum, central nervous system, brain, cerebellum, cervix, colon, duodenum, endometrium, gallbladder, esophagus, heart, ileum, intestines, jejunum, kidney(s), lacrimal gland, larynx, liver, lung(s), lymph, lymph node, mediastinum, mesentery, myometrium, nasopharynx, omentum, ovary, pancreas, parotid gland, peripheral nervous system, peritoneum, pleura, prostate, rectum, salivary gland, colon, small intestine, spleen, stomach, testis, thymus, thyroid gland, and uterus.

9. The method of claim 3, wherein the population of oncolytic herpes simplex virus-infected cells is prepared by contacting a population of cells comprising macrophages with a quantity of oncolytic herpes simplex virus under suitable conditions and for sufficient time to permit productive infection of the macrophages.

10. The method of claim 9, wherein the cells are maintained in culture under conditions in which the virus is able to induce cell death.

11. The method of claim 10, wherein the population of oncolytic herpes simplex virus-infected cells comprises a mixture of intact and lysed macrophages.

12. The method of claim 10, wherein 1-50% of the population of oncolytic herpes simplex virus-infected cells of the preparation are dying or dead.

13. A population of oncolytic herpes simplex virus-infected cells of claim 1, wherein the population comprises a mixture of intact and lysed macrophages.

14. A population of oncolytic herpes simplex virus-infected cells of claim 13, wherein 1-50% of the population of oncolytic herpes simplex virus-infected cells of the preparation are dying or dead.

* * * * *

UNITED STATES PATENT AND TRADEMARK OFFICE
CERTIFICATE OF CORRECTION

| | |
|---|---|
| PATENT NO. | : 11,612,626 B2 |
| APPLICATION NO. | : 16/790459 |
| DATED | : March 28, 2023 |
| INVENTOR(S) | : Joe Conner, Munitta Muthana and Claire Elizabeth Lewis |

It is certified that error appears in the above-identified patent and that said Letters Patent is hereby corrected as shown below:

On the Title Page

Item (71) Applicants, please delete "Virttu Biologies Limited" and insert --Virttu Biologics Limited--.

Signed and Sealed this
Twelfth Day of September, 2023

*Katherine Kelly Vidal*

Katherine Kelly Vidal
*Director of the United States Patent and Trademark Office*

```
                           SEQUENCE LISTING

<160> NUMBER OF SEQ ID NOS: 20

<210> SEQ ID NO 1
<211> LENGTH: 21
<212> TYPE: DNA
<213> ORGANISM: Artificial sequence
<220> FEATURE:
<223> OTHER INFORMATION: Synthetic sequence: Forward primer

<400> SEQUENCE: 1
cgaaagtcaa ctccatctgc c                                            21

<210> SEQ ID NO 2
<211> LENGTH: 21
<212> TYPE: DNA
<213> ORGANISM: Artificial sequence
<220> FEATURE:
<223> OTHER INFORMATION: Synthetic sequence: Reverse primer

<400> SEQUENCE: 2
ggcaactggc tggaagtctc t                                            21

<210> SEQ ID NO 3
<211> LENGTH: 19
<212> TYPE: DNA
<213> ORGANISM: Artificial sequence
<220> FEATURE:
<223> OTHER INFORMATION: Synthetic sequence: Forward primer

<400> SEQUENCE: 3
gggccatcag ttgcaaatc                                               19

<210> SEQ ID NO 4
<211> LENGTH: 20
<212> TYPE: DNA
<213> ORGANISM: Artificial sequence
<220> FEATURE:
<223> OTHER INFORMATION: Synthetic sequence: Reverse primer

<400> SEQUENCE: 4
ttccttccgg tggtttcttc                                              20

<210> SEQ ID NO 5
<211> LENGTH: 21
<212> TYPE: DNA
<213> ORGANISM: Artificial sequence
<220> FEATURE:
<223> OTHER INFORMATION: Synthetic sequence: Forward primer

<400> SEQUENCE: 5
ccaggagaaa gtcagcctcc t                                            21

<210> SEQ ID NO 6
<211> LENGTH: 21
<212> TYPE: DNA
<213> ORGANISM: Artificial sequence
<220> FEATURE:
<223> OTHER INFORMATION: Synthetic sequence: Reverse primer

<400> SEQUENCE: 6
tcataccagg gcttgagctc a                                            21
```

-continued

<210> SEQ ID NO 7
<211> LENGTH: 21
<212> TYPE: DNA
<213> ORGANISM: Artificial sequence
<220> FEATURE:
<223> OTHER INFORMATION: Synthetic sequence: Forward primer

<400> SEQUENCE: 7
cacctctcaa gcagagcaca g                                         21

<210> SEQ ID NO 8
<211> LENGTH: 21
<212> TYPE: DNA
<213> ORGANISM: Artificial sequence
<220> FEATURE:
<223> OTHER INFORMATION: Synthetic sequence: Reverse primer

<400> SEQUENCE: 8
gggttccatg gtgaagtcaa c                                         21

<210> SEQ ID NO 9
<211> LENGTH: 22
<212> TYPE: DNA
<213> ORGANISM: Artificial sequence
<220> FEATURE:
<223> OTHER INFORMATION: Synthetic sequence: Forward primer

<400> SEQUENCE: 9
acctgagtct tctggaccgc tg                                        22

<210> SEQ ID NO 10
<211> LENGTH: 22
<212> TYPE: DNA
<213> ORGANISM: Artificial sequence
<220> FEATURE:
<223> OTHER INFORMATION: Synthetic sequence: Reverse primer

<400> SEQUENCE: 10
ccagccttct cccaagagtc gt                                        22

<210> SEQ ID NO 11
<211> LENGTH: 24
<212> TYPE: DNA
<213> ORGANISM: Artificial sequence
<220> FEATURE:
<223> OTHER INFORMATION: Synthetic sequence: Forward primer

<400> SEQUENCE: 11
taggaacagg cggcgacgaa taca                                      24

<210> SEQ ID NO 12
<211> LENGTH: 23
<212> TYPE: DNA
<213> ORGANISM: Artificial sequence
<220> FEATURE:
<223> OTHER INFORMATION: Synthetic sequence: Reverse primer

<400> SEQUENCE: 12
cacaatcaca aggcaacttc aat                                       23

<210> SEQ ID NO 13
<211> LENGTH: 20
<212> TYPE: DNA
<213> ORGANISM: Artificial sequence
<220> FEATURE:

<223> OTHER INFORMATION: Synthetic sequence: Forward primer

<400> SEQUENCE: 13
gcctaacatg cttcgagatc                                           20

<210> SEQ ID NO 14
<211> LENGTH: 20
<212> TYPE: DNA
<213> ORGANISM: Artificial sequence
<220> FEATURE:
<223> OTHER INFORMATION: Synthetic sequence: Reverse primer

<400> SEQUENCE: 14
ctcatggctt tgtagatgcc                                           20

<210> SEQ ID NO 15
<211> LENGTH: 22
<212> TYPE: DNA
<213> ORGANISM: Artificial sequence
<220> FEATURE:
<223> OTHER INFORMATION: Synthetic sequence: Forward primer

<400> SEQUENCE: 15
gaagttcatg gacgtctacc ag                                        22

<210> SEQ ID NO 16
<211> LENGTH: 23
<212> TYPE: DNA
<213> ORGANISM: Artificial sequence
<220> FEATURE:
<223> OTHER INFORMATION: Synthetic sequence: Reverse primer

<400> SEQUENCE: 16
catctgctat gctgcaggaa gct                                       23

<210> SEQ ID NO 17
<211> LENGTH: 22
<212> TYPE: DNA
<213> ORGANISM: Artificial sequence
<220> FEATURE:
<223> OTHER INFORMATION: Synthetic sequence: Forward primer

<400> SEQUENCE: 17
gaatttcccc agcatcccaa ag                                        22

<210> SEQ ID NO 18
<211> LENGTH: 22
<212> TYPE: DNA
<213> ORGANISM: Artificial sequence
<220> FEATURE:
<223> OTHER INFORMATION: Synthetic sequence: Reverse primer

<400> SEQUENCE: 18
tgccttctgc actcccttta tc                                        22

<210> SEQ ID NO 19
<211> LENGTH: 26
<212> TYPE: DNA
<213> ORGANISM: Artificial sequence
<220> FEATURE:
<223> OTHER INFORMATION: Synthetic sequence: Forward primer

<400> SEQUENCE: 19
agaatgtttt caaatgttct ccagtc                                    26

```
<210> SEQ ID NO 20
<211> LENGTH: 19
<212> TYPE: DNA
<213> ORGANISM: Artificial sequence
<220> FEATURE:
<223> OTHER INFORMATION: Synthetic sequence: Reverse primer

<400> SEQUENCE: 20
ggccatttgc ttggatccg                                               19
```